US 12,410,246 B2

(12) United States Patent
Phillips

(10) Patent No.: US 12,410,246 B2
(45) Date of Patent: Sep. 9, 2025

(54) ANTI-STEM CELL FACTOR ANTIBODIES AND METHODS OF BLOCKING THE INTERACTION BETWEEN SCF AND c-KIT

(71) Applicant: OPSIDIO, LLC, Bryn Mawr, PA (US)

(72) Inventor: Martin Phillips, Bryn Mawr, PA (US)

(73) Assignee: Opsidio, LLC, Bryn Mawr, PA (US)

( * ) Notice: Subject to any disclaimer, the term of this patent is extended or adjusted under 35 U.S.C. 154(b) by 0 days.

(21) Appl. No.: 18/500,622

(22) Filed: Nov. 2, 2023

(65) Prior Publication Data

US 2024/0076367 A1 Mar. 7, 2024

Related U.S. Application Data

(62) Division of application No. 17/022,465, filed on Sep. 16, 2020, now Pat. No. 11,939,373.

(60) Provisional application No. 62/900,927, filed on Sep. 16, 2019.

(51) Int. Cl.
| | | |
|---|---|---|
| C07K 16/24 | (2006.01) | |
| A61P 11/00 | (2006.01) | |
| A61P 11/06 | (2006.01) | |
| A61P 29/00 | (2006.01) | |
| A61P 37/08 | (2006.01) | |
| C12N 15/63 | (2006.01) | |
| A61K 39/00 | (2006.01) | |

(52) U.S. Cl.
CPC .............. *C07K 16/24* (2013.01); *A61P 11/00* (2018.01); *A61P 11/06* (2018.01); *A61P 29/00* (2018.01); *A61P 37/08* (2018.01); *C12N 15/63* (2013.01); *A61K 2039/505* (2013.01); *C07K 2317/24* (2013.01); *C07K 2317/33* (2013.01); *C07K 2317/34* (2013.01); *C07K 2317/56* (2013.01); *C07K 2317/565* (2013.01); *C07K 2317/76* (2013.01); *C07K 2317/77* (2013.01)

(58) Field of Classification Search
CPC ..... C07K 16/24; C07K 2317/34; C12N 15/63
See application file for complete search history.

(56) References Cited

U.S. PATENT DOCUMENTS

| | | | |
|---|---|---|---|
| 4,816,397 A | 3/1989 | Boss et al. | |
| 5,585,089 A | 12/1996 | Queen et al. | |
| 5,911,988 A | 6/1999 | Brownell et al. | |
| 6,331,415 B1 | 12/2001 | Cabilly et al. | |
| 7,285,640 B2 | 10/2007 | Takeuchi et al. | |
| 8,911,729 B2 * | 12/2014 | Lukacs .................. | C07K 16/24 424/139.1 |
| 9,353,178 B2 | 5/2016 | Lukacs et al. | |
| 10,501,535 B2 | 12/2019 | Lukacs et al. | |
| 10,927,153 B1 | 2/2021 | Adams et al. | |
| 11,939,373 B2 | 3/2024 | Phillips | |
| 2004/0214272 A1 | 10/2004 | La Rosa et al. | |
| 2005/0261175 A1 | 11/2005 | Zsebo et al. | |
| 2007/0202108 A1 | 8/2007 | Tandon et al. | |
| 2008/0248050 A1 | 10/2008 | Stevens | |
| 2008/0305074 A1 | 12/2008 | Zsebo et al. | |
| 2011/0189093 A1 | 8/2011 | Moffett et al. | |
| 2015/0018408 A1 | 1/2015 | Lukacs et al. | |
| 2015/0191729 A1 | 7/2015 | Suh et al. | |
| 2017/0152315 A1 | 6/2017 | Hansen et al. | |
| 2020/0255509 A1 | 8/2020 | Lukacs et al. | |
| 2021/0079084 A1 | 3/2021 | Phillips | |
| 2022/0324957 A1 | 10/2022 | Phillips | |
| 2022/0340655 A1 | 10/2022 | Phillips | |
| 2023/0019680 A1 | 1/2023 | Phillips | |
| 2024/0182556 A1 | 6/2024 | Bradbury | |

FOREIGN PATENT DOCUMENTS

| | | | |
|---|---|---|---|
| CN | 1889979 A | 1/2007 | |
| JP | 3583214 B2 | 11/2004 | |
| KR | 20170022409 A | 3/2017 | |
| KR | 20190049483 A | 5/2019 | |
| RU | 2681730 C2 | 3/2019 | |
| WO | WO-9109967 A1 | 7/1991 | |
| WO | WO-9202551 A1 | 2/1992 | |
| WO | WO-2005058815 A2 | 6/2005 | |
| WO | WO-2006002064 A2 | 1/2006 | |
| WO | WO-2012096960 A2 | 7/2012 | |
| WO | WO-2014018625 A1 | 1/2014 | |
| WO | WO-2017029583 A2 | 2/2017 | |
| WO | WO-2017035430 A2 * | 3/2017 | ......... C07K 16/2896 |
| WO | WO-2017112829 A1 | 6/2017 | |
| WO | WO-2018067071 A1 | 4/2018 | |
| WO | WO-2019066093 A1 | 4/2019 | |
| WO | WO-2019088658 A1 | 5/2019 | |
| WO | WO-2020081920 A1 | 4/2020 | |
| WO | WO-2021055408 A1 | 3/2021 | |

(Continued)

OTHER PUBLICATIONS

Mateu MG, et. al. Eur J Immunol. Jun. 1992;22(6):1385-9 (Year: 1992).*
Brown et al., J Immunol. May 1996;156(9):3285-91 (Year: 1996).*
Greenspan et al. 1999 Defining epitopes: It's not as easy as it seems; Nature Biotechnology, 17:936-937 (Year: 1999).*
Keller et al, The Cytokine Reference: A Compendium of Cytokines and Other Mediators of Host Defense (2001):877-897 (Year: 2001).*
Vajdos et al., J Mol Biol. Jul. 5, 2002;320(2):415-28 at 416 (Year: 2002).*
Trier et al, Methods 56 (2012) 136-144 (Year: 2012).*
Li et al, Vaccines 2014, 2, 515-536 (Year: 2014).*
Fonseca et al, Mucosal Immunol. Mar. 2019 ; 12(2): 445-456 (Year: 2019).*
Lebron, N. B., et al., "A human monoclonal antibody targeting the stem cell factor receptor (c-Kit) blocks tumor cell signaling and inhibits tumor growth", Cancer Biology & Therapy (Sep. 2014); 15(9): 1208-1218.

(Continued)

*Primary Examiner* — Vanessa L. Ford
*Assistant Examiner* — Danaya L Middleton
(74) *Attorney, Agent, or Firm* — COOLEY LLP

(57) ABSTRACT

The disclosure relates to antibodies and antigen-binding fragments thereof that bind to Stem Cell Factor (SCF). The antibodies and antigen-binding fragments thereof specifically bind to SCF248. The disclosure further relates to methods for making the antibodies, and to methods of use of the antibodies including methods of treatment for inflammatory and/or fibrotic diseases and disorders.

3 Claims, 39 Drawing Sheets

Specification includes a Sequence Listing.

(56) References Cited

FOREIGN PATENT DOCUMENTS

| WO | WO-2021055409 A1 | 3/2021 |
|---|---|---|
| WO | WO-2022197914 A2 | 9/2022 |

OTHER PUBLICATIONS

Abts, H., et al., "CD20 positive human B lymphocytes separated with the magnetic cell sorter (MACS) can be induced to proliferation and antibody secretion in vitro", Journal of Immunological Methods (1989); 125(1-2): 19-28.

Alam, M. E., et al., "Biophysical and sequence-based methods for identifying monovalent and bivalent antibodies with high colloidal stability", Molecular Pharmaceutics (2018); 15(1): 150-163.

Berlin, Aaron A., et al., "Inhibition of SCF attenuates peribronchial remodeling in chronic cockroach allergen-induced asthma", Laboratory Investigation (Jun. 2006); 86(6): 557-565.

Boder, E. T., et al., "Yeast surface display for screening combinatorial polypeptide libraries", Nature Biotechnology (1997); 15(6): 553-557.

Co-pending U.S. Appl. No. 18/550,438, inventor Bradbury; Andrew RM, filed Sep. 13, 2023.

Crooks, G. E., et al., "WebLogo: a sequence logo generator", Genome Research (2004); 14(6): 1188-1190.

Da Silva, C., et al., "Stem cell factor expression, mast cells and inflammation in asthma", Fundamental & Clinical Pharmacology (2006); 20(1): 21-39.

Ding, Lin, et al., "Essential role of stem cell factor—c-Kit signalling pathway in bleomycin-induced pulmonary fibrosis", The Journal of Pathology (Jun. 2013); 230(2): 205-214.

El Kossi, Mohsen MH, et al., "Stem cell factor and crescentic glomerulonephritis", American Journal of Kidney Diseases (Apr. 2003); 41(4): 785-795.

El-Koraie, Ahmed F., et al., "Role of stem cell factor and mast cells in the progression of chronic glomerulonephritides", Kidney International (2001); 60(1): 167-172.

Extended European Search Report for Application No. EP20865210.7, mailed on Oct. 27, 2023, 8 pages.

Extended European Search Report for European Application No. EP20866530.7 dated Sep. 18, 2023, 7 pages.

Ferrara, F., et al., "Using phage and yeast display to select hundreds of monoclonal antibodies: application to antigen 85, a tuberculosis biomarker", PloS one (2012); 7(11): e49535; 12 pages.

Fonseca, Wendy, et al., "Group 2 innate lymphoid cells (ILC2) are regulated by stem cell factor during chronic asthmatic disease", Mucosal Immunology (2019); 12(2): 445-456.

Garcia-Hernandez, V., et al., "Inhibition of Soluble Stem Cell Factor Promotes Intestinal Mucosal Repair", Inflammatory Bowel Diseases (2023); 29(izad003): 1133-1144.

GenBank Accession No. AML31316.1, "immunoglobulin heavy chain variable region, partial [Mus musculus]", Dec. 9, 2015 [retrieved Jan. 25, 2021], [online] Retrieved from the Internet, https://www.ncbi.nlm.nih.gov/protein/AML31316.1 , 2 pages.

GenBank Accession No. OGS00894.1, "hypothetical protein A3G85_00225 [Elusimicrobia bacterium RIFCSPLOWO2_12_FULL_39_28]", Jul. 8, 2016 [retrieved Jan. 25, 2021] [online] Retrieved from the Internet, https://www.ncbi.nlm.nih.gov/protein/OGS00894.1 , 7 pages.

Hunter, S. A., et al., "Cell-binding assays for determining the affinity of protein-protein interactions: technologies and considerations", Methods in Enzymology (2016); 580: 21-44.

International Application No. PCT/US2020/050973, International Preliminary Report on Patentability mailed Mar. 15, 2022, 6 pages.

International Application No. PCT/US2020/050973, International Search Report and Written Opinion mailed Feb. 19, 2021, 11 pages.

International Application No. PCT/US2020/050973, Invitation to Pay Additional Fees mailed Dec. 14, 2020, 2 pages.

International Application No. PCT/US2020/050974, International Preliminary Report on Patentability dated Mar. 15, 2022, 6 pages.

International Application No. PCT/US2020/050974, International Search Report and Written Opinion dated Feb. 24, 2021, 11 pages.

International Preliminary Report on Patentability for International Application No. PCT/US2022/020732 dated Sep. 28, 2023, 9 pages.

International Search Report and Written Opinion for Application No. PCT/US2022/020732, mailed on Sep. 2, 2022, 22 pages.

Invitation to Pay Additional Fees for International Application No. PCT/US22/20732, dated Jul. 5, 2022, 3 pages.

Kelly, R. L., et al., "Reduction of nonspecificity motifs in synthetic antibody libraries", Journal of Molecular Biology (2018); 430(1): 119-130.

Li, X., et al., "Glutamine deamidation: differentiation of glutamic acid and γ-glutamic acid in peptides by electron capture dissociation", Analytical Chemistry (2010); 82(9): 3606-3615.

Lowenthal, M. S., et al., "Identification of novel N-glycosylation sites at noncanonical protein consensus motifs", Journal of Proteome Research (2016); 15(7): 2087-2101.

Lukacs, N. W., "Therapeutic Mabs for Chronic Kidney Disesase", National Institute of Health (2019) [online] https://grantome.com/grant/NIH/R41-DK112426-01 (Access Date: Oct. 1, 20237); 3 pages.

Mendiaz, Elizabeth A., et al., "Epitope mapping and immunoneutralization of recombinant human stem-cell factor", European Journal of Biochemistry (1996); 239(3): 842-849.

Orr-Urtreger, Avi, et al., "Developmental expression of c-kit, a proto-oncogene encoded by the W locus", Development (1990); 109(4): 911-923.

Orr-Weaver, T. L., et al., "Yeast transformation: a model system for the study of recombination", Proceedings of the National Academy of Sciences (1981); 78(10): 6354-6358.

Powell, D. W., et al., "Epithelial cells and their neighbors I. Role of intestinal myofibroblasts in development, repair, and cancer", American Journal of Physiology-Gastrointestinal and Liver Physiology (2005); 289(1): G2-G7.

Powell, D. W., et al., "Myofibroblasts. II. Intestinal subepithelial myofibroblasts", American Journal of Physiology—Cell Physiology (1999); 277(2): C183-C201.

Rasky, Andrew, et al., "Inhibition of the stem cell factor 248 isoform attenuates the development of pulmonary remodeling disease", American Journal of Physiology—Lung Cellular and Molecular Physiology (2020); 318(1): L200-L211.

Sydow, J. F., et al., "Structure-based prediction of asparagine and aspartate degradation sites in antibody variable regions", PLoS one (2014); 9(6): e100736; 13 pages.

Tiller, K. E., et al., "Arginine mutations in antibody complementarity-determining regions display context-dependent affinity/specificity trade-offs", Journal of Biological Chemistry (2017); 292(40): 16638-16652.

UniProtKB Accession A0A1G7FT53, "Uncharacterized protein", May 8, 2019, [online] Retrieved from the Internet, https://www.uniprot.org/uniprot/A0A1G7FT53.txt?version=4 , 1 page.

Vlasak, J., et al., "Fragmentation of monoclonal antibodies", Mabs (2011); 3(3): 253-263.

International Search Report and Written Opinion for PCT Application No. PCT/US2024/053041 mailed Feb. 18, 2025, 14 pages.

Tayel et al.., "Association of stem cell factor gene expression with severity and atopic state in patients with bronchial asthma.", Respir Res. Jan. 18, 2017; 18(1): 21, 8 pages.

Holliger, P., et al., "Engineered antibody fragments and the rise of single domains", Nature Biotechnology (2005); 23(9): 1126-1136.

Invitation to Pay Additional fees for International Application No. PCT/US2024/053041, mailed Dec. 6, 2024, 2 pages.

Kohler, G., et al., "Pillars Article: Continuous Cultures of Fused Cells Secreting Antibody of Predefined Specificity", The Journal of Immunology (Mar. 2005); 174(5): 2453-2455. Reprinted with permission from Nature (Mar. 1975); 256(5517): 495-497.

Mountain, A., et al., "Engineering antibodies for therapy", Biotechnology & Genetic Engineering Reviews (1992); 10(1): 1-142.

Riechmann, L., et al.; "Reshaping human antibodies for therapy," Nature; 332(6162):323-327 (1988).

(56) References Cited

OTHER PUBLICATIONS

Simmons, L. C., et al., "Expression of full-length immunoglobulins in *Escherichia coli*: rapid and efficient production of aglycosylated antibodies", Journal of Immunological Methods (May 2002); 263(1-2): 133-147.

Verma, R., et al., "Antibody engineering: comparison of bacterial, yeast, insect and mammalian expression systems", Journal of Immunological Methods (Jul. 1998); 216(1-2): 165-181.

\* cited by examiner

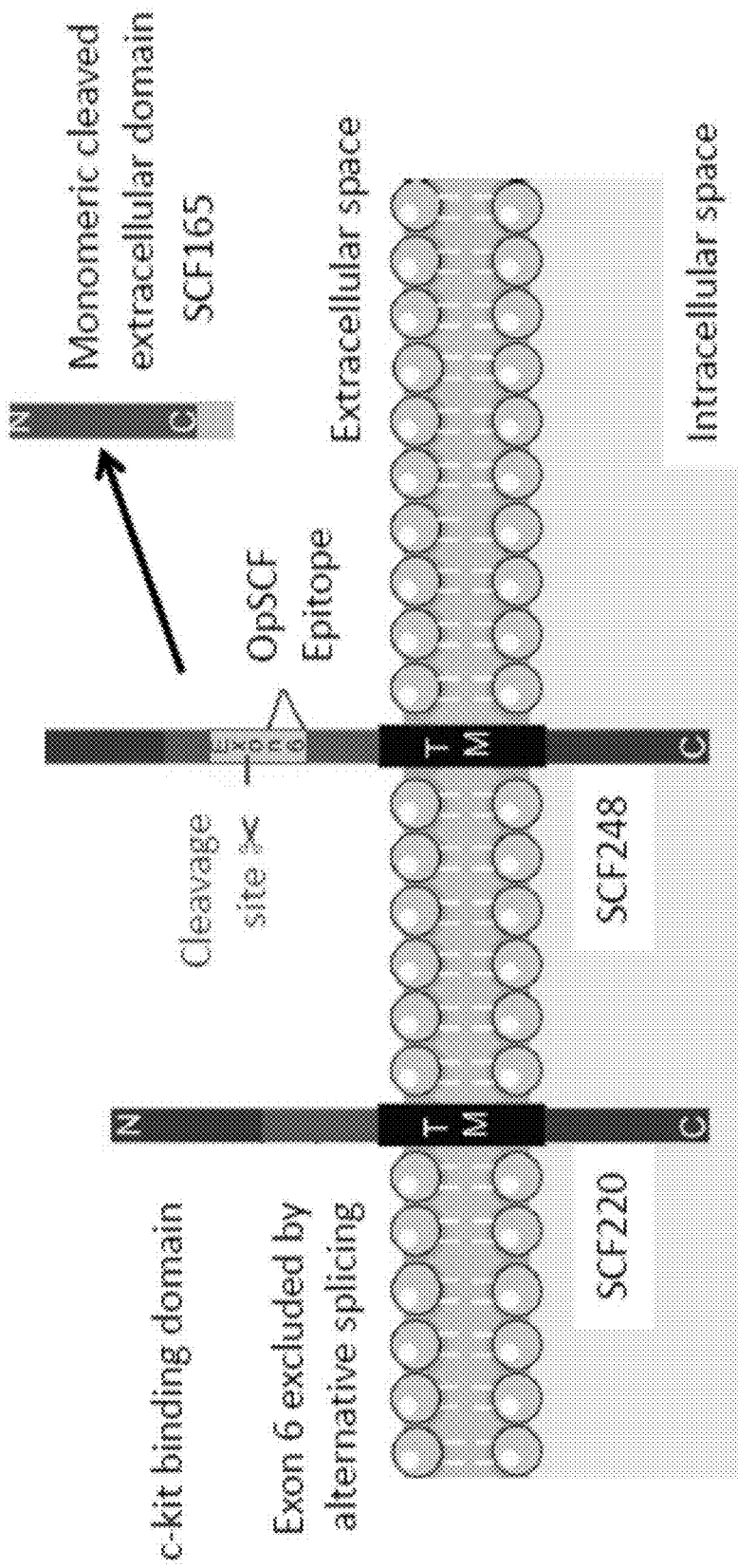

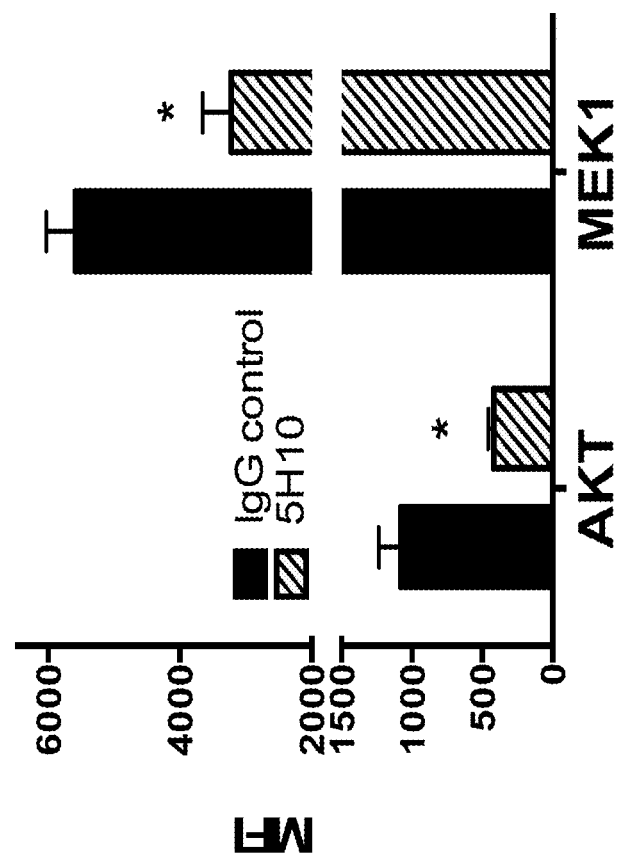

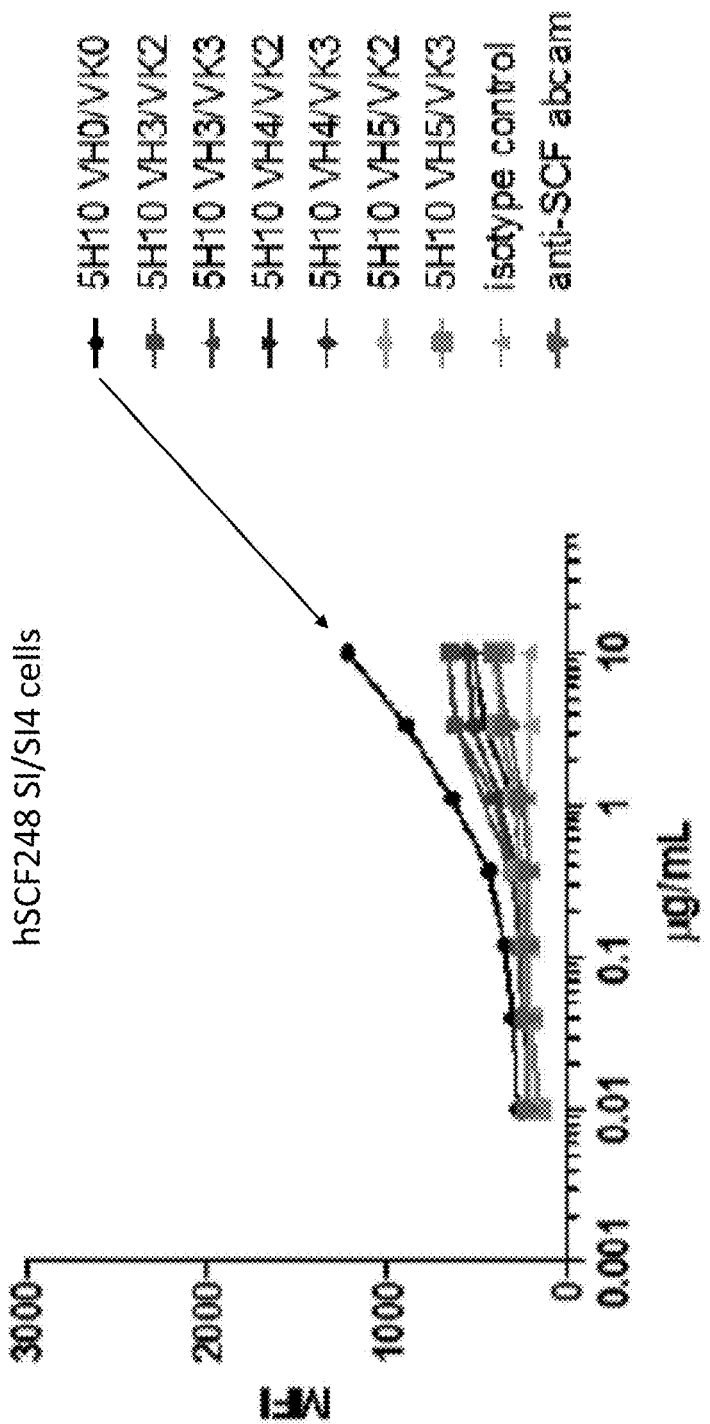

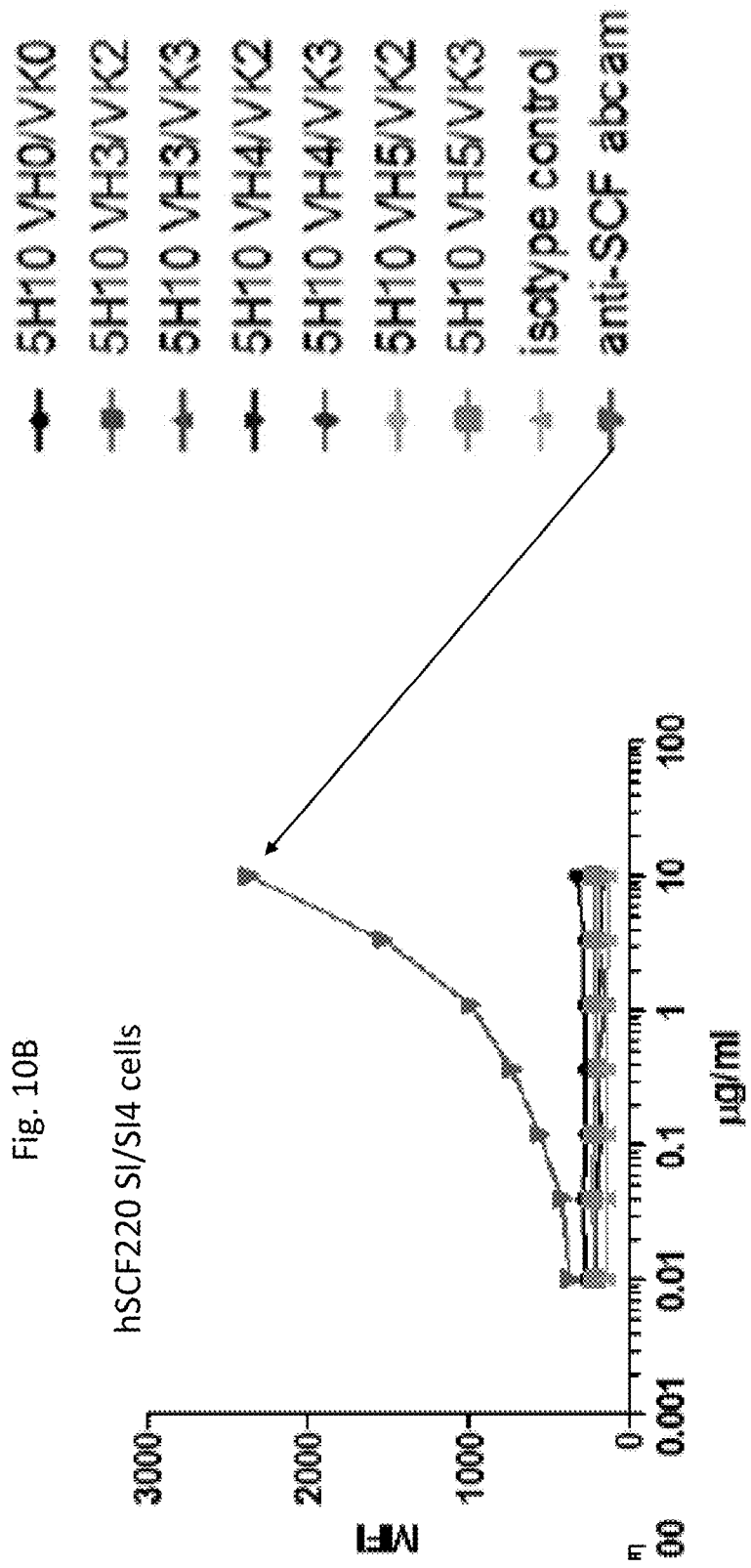

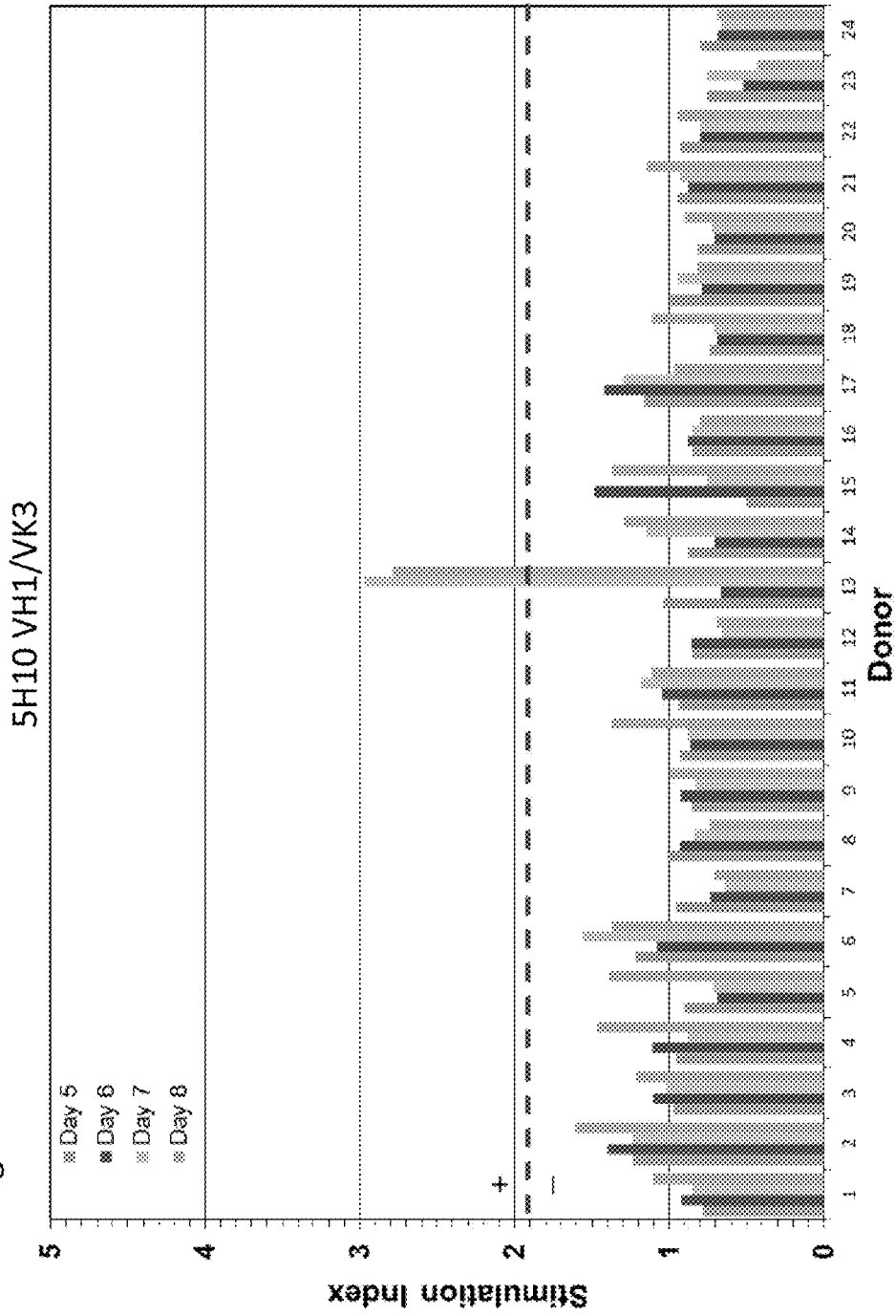

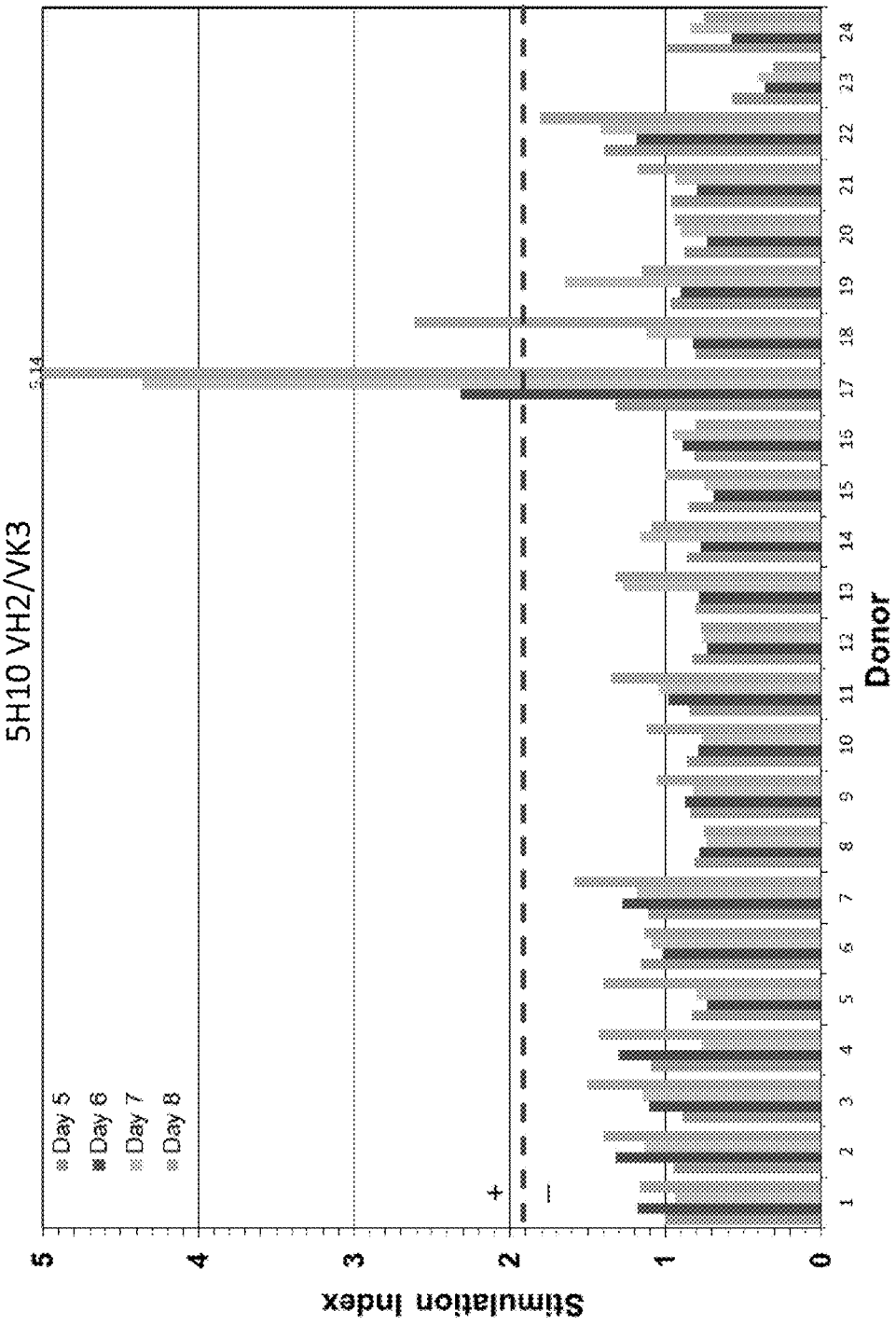

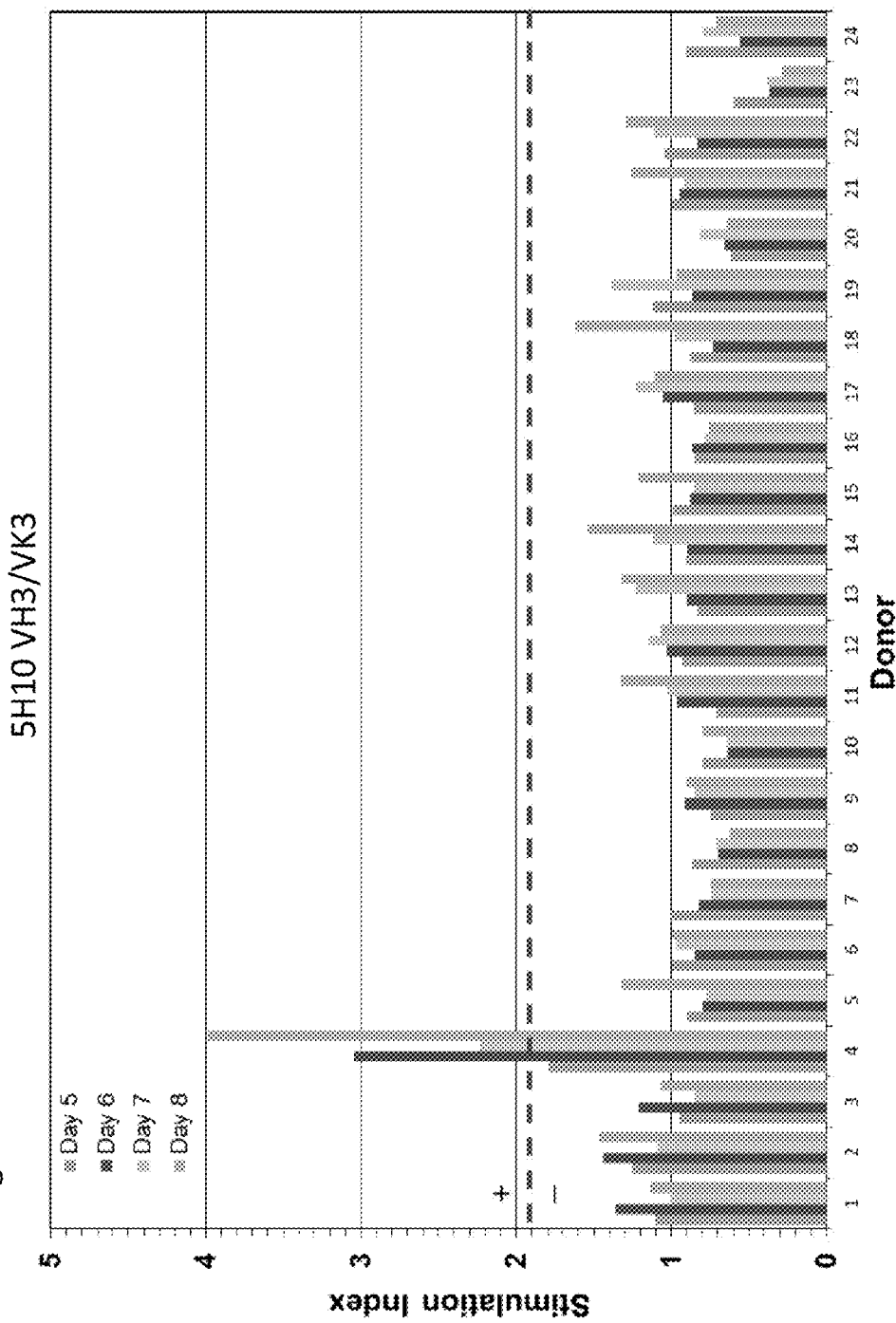

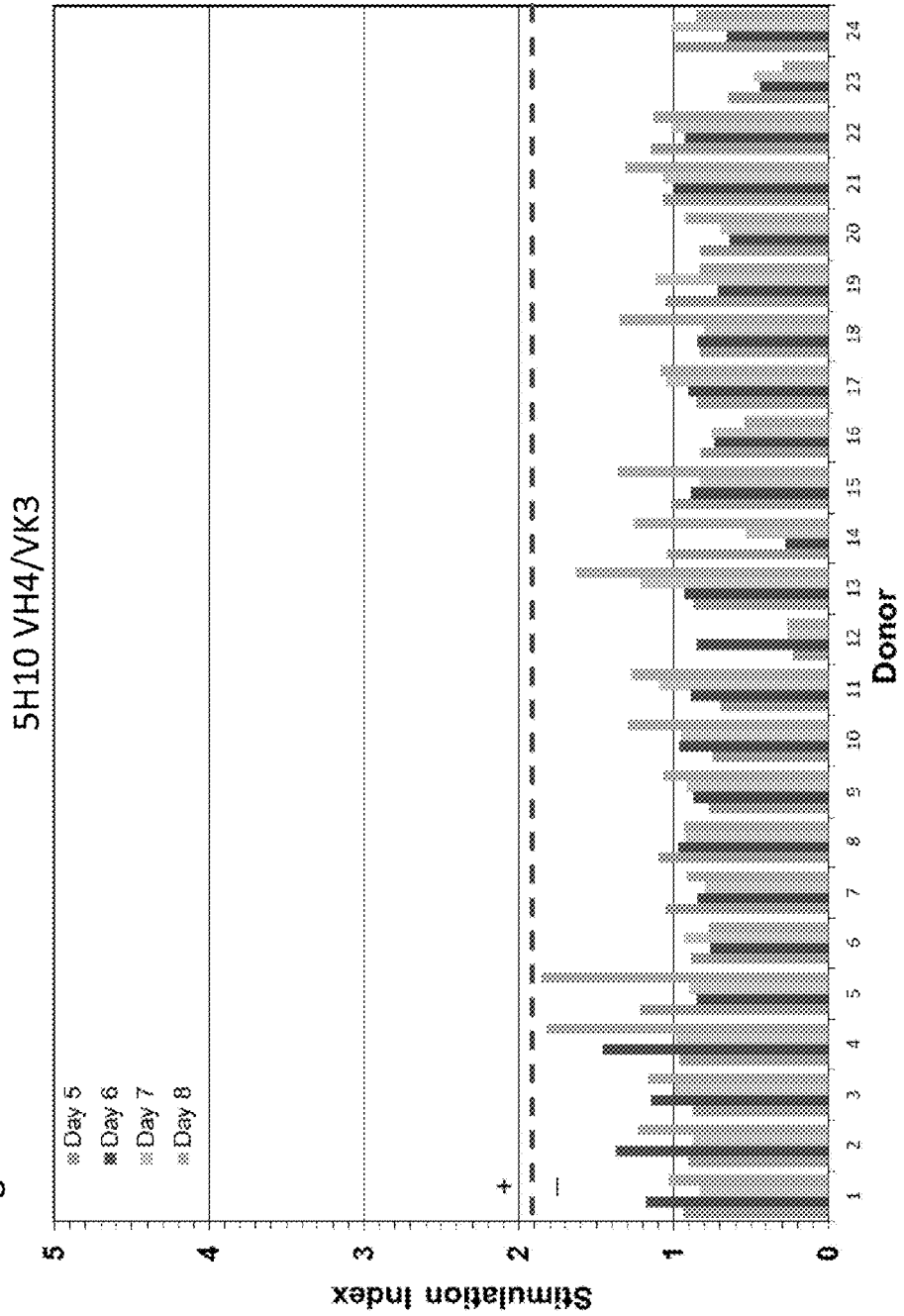

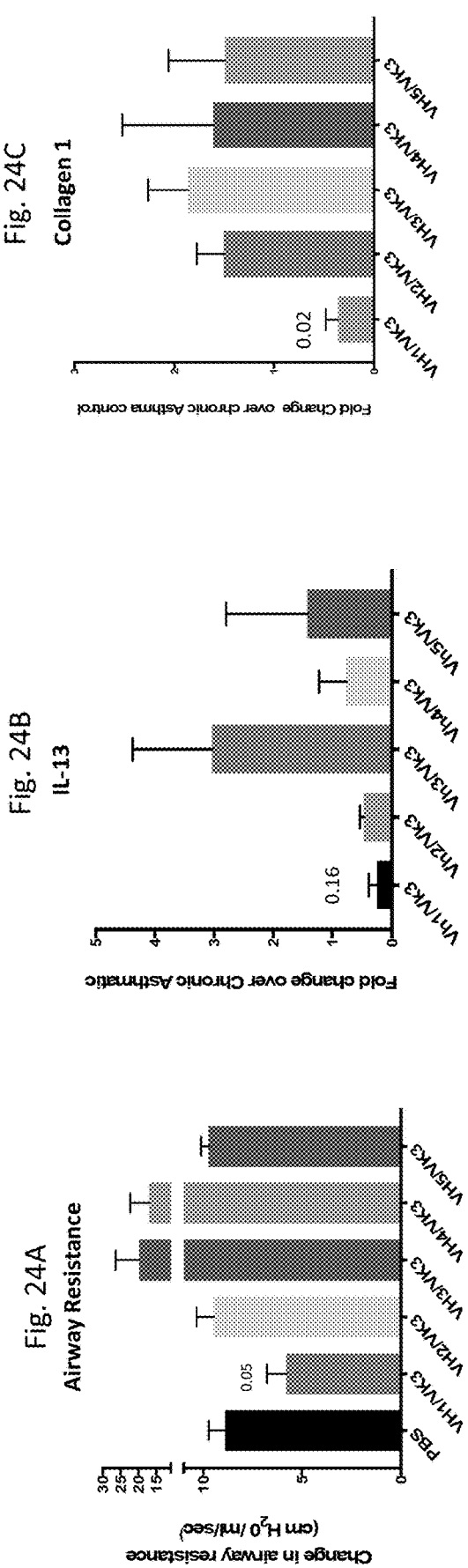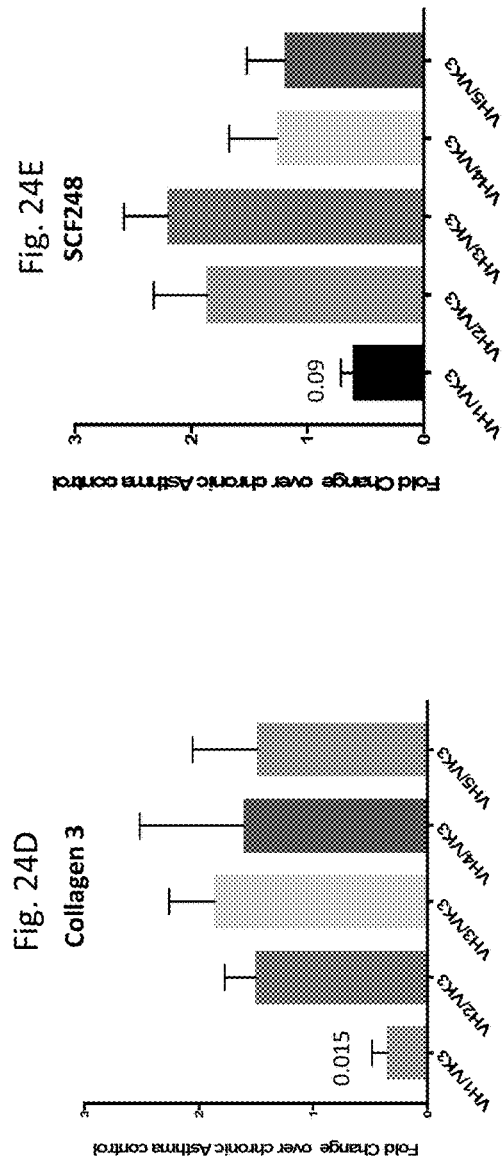

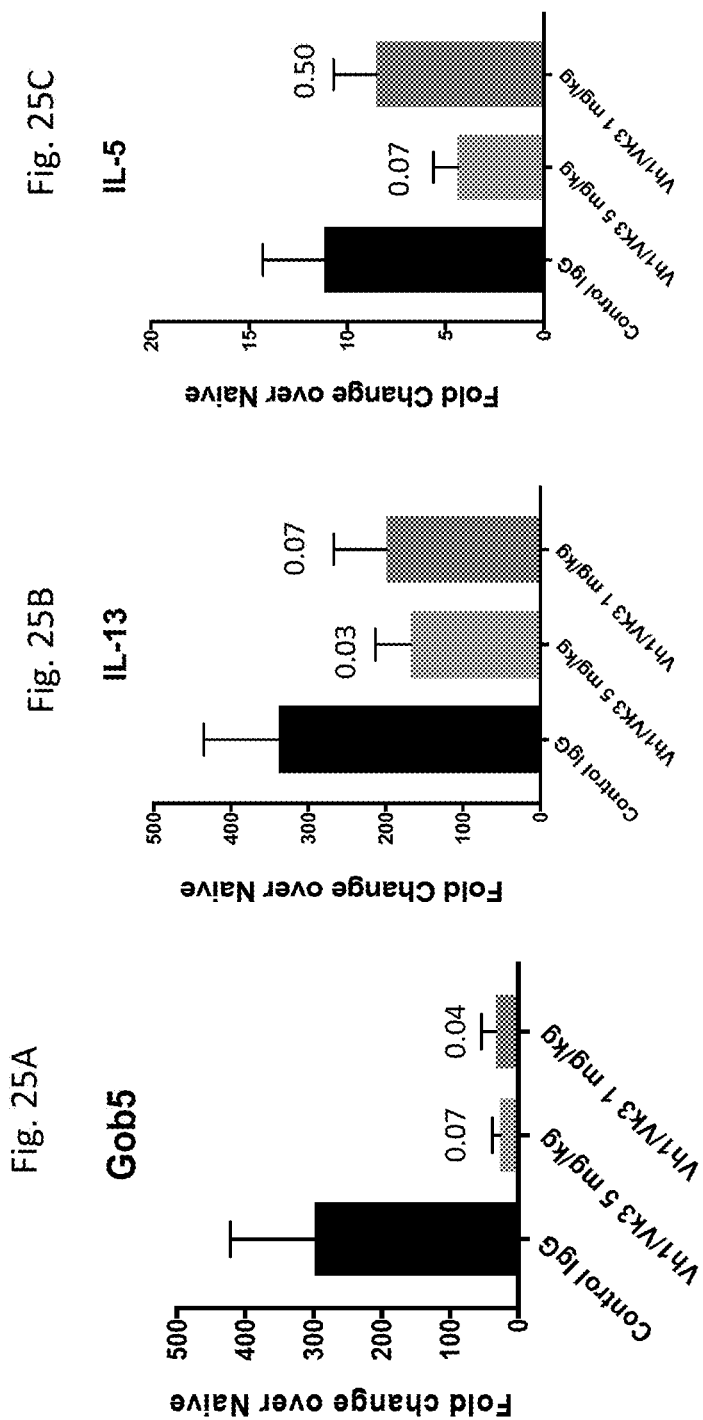

ANTI-STEM CELL FACTOR ANTIBODIES AND METHODS OF BLOCKING THE INTERACTION BETWEEN SCF AND c-KIT

CROSS-REFERENCE TO RELATED APPLICATIONS

This application is a divisional of U.S. application Ser. No. 17/022,465, filed Sep. 16, 2020, which claims the benefit of priority to U.S. Provisional Application No. 62/900,927, filed on Sep. 16, 2019. The contents of each of the aforementioned documents are incorporated by reference herein in their entireties.

FIELD

The present invention relates to antibodies and antigen-binding fragments thereof that bind to Stem Cell Factor (SCF) and particular portions thereof, and to methods of using such antibodies and antigen-binding fragments.

REFERENCE TO AN ELECTRONIC SEQUENCE LISTING

The contents of the electronic sequence listing (OPSL_001_05US_SeqList_ST26.xml; Size: 65,559 bytes; and Date of Creation: Oct. 12, 2023) is herein incorporated by reference in its entirety.

BACKGROUND

Inflammatory diseases are a major cause of morbidity and mortality worldwide. Some types of chronic inflammation can lead to fibrosis, which is the formation or development of excess fibrous connective tissue in an organ or tissue as a reparative or reactive process, as opposed to formation of fibrous tissue as a normal constituent of an organ or tissue. Chronic inflammation as well as fibrosis can affect nearly all tissues and organ systems, and fibrotic tissue remodeling can influence cancer metastasis and accelerate chronic graft rejection in transplant recipients.

Stem cell factor (SCF) and its receptor c-Kit are important factors of the perpetuation of chronic inflammation and in fibrotic diseases (El-Koraie, et al., Kidney Int. 60:167 (2001); Powell, et al., Am. J. Physiol. 289: G2 (2005); El Kossi, et al., Am. J. Kidney Dis. 41:785 (2003); Powell, et al., Am. J. Physiol. 277: C183 (1999) Ding et al J Pathol. 2013 June; 230(2):205-14., Berlin et al Lab Invest. 2006 June; 86(6):557-65, Rasky et al Am J Physiol Lung Cell Mol Physiol. 2020 Jan. 1; 318(1):L200-L211). c-Kit is a type III receptor-tyrosine kinase that is present in many cell types (Orr-Urtreger et al., Development 109:911 (1990). Immune cells such as mast cells, eosinophils, and innate lymphoid cells 2 and 3 (ILC2 and ILC3) are all c-Kit+ cells that may drive the chronic inflammatory process, depending on the disease and organ involved. Upon initiation of an inflammatory response, various mediators, including SCF, activate c-Kit+ immune cells, which in turn produce cytokines that cause fibroblasts to become activated myofibroblasts. Myofibroblasts secrete extracellular matrix proteins, collagen, and fibronectin, resulting in fibrosis of tissue. Activated myofibroblasts, activated epithelia, endothelia, macrophages, eosinophils, mast cells, monocytes, and other cells also express SCF on the cell surface, which activates more c-Kit+ immune cells, resulting in more cytokine release and perpetuating the inflammation.

There is a need in the art for more efficient and more specific treatments for inflammatory diseases. The present disclosure addresses this and other needs.

SUMMARY OF THE DISCLOSURE

In one aspect, the present disclosure provides antibodies and fragments thereof that specifically bind to stem cell factor (SCF). In some embodiments, the antibodies and fragments thereof specifically bind to the SCF isoform SCF248. In some embodiments, the antibodies and fragments thereof comprise heavy chain complementarity determining regions (CDRs), wherein heavy chain CDR1 CDR2, and CDR3 comprise SEQ ID NOs: 1, 2, and 3, respectively. In some embodiments, the antibodies and fragments thereof comprise light chain CDRs, wherein the light chain CDR1 CDR2, and CDR3 comprise SEQ ID NOs: 4, 5, and 6, respectively. In some embodiments, the antibodies and fragments thereof comprise heavy chain CDR1, CDR2, and CDR3 comprising SEQ ID NOs: 1, 37, and 3, respectively. In some embodiments, the antibodies and fragments thereof comprise a heavy chain variable region comprising at least 80%, at least 85%, at least 90%, at least 95%, or at least 99% identity to a sequence selected from the group consisting of SEQ ID NOs: 7, 8, 9, 10, 11, and 12. In some embodiments, the antibodies and fragments thereof comprise a light chain variable region comprising at least 80%, at least 85%, at least 90%, at least 95%, or at least 99% identity to a sequence selected from the group consisting of SEQ ID NOs: 13, 14, 15, 16, and 17. In some embodiments, the antibodies and fragments thereof comprise a heavy chain variable region comprising an amino acid sequence selected from the group consisting of SEQ ID NOs: 7, 8, 9, 10, 11, and 12, and a light chain variable region comprising an amino acid sequence selected from the group consisting of SEQ ID NOs: 13, 14, 15, 16, and 17.

In some embodiments, the antibody or fragment thereof comprises a heavy chain variable region amino acid sequence according to SEQ ID NO: 7 and a light chain variable region amino acid sequence according to SEQ ID NO: 16. In some embodiments, the antibody or fragment thereof of claim 1, wherein the antibody or fragment thereof comprises a heavy chain variable region amino acid sequence according to SEQ ID NO: 8 and a light chain variable region amino acid sequence according to SEQ ID NO: 16. In some embodiments, the antibody or fragment thereof comprises a heavy chain variable region amino acid sequence according to SEQ ID NO: 9 and a light chain variable region amino acid sequence according to SEQ ID NO: 16. In some embodiments, the antibody or fragment thereof comprises a heavy chain variable region amino acid sequence according to SEQ ID NO: 10 and a light chain variable region amino acid sequence according to SEQ ID NO: 16. In some embodiments, the antibody or fragment thereof comprises a heavy chain variable region amino acid sequence according to SEQ ID NO: 11 and a light chain variable region amino acid sequence according to SEQ ID NO: 16. In some embodiments, the antibody or fragment thereof comprises a heavy chain variable region amino acid sequence according to SEQ ID NO: 12 and a light chain variable region amino acid sequence according to SEQ ID NO: 16.

In some embodiments, the antibody or fragment thereof is humanized. In some embodiments, the antibody is a monoclonal antibody. In some embodiments, the antibody comprises a human IgG1 domain or a human IgG4 domain. In some embodiments, the antibody is an antigen binding fragment, wherein the fragment is selected from a Fab, F(ab')2, Fab', scFv, and single domain antibody (sdAb).

In some embodiments, the antibody or fragment thereof blocks the interaction between SCF (e.g. SCF248) and c-Kit. In some embodiments, the antibody specifically binds to SCF248. In some embodiments, the antibody does not bind to SCF220. In some embodiments, the antibody prevents the interaction of SCF248 and c-kit by causing the internalization of SCF, making it unavailable on the cell surface.

In one aspect, the present disclosure provides pharmaceutical compositions comprising the antibody or fragment thereof provided herein. In some embodiments, the pharmaceutical composition comprises a pharmaceutically acceptable carrier, diluent or excipient.

In some embodiments, the present disclosure provides isolated nucleic acid molecules encoding the antibody or fragment thereof provided herein. In some embodiments, the present disclosure provides an expression vector comprising the nucleic acid encoding the antibody or fragment thereof. In some embodiments, the present disclosure provides a recombinant host cell comprising the expression vector.

In one aspect, the present disclosure provides methods for making an antibody that specifically binds to stem cell factor isoform 248 (SCF248), the method comprising immunizing a host animal with a peptide comprising SEQ ID NO: 30 (ASSLRNDSSSSNRKAKNPPGD) or a fragment thereof, and obtaining an antibody from the immunized host animal. In some embodiments, the host animal is not a human. In some embodiments, the fragment of SEQ ID NO: 30 comprises at least 5, at least 6, at least 7, at least 8, at least 9, at least 10, at least 11, at least 12, at least 13, at least 14, at least 15, at least 16, at least 17, at least 18, at least 19, or 20 contiguous amino acids of SEQ ID NO: 30. In some embodiments, the fragment of SEQ ID NO: 30 comprises 5, 6, 7, 8, 9, 10, 11, 12, 13, 14, 15, 16, 17, 18, 19, or 20 contiguous amino acids of SEQ ID NO: 30. In some embodiments, the N-terminal amino acid of the fragment of SEQ ID NO: 30 is the alanine at position 1 at the N-terminus of SEQ ID NO: 30. In some embodiments, the method comprises immunizing the host animal with a peptide consisting of SEQ ID NO: 30. In some embodiments, the antibody from the immunized host animal is obtained from an immune cell isolated from the host animal. In some embodiments, the method further comprises generating a hybridoma using the immune cell. Thus, in some embodiments, the present disclosure provides hybridomas that produce monoclonal antibodies described herein.

In one aspect, the present disclosure provides an antibody or fragment thereof that specifically binds to SCF248, wherein the antibody or fragment thereof binds to an epitope comprising at least 8, at least 9, at least 10, at least 11, at least 12, or at least 13 contiguous amino acids of SEQ ID NO: 33, wherein the antibody inhibits the interaction of SCF248 with c-Kit. In further embodiments, the epitope comprises SEQ ID NO: 33 or SEQ ID NO: 36. In yet further embodiments, the epitope consists of SEQ ID NO: 33 or SEQ ID NO: 36.

In one aspect, the present disclosure provides compositions and methods for inhibiting the interaction between SCF and c-Kit. C-kit is expressed on immune cells, hematopoietic stem cells, and some structural cells. C-Kit's ligand SCF248 can be upregulated on myofibroblasts, activated epithelia, endothelia, macrophages, eosinophils, mast cells, and others. In some embodiments, the compositions and methods specifically inhibit the interaction between SCF248 and c-Kit. For example, in some embodiments, the compositions and methods specifically inhibit the interaction between SCF248 on myofibroblasts and c-Kit on immune cells. As another example, in some embodiments, the compositions and methods provided herein specifically inhibit the interaction between SCF248 on myofibroblasts, activated epithelia, endothelia, macrophages, eosinophils, mast cells, and/or monocytes; with c-Kit on immune cells and/or structural cells. In some embodiments, the methods comprise contacting SCF248 on myofibroblasts with an antibody or fragment thereof provided herein. In some embodiments, the antibody or fragment thereof provided herein blocks binding of SCF248 to c-Kit. In some embodiments, the blocking is via steric hindrance. In some embodiments, the antibody or fragment thereof provided herein internalizes SCF248.

In some embodiments, the present disclosure provides methods for inhibiting inflammation in a subject in need thereof, the method comprising administering to the subject an antibody or fragment thereof provided herein. In some embodiments, the present disclosure provides methods for inhibiting an inflammatory disease in a subject in need thereof, the method comprising administering to the subject an antibody or fragment thereof provided herein. In further embodiments, the inflammatory disease is a chronic inflammatory disease. In some embodiments, the present disclosure provides methods for treating inflammation and/or a chronic inflammatory disease in a subject in need thereof, the method comprising administering to the subject an antibody or fragment thereof provided herein.

In some embodiments, the present disclosure provides methods for inhibiting fibrosis in a subject in need thereof, the method comprising administering to the subject an antibody or fragment thereof provided herein. In some embodiments, the present disclosure provides methods for treating a fibrotic disease in a subject in need thereof, the method comprising administering to the subject an antibody or fragment thereof provided herein. In embodiments, the method further comprises administering one or more additional therapy and/or therapeutic agent.

In some embodiments, the inflammatory disease or fibrotic disease is selected from the group consisting of urticaria, atopic dermatitis, bullous pemphigoid, scleroderma, systemic sclerosis, non-alcoholic steatohepatitis (NASH), primary sclerosing cholangitis, liver cirrhosis, pulmonary fibrosis (e.g., idiopathic pulmonary fibrosis (IPF), scleroderma lung fibrosis), chronic obstructive pulmonary disease (COPD), acute respiratory distress syndrome (ARDS), cystic fibrosis, peribronchial fibrosis, hypersensitivity pneumonitis, asthma, bleomycin lung, endomyocardial fibrosis, fibromyalgia, eosinophilic esophagitis, radiation fibrosis, rheumatoid arthritis, and inflammatory bowel disease.

BRIEF DESCRIPTION OF THE FIGURES

FIG. 3 shows the isoforms of SCF, SCF220 and SCF 248; and the monomeric cleaved extracellular domain, SCF165. SCF165 is released upon cleavage of SCF248 at its cleavage site within the Exon 6 region.

FIG. 6 shows the activation of the P13K/AKT pathway and the MEK/ERK pathway of c-kit signaling after contacting eosinophils with an SCF248-expressing cells in the presence of 5H10 antibody or IgG control. 5H10 antibody significantly reduced activation of both pathways.

FIG. 10A-FIG. 10B shows binding of 5H10 humanized variants at different antibody concentrations by flow cytometry to Sl/Sl4 hSCF248 cells (FIG. 10A) and Sl/Sl4 hSCF220 cells (FIG. 10B).

In FIG. 11C, the indicated VH is paired with VK3. In FIG. 11D, the 5H10 antibody shown is VH1/VK3.

FIG. 15A-FIG. 15H shows the CD4+ T cell responses induced by the indicated 5H10 humanized variants in an EPISCREEN™ time course T cell proliferation assay. Exenatide and KLH, shown in FIGS. 15G and 15H, respectively, are positive controls.

FIG. 24A-24E provide results of treatment with humanized 5H10 antibodies in the in vivo model of chronic allergic asthma. FIG. 24A shows that airway resistance as measured was significantly reduced in animals treated with VH1/VK3 compared to PBS control. IL-13 mRNA (FIG. 24B), Collagen 1 mRNA (FIG. 24C), and Collagen 3 mRNA (FIG. 24D) in lung tissues were also reduced in animals treated with VH1/VK3 compared to the chronic asthma (PBS) control. FIG. 24E shows that SCF248 mRNA expression was also reduced in animals treated with VH1/VK3 5H10 antibody compared to PBS control.

FIG. 25A-25C show that antibody VH1/VK3 reduced mRNA levels of mucus protein Gob5 (FIG. 25A), IL-13 (FIG. 25B), and IL-5 (FIG. 25C), at concentrations of 1 mg/kg and 5 mg/kg in vivo.

DETAILED DESCRIPTION

Figure 1:
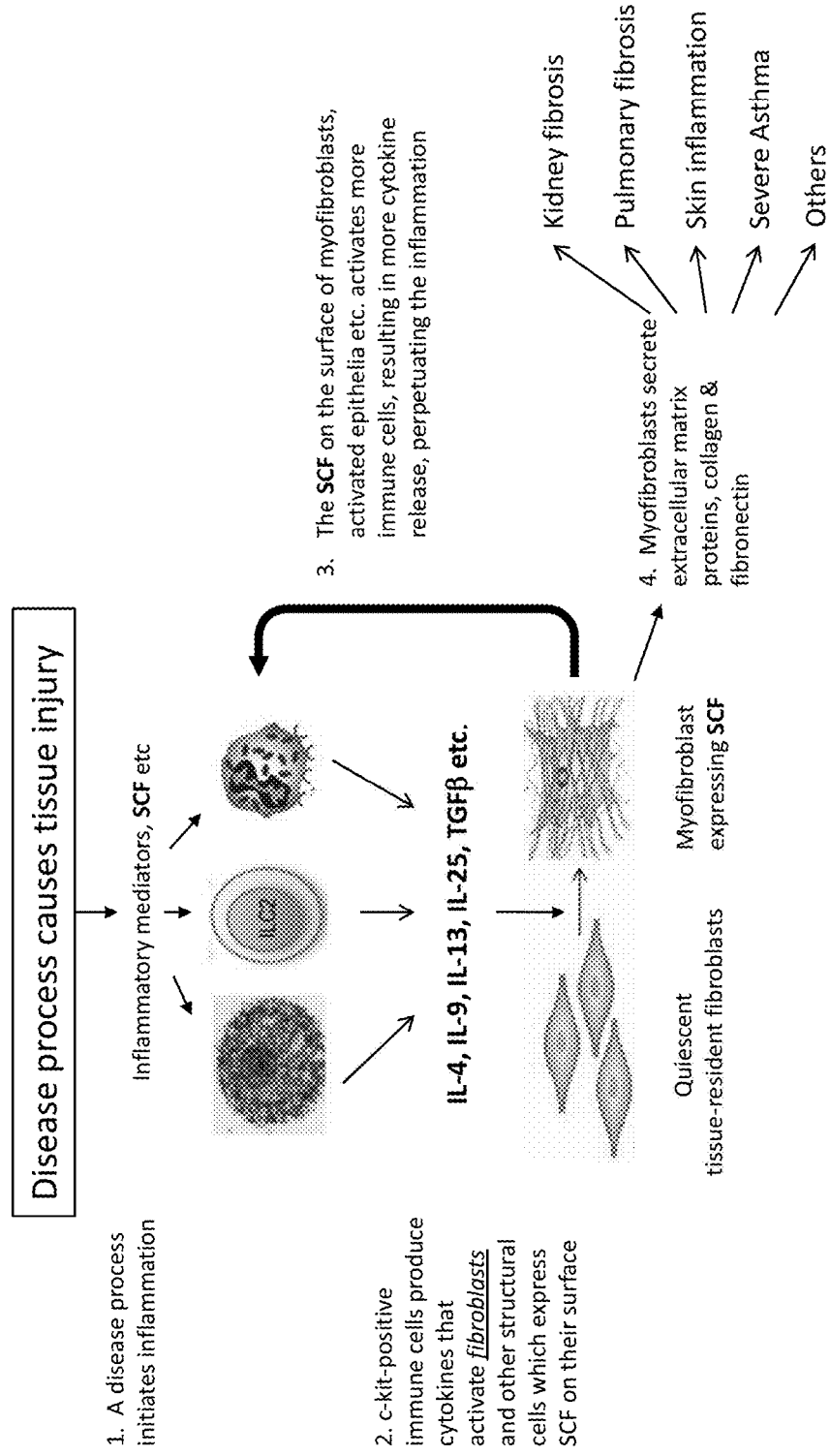
FIG. 1 provides a schematic overview of the tissue injury/inflammatory disease process.

Stem Cell Factor (SCF) is a key mediator of acute and chronic inflammation, fibrotic diseases, and tissue remodeling diseases. The interaction of SCF with c-Kit on immune cells initiates and perpetuates inflammation and fibrosis. The present disclosure provides compositions and methods for inhibiting the interaction of SCF with c-Kit. In one aspect, the present disclosure provides compositions and methods for preventing the inflammatory form of SCF, SCF248, from interacting with c-Kit and thus reduces and/or prevents activation of immune cells. Thus, the present disclosure provides methods for treating chronic inflammation and fibrotic and tissue remodeling diseases. In one aspect, the present disclosure provides compositions and methods for reducing the accumulation (e.g., proliferation and/or retention) of immune cells in an organ or tissue. For example, the disclosure provides compositions and methods that prevent SCF248 from interacting with c-Kit and thus reduces and/or prevents accumulation of immune cells in organs or tissues. In some embodiments, the disclosure provides compositions and methods for reducing and/or preventing the activation and/or accumulation in organs or tissues of mast cells, eosinophils, type 2 innate lymphoid (ILC2) cells, and type 3 innate lymphoid (ILC3) cells.

In particular, the present disclosure provides antibodies and fragments thereof that specifically bind to SCF and block or inhibit its interaction with c-Kit. In some embodiments, the antibodies and fragments provided herein bind to SCF and inhibit the activity of c-Kit and c-Kit+ cells. The disclosure also provides methods for generating antibodies and fragments thereof that specifically bind to SCF, as well as diagnostic and therapeutic methods of use thereof. In one aspect, the antibodies and fragments thereof provided herein specifically bind to the SCF isoform that drives inflammation, SCF248. Thus, the present disclosure provides specific, effective compositions and methods for inhibiting inflammation and fibrosis and treating chronic inflammatory diseases and fibrotic diseases.

Definitions

As used herein, the term "antibody" refers to a binding protein having at least one antigen binding domain. The antibodies and fragments thereof of the present invention may be whole antibodies or any fragment thereof. Thus, the antibodies and fragments of the invention include monoclonal antibodies or fragments thereof and antibody variants or fragments thereof, as well as immunoconjugates. Antigen binding fragments include Fab fragments, Fab' fragments, F(ab')2 fragments, bispecific Fab dimers (Fab2), trispecific Fab trimers (Fab3), Fv, single chain Fv proteins ("scFv"), bis-scFv, (scFv) 2, minibodies, diabodies, triabodies, tetrabodies, disulfide stabilized Fv proteins ("dsFv"), single-domain antibodies (sdAb, nanobody), heavy-chain only antibodies (e.g., camelid VHH, camelid nanobody, shark Ig NAR), and portions of full length antibodies responsible for antigen binding. An isolated antibody or antigen binding fragment thereof is one which has been identified and separated and/or recovered from a component of its natural environment.

In some embodiments, the antibodies and antigen binding fragments thereof are isolated antibodies and fragments thereof, Thus, the present invention provides isolated antibodies and antigen binding fragments thereof, and nucleic acids encoding such antibodies and fragments, as well as compositions comprising such isolated antibodies, fragments, and nucleic acids. The term "isolated" refers to a compound of interest (e.g., an antibody or nucleic acid) that has been separated from its natural environment. The present invention further provides pharmaceutical compositions comprising the isolated antibodies or fragments thereof, or nucleic acids encoding such antibodies or fragments, and further comprising one or more pharmaceutically acceptable carrier. Pharmaceutically acceptable carriers include, for example, excipients, diluents, encapsulating materials, fillers, buffers, or other agents.

As used herein, the term "derived" when used to refer to a molecule or polypeptide relative to a reference antibody or other binding protein, means a molecule or polypeptide that is specific for, and capable of binding to, the same epitope as the reference antibody or other binding protein.

As used herein, the phrase "specific for" may mean that the antibody does not bind to the target due to only non-specific interactions, and this property can be determined by comparison to an isotype control or similar. Specific binding does not necessarily require, although it may include, exclusive binding to a single target. In embodiments, the antibodies provided herein specifically bind to SCF248, and do not bind SCF220.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

A "variant" of a polypeptide (e.g., an antigen binding protein, or an antibody) comprises an amino acid sequence wherein one or more amino acid residues are inserted into, deleted from and/or substituted into the amino acid sequence relative to another polypeptide sequence. Variants include antibodies and fragments thereof that have a recited percent identity to an antibody or fragment provided herein or to an antibody or fragment having a recited DNA or amino acid sequence.

The term "identity" refers to a relationship between the sequences of two or more polypeptide molecules or two or more nucleic acid molecules, as determined by aligning and comparing the sequences. "Percent identity," "percent homology," "sequence identity," or "sequence homology" and the like mean the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073. In calculating percent identity, the sequences being compared are typically aligned in a way that gives the largest match between the sequences.

The term "light chain" includes a full-length light chain and fragments thereof having sufficient variable region sequence to confer binding specificity. A full-length light chain includes a variable region domain and a constant region domain. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, three constant region domains, $C_H1$, $C_H2$, and $C_H3$. The variable heavy domain is at the amino-terminus of the polypeptide, and the $C_H$ domains are at the carboxyl-terminus, with the CH3 being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE. The term "isotype" refers to the antibody class encoded by the heavy chain constant region genes. In some embodiments, the antibodies provided herein have an IgG4 heavy chain, or an IgG4 heavy chain comprising certain amino acid mutations. For example, in some embodiments, the IgG4 comprises a mutation at position 228 (EU numbering scheme, Kabat et al. Sequence of proteins of immunologic interest, 5th ed Bethesda, MD, NIH 1991) to inhibit Fab arm exchange. For example, in some embodiments, the IgG4 heavy chain is an IgG4 S228P heavy chain. In some embodiments, the heavy chain comprises one or more amino acid mutations that reduce binding to Fc receptors, and thereby reduce or eliminate effector function of the antibody. For example, the heavy chain may comprise mutations at one or more of positions 233, 234, 235, 236, 237, 265, 309, 331, and 409 (EU numbering).

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target. The term "target," as used herein, refers to a molecule or a portion of a molecule capable of being bound by an antigen binding protein. In certain embodiments, a target can have one or more epitopes. In certain embodiments, a target is an antigen. The use of "antigen" in the phrase "antigen binding protein" simply denotes that the protein sequence that comprises the antigen can be bound by an antibody. In this context, it does not require that the protein be foreign or that it be capable of inducing an immune response.

The term "epitope" includes any determinant capable being bound by an antigen binding protein, such as an antibody or to a T-cell receptor. An epitope is a region of an antigen that is bound by an antigen binding protein that targets that antigen, and when the antigen is a protein, includes specific amino acids that directly contact the antigen binding protein. Most often, epitopes reside on proteins, but in some instances can reside on other kinds of molecules, such as nucleic acids. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of proteins and/or macromolecules. Antibody epitopes may be linear or conformational. In embodiments, the epitope provided herein is a linear epitope.

The use of the singular includes the plural unless specifically stated otherwise. The word "a" or "an" means "at least one" unless specifically stated otherwise. The use of "or" means "and/or" unless stated otherwise. The meaning of the phrase "at least one" is equivalent to the meaning of the phrase "one or more." Furthermore, the use of the term "including," as well as other forms, such as "includes" and "included," is not limiting. Also, terms such as "element" or "component" encompass both elements or components comprising one unit and elements or components comprising more than one unit unless specifically stated otherwise. As used herein, the term "about" refers to an amount more or less than the stated parameter value, for example plus or minus five or ten percent of the object that "about" modifies, or as one of skill in the art would recognize from the context (e.g., approximately 50% of the interval between values). The term "about" also includes the value referenced.

Stem Cell Factor

In humans, there are at least two forms of SCF, which have different structures and activities. SCF220 functions in several homeostatic functions, including hematopoiesis and spermatogenesis and is found in bone marrow, testis, and other tissues and organs. SCF220 is slowly cleavable and sometimes called "membrane SCF." In contrast, SCF248 is rapidly cleavable and comprises a cleavage site in exon 6, located between the N-terminal c-kit binding domain and the transmembrane domain. SCF248 may be referred to as "soluble SCF". Exon 6 is excluded from SCF220 via alternative splicing, and SCF220 thus lacks this cleavage site. A monomeric, extracellular domain (SCF165) is the cleavage product and serves as a biomarker in plasma for chronic inflammatory diseases. Plasma may also contain detectable levels of SCF extracellular domain that comes from SCF220, but the majority of detectable extracellular domain is expected to be SCF165. SCF248 is the isoform found on myofibroblasts, activated epithelial cells, and other cells, which activates immune cells during inflammation and contributes to perpetuation of fibrosis. More specifically, SCF248 binds to c-Kit on immune cells, initiating production of cytokines that activate fibroblasts to become myofibroblasts, which secrete extracellular matrix proteins, collagen, and fibronectin. The activated myofibroblasts as well as activated epithelia, endothelia, macrophages, eosinophils, mast cells, monocytes, and other cells also express SCF on the cell surface, activating more c-Kit+ immune cells, resulting in further cytokine release and immune activation and fibrotic responses.

The antibodies and antigen-binding fragments thereof disclosed herein are specific for SCF. In some embodiments, the antibodies and fragments thereof are specific for human SCF. In some embodiments, the antibodies and fragments thereof are specific for SCF248. In some embodiments, the antibodies bind SCF248 and do not bind other isoforms of SCF. In some embodiments, the antibodies bind SCF248 and do not bind to SCF220. In some embodiments, the present disclosure provides methods for making an antibody or fragment thereof that is specific for SCF248. Exemplary antibodies and fragments that are specific for SCF248, as well as methods for making and using the antibodies and fragments, are provided in the present disclosure. In some embodiments, the antibodies and fragments thereof provided herein breaks the positive feedback loop between SCF248 expressed on various cell types and cKit+ immune cells, by binding to SCF248 and blocking the interaction between SCF248 and c-Kit.

Antibodies and Fragments

The present disclosure provides antibodies, including monoclonal antibodies, and fragments thereof. The antibody fragments provided herein that are specific for SCF (e.g., SCF248) are sometimes referred to herein as antigen-binding fragments, meaning that they comprise the portion of the parent antibody that is capable of binding the target antigen (SCF, e.g., SCF248). "Antibody fragment," "antigen binding fragment" and the like are used interchangeably herein. Examples of antibody fragments include Fab fragments, Fab' fragments, F (ab)' fragments, Fv fragments, isolated CDR regions, bispecific Fab dimers (Fab2), trispecific Fab trimers (Fab3), single chain Fv proteins ("scFv"), bis-scFv, (scFv) 2, minibodies, diabodies, triabodies, tetrabodies, disulfide stabilized Fv proteins ("dsFv"), single-domain antibodies (sdAb, nanobody), heavy-chain only antibodies (e.g., camelid VHH, camelid nanobody, shark Ig NAR), and portions of full length antibodies responsible for antigen binding.

A "Fab fragment" comprises one light chain and the $C_H1$ and variable regions of one heavy chain. The heavy chain of a Fab molecule cannot form a disulfide bond with another heavy chain molecule. A "Fab' fragment" comprises one light chain and a portion of one heavy chain that contains the VH domain and the $C_H1$ domain and also the region between the $C_H1$ and $C_H2$ domains, such that an interchain disulfide bond can be formed between the two heavy chains of two Fab' fragments to form an $F(ab')_2$ molecule. A "$F(ab')_2$ fragment" contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains. A "Fv fragment" comprises the variable regions from both the heavy and light chains, but lacks the constant regions. "scFvs" are Fv molecules in which the heavy and light chain variable regions have been connected by a flexible linker to form a single polypeptide chain, which forms an antigen binding region.

In some aspects, the antibodies and fragments thereof provided herein are defined by their complementary determining regions (CDRs). CDRs are part of the variable chains in antibodies; each of the light and heavy chain variable regions comprises three CDRs, CDR1, CDR2, and CDR3. The CDRs of an antibody determine antigen specificity. In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition and the contact definition.

The Kabat definition is a standard for numbering the residues in an antibody and is typically used to identify CDR regions. See, e.g., Johnson & Wu, Nucleic Acids Res., 28:214-8 (2000). The Chothia definition is similar to the Kabat definition, but the Chothia definition takes into account positions of certain structural loop regions. See, e.g., Chothia et al., J. Mol. Biol., 196:901-17 (1986); Chothia et al., Nature, 342:877-83 (1989). The AbM definition uses an integrated suite of computer programs produced by Oxford Molecular Group that model antibody structure. See, e.g., Martin et al., Proc Natl Acad Sci (USA), 86:9268-9272 (1989); "ABM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al., J. Mol. Biol., 5:732-45 (1996).

Antibodies and fragments thereof may also include recombinant polypeptides, fusion proteins, and bi-specific antibodies. The anti-SCF antibodies and fragments thereof disclosed herein may be of an IgG1, IgG2, IgG3, or IgG4 isotype. In one embodiment, the anti-SCF antibodies and fragments thereof disclosed herein are of an IgG1 or an IgG4 isotype. The anti-SCF antibodies and fragments thereof of the present invention may be derived from any species including, but not limited to, mouse, rat, rabbit, primate, llama, camel, goat, shark, chicken, and human. The SCF antibodies and fragments thereof may be chimeric, humanized, or fully human antibodies. In one embodiment, the anti-SCF antibodies are murine antibodies. In another embodiment, the anti-SCF antibodies are chimeric antibodies. In a further embodiment, the chimeric antibodies are mouse-human chimeric antibodies. In another embodiment, the antibodies are derived from mice and are humanized.

A "chimeric antibody" is an antibody having at least a portion of the heavy chain variable region and at least a portion of the light chain variable region derived from one species; and at least a portion of a constant region derived from another species. For example, in one embodiment, a chimeric antibody may comprise murine variable regions and a human constant region.

A "humanized antibody" is an antibody containing complementarity determining regions (CDRs) that are derived from a non-human antibody; and framework regions as well as constant regions that are derived from a human antibody. For example, the anti-SCF antibodies provided herein may comprise CDRs derived from one or more murine antibodies and human framework and constant regions. Thus, in one embodiment, the humanized antibody provided herein binds to the same epitope on SCF as the murine antibody from which the antibody's CDRs are derived.

In some embodiments, the antibodies and fragments thereof provided herein comprise a heavy and light chain, each of which comprises three CDRs. The amino acid sequences of exemplary heavy chain CDR1, CDR2, and CDR3 (HCDR1, HCDR2, and HCDR3, respectively) and light chain CDR1, CDR2, and CDR3 (LCDR1, LCDR2, and LCDR3, respectively) are provided below in Table 1. Table 1 also provides the amino acid sequences of exemplary heavy and light chain variable regions. In some embodiments, the present disclosure provides antibodies referred to herein as "5H10" and "2G8". The heavy chain variable regions of humanized 5H10 or 2G8 are referred to herein as VH1, VH2, VH3, VH4, and VH5. 5H10 VH0 is the variable heavy chain of the murine parent antibody generated via the methods described herein. VH1, VH2, VH3, VH4, and VH5 are each humanized heavy chain variable regions derived from 5H10 VH0 or 2G8 VH0. The 5H10 antibody comprises a kappa light chain. The murine parent antibody variable light chain is referred to herein as 5H10 VK0. VK1, VK2, VK3, and VK4 are each humanized light chain variable regions derived from VK0. The 2G8 antibody comprises a lambda light chain. The murine parent antibody variable light chain is referred to herein as 2G8 VL0. VL1, VL2, VL3, and VL4 are each humanized light chain variable regions derived from VL0.

TABLE 1

Exemplary anti-SCF antibody sequences

| SEQ ID NO | Description | |
|---|---|---|
| 1 | 5H10 Heavy chain CDR1 | SYWMN |
| 2 | 5H10 Heavy chain CDR2 | QIYPGDGDTHYNGKFKG |
| 3 | 5H10 Heavy chain CDR3 | SNWVGSY |
| 4 | 5H10 Light chain CDR1 | KSSQSLLESDGKTYLN |
| 5 | 5H10 Light chain CDR2 | LVSRLDS |
| 6 | 5H10 Light chain CDR3 | WQGTHLPQT |
| 7 | 5H10 Heavy chain variable region VH0 (murine parent) | QVQLQQSGAELVRPGSSVKISCKSSGYAFSSYWMNWVKQRPGQGLEWIGQIYPGDGDTHYNGKFKGKATLTADKSSSTAYMQLSRLTSEDSAVYFCSSSNWVGSYWGQGTLVTVSA |
| 8 | 5H10 Heavy chain variable region VH1 (humanized) | QVQLVQSGAELKKPGSSVKISCKSSGYAFSSYWMNWVKQRPGQGLEWIGQIYPGDGDTHYNGKFKGKATLTADKSTSTAYMELSSLTSEDSAVYFCSSSNWVGSYWGQGTLVTVSS |
| 9 | 5H10 Heavy chain variable region VH2 (humanized) | QVQLVQSGAEVKKPGSSVKISCKSSGYAFSSYWMNWVKQRPGQGLEWIGQIYPGDGDTHYNGKFKGKATLTADKSTSTAYMELSSLRSEDTAVYFCSSSNWVGSYWGQGTLVTVSS |
| 10 | 5H10 Heavy chain variable region VH3 (humanized) | QVQLVQSGAEVKKPGSSVKVSCKSSGYAFSSYWMNWVRQRPGQGLEWIGQIYPGDGDTHYNGKFKGKATLTADKSTSTAYMELSSLRSEDTAVYFCSSSNWVGSYWGQGTLVTVSS |
| 11 | 5H10 Heavy chain variable region VH4 (humanized) | QVQLVQSGAEVKKPGSSVKVSCKSSGYAFSSYWMNWVRQRPGQGLEWIGQIYPGDGDTHYNGKFKGRVTITADKSTSTAYMELSSLRSEDTAVYFCSSSNWVGSYWGQGTLVTVSS |
| 12 | 5H10 Heavy chain variable region VH5 (humanized) | QVQLVQSGAEVKKPGSSVKVSCKSSGYAFSSYWMNWVRQRPGQGLEWIGQIYPGDGDTHYNGKFQGRVTITADKSTSTAYMELSSLRSEDTAVYYCSSSNWVGSYWGQGTLVTVSS |
| 13 | 5H10 Light chain variable region VK0 (murine parent) | DVVMTQTPLTLSVTIGQTASISCKSSQSLLESDGKTYLNWLSQRPGQSPKRLIYLVSRLDSGVPDRFTGSGSGTDFTLKISRVEAEDLGVYYCWQGTHLPQTFGGGTKLEIK |
| 14 | 5H10 Light chain variable region VK1 (humanized) | DVVMTQSPLTLSVTLGQPASISCKSSQSLLESDGKTYLNWLQQRPGQSPRRLIYLVSRLDSGVPDRFTGSGSGTDFTLKISRVEAEDVGVYYCWQGTHLPQTFGGGTKVEIK |
| 15 | 5H10 Light chain variable region VK2 (humanized) | DVVMTQSPLSLPVTLGQPASISCKSSQSLLESDGKTYLNWLQQRPGQSPRRLIYLVSRLDSGVPDRFTGSGSGTDFTLKISRVEAEDVGVYYCWQGTHLPQTFGGGTKVEIK |
| 16 | 5H10 Light chain variable region VK3 (humanized) | DVVMTQSPLSLPVTLGQPASISCKSSQSLLESDGKTYLNWLQQRPGQSPRRLIYLVSRLDSGVPDRFSGSGSGTDFTLKISRVEAEDVGVYYCWQGTHLPQTFGGGTKVEIK |
| 17 | 5H10 Light chain variable region VK4 (humanized) | DVVMTQSPLSLPVTLGQPASISCKSSQSLLESDGKTYLNWFQQRPGQSPRRLIYLVSRLDSGVPDRFSGSGSGTDFTLKISRVEAEDVGVYYCWQGTHLPQTFGGGTKVEIK |
| 37 | 5H10 VH5 CDR2 | QIYPGDGDTHYNGKFQG |

The skilled person will understand that the variable heavy and variable light chains may be independently selected, or mixed and matched, from the antibodies provided herein. Thus, in some embodiments, the antibodies and fragments thereof provided herein comprise heavy and light chain combinations selected from the group consisting of VH0/VK0, VH0/VK1, VH0/VK2, VH0/VK3, VH0/VK4, VH1/VK0, VH1/VK1, VH1/VK2, VH1/VK3, VH1/VK4, VH2/VK0, VH2/VK1, VH2/VK2, VH2/VK3, VH2/VK4, VH3/VK0, VH3/VK1, VH3/VK2, VH3/VK3, VH3/VK4, VH4/VK0, VH4/VK1, VH4/VK2, VH4/VK3, VH4/VK4, VH5/VK0, VH5/VK1, VH5/VK2, VH5/VK3, and VH5/VK4.

In some embodiments, the present disclosure provides antibodies or fragments comprising amino acid sequences having at least 80%, at least 85%, at least 90%, at least 95%, or at least 99% homology to an amino acid sequence selected from the group consisting of SEQ ID NOs: 7-12. In some embodiments, the present disclosure provides antibodies or fragments thereof comprising a heavy chain variable region according to a sequence selected from the group consisting of SEQ ID NOs: 7-12. In some embodiments, the present disclosure provides antibodies or fragments comprising amino acid sequences having at least 80%, at least 85%, at least 90%, at least 95%, or at least 99% homology to an amino acid sequence selected from the group consisting of SEQ ID NOs: 7-11, wherein the antibody or fragment comprises a heavy chain CDR1, CDR2, and CDR3 identical to SEQ ID NOs: 1, 2, and 3, respectively. In some embodiments, the present disclosure provides antibodies or fragments comprising amino acid sequences having at least 80%, at least 85%, at least 90%, at least 95%, or at least 99% homology to an amino acid sequence of SEQ ID NO: 12, wherein the antibody or fragment comprises a heavy chain CDR1, CDR2, and CDR3 identical to SEQ ID NOs: 1, 37, and 3, respectively.

In some embodiments, the present disclosure provides antibodies or fragments comprising amino acid sequences having at least 80%, at least 85%, at least 90%, at least 95%, or at least 99% homology to an amino acid sequence selected from the group consisting of SEQ ID NOs: 13-17. In some embodiments, the present disclosure provides antibodies or fragments thereof comprising a light chain variable region according to a sequence selected from the group consisting of SEQ ID NOs: 13-17. In some embodiments, the present disclosure provides antibodies or fragments comprising amino acid sequences having at least 80%, at least 85%, at least 90%, at least 95%, or at least 99% homology to an amino acid sequence selected from the group consisting of SEQ ID NOs: 13-17, wherein the antibody or fragment comprises a light chain CDR1, CDR2, and CDR3 identical to SEQ ID NOs: 4, 5, and 6, respectively.

In some embodiments, the present disclosure provides antibodies or fragments comprising amino acid sequences having at least 80%, at least 85%, at least 90%, at least 95%, or at least 99% homology to: SEQ ID NO: 7 and SEQ ID NO: 13; SEQ ID NO: 7 and SEQ ID NO: 14; SEQ ID NO: 7 and SEQ ID NO: 15; SEQ ID NO: 7 and SEQ ID NO: 16; SEQ ID NO: 7 and SEQ ID NO: 17; SEQ ID NO: 7 and SEQ ID NO: 13; SEQ ID NO: 7 and SEQ ID NO: 14; SEQ ID NO: 7 and SEQ ID NO: 15; SEQ ID NO: 7 and SEQ ID NO: 16; SEQ ID NO: 7 and SEQ ID NO: 17; SEQ ID NO: 8 and SEQ ID NO: 13; SEQ ID NO: 8 and SEQ ID NO: 14; SEQ ID NO: 8 and SEQ ID NO: 15; SEQ ID NO: 8 and SEQ ID NO: 16; SEQ ID NO: 8 and SEQ ID NO: 17; SEQ ID NO: 9 and SEQ ID NO: 13; SEQ ID NO: 9 and SEQ ID NO: 14; SEQ ID NO: 9 and SEQ ID NO: 15; SEQ ID NO: 9 and SEQ ID NO: 16; SEQ ID NO: 9 and SEQ ID NO: 17; SEQ ID NO: 10 and SEQ ID NO: 13; SEQ ID NO: 10 and SEQ ID NO: 14; SEQ ID NO: 10 and SEQ ID NO: 15; SEQ ID NO: 10 and SEQ ID NO: 16; SEQ ID NO: 10 and SEQ ID NO: 17; SEQ ID NO: 11 and SEQ ID NO: 13; SEQ ID NO: 11 and SEQ ID NO: 14; SEQ ID NO: 11 and SEQ ID NO: 15; SEQ ID NO: 11 and SEQ ID NO: 16; SEQ ID NO: 11 and SEQ ID NO: 17; SEQ ID NO: 12 and SEQ ID NO: 13; SEQ ID NO: 12 and SEQ ID NO: 14; SEQ ID NO: 12 and SEQ ID NO: 15; SEQ ID NO: 12 and SEQ ID NO: 16; or SEQ ID NO: 12 and SEQ ID NO: 17.

In particular embodiments, the antibodies and fragments thereof comprise heavy and light chain combinations selected from the group consisting of VH1/VK1, VH1/VK2, VH1/VK3, VH2/VK1, VH2/VK2, VH2/VK3, VH3/VK1, VH3/VK2, VH3/VK3, VH4/VK1, VH4/VK2, VH4/VK3, VH5/VK1, VH5/VK2, and VH5/VK3. In some embodiments, the antibodies comprise an amino acid sequence having at least 80%, at least 85%, at least 90%, at least 95%, or at least 99% sequence identity to SEQ ID NO: 8 or SEQ ID NO: 9; and an amino acid sequence having at least 80%, at least 85%, at least 90%, at least 95%, or at least 99% sequence identity to SEQ ID NO: 16. In some embodiments, the antibody, or fragment thereof, comprises an amino acid sequence having at least 80%, at least 85%, at least 90%, at least 95%, or at least 99% sequence identity to SEQ ID NO: 8 or SEQ ID NO: 9; and an amino acid sequence having at least 80%, at least 85%, at least 90%, at least 95%, or at least 99% sequence identity to SEQ ID NO: 16; wherein the antibody or fragment comprises a heavy chain CDR1, CDR2, and CDR3 identical to SEQ ID NOs: 1, 2, and 3, respectively, and a light chain CDR1, CDR2, and CDR3 identical to SEQ ID NOs: 4, 5, and 6, respectively. In some embodiments, the antibody, or fragment thereof, comprises an amino acid sequence having at least 95% or at least 99% sequence identity to SEQ ID NO: 8 or SEQ ID NO: 9; and an amino acid sequence having at least 95% or at least 99% sequence identity to SEQ ID NO: 16; wherein the antibody or fragment comprises a heavy chain CDR1, CDR2, and CDR3 identical to SEQ ID NOs: 1, 2, and 3, respectively, and a light chain CDR1, CDR2, and CDR3 identical to SEQ ID NOs: 4, 5, and 6, respectively. The antibody or fragment thereof may specifically bind to SCF248 but may not bind to SCF220. In some embodiments, the antibodies comprise a heavy chain variable region according to SEQ ID NO: 8 and a light chain variable region according to SEQ ID NO: 16. In some embodiments, the antibodies comprise a heavy chain variable region according to SEQ ID NO: 9 and a light chain variable region according to SEQ ID NO: 16.

In some embodiments, the antibodies and fragments provided herein comprise a heavy chain variable region amino acid sequence according to SEQ ID NO: 7, 8, 9, 10, 11, or 12, or a variant thereof; and/or comprise a light chain variable region amino acid sequence according to SEQ ID NO: 13, 14, 15, 16, or 17, or a variant thereof. Variants may comprise 1, 2, 3, 4, 5, 6, 7, 8, 9, or 10 amino acid substitutions or deletions, or a combination thereof. In some embodiments, the amino acid substitutions are conservative substitutions. The anti-SCF antibodies disclosed herein having one or more amino acid substitution, insertion, deletion, or combination thereof in the CDR or variable light or heavy chain region retain the biological activity of the corresponding anti-SCF antibody that does not have an amino acid substitution, insertion, or deletion relative to the sequences provided herein. Thus, the variant anti-SCF antibodies provided herein retain specific binding to SCF248. The terms percent homology, sequence identity, sequence homology, and the like are used interchangeably herein and refer to the number of identical amino acid sequences shared by two reference sequences, divided by the total number of amino acid positions, multiplied by 100.

In some embodiments, the present invention provides antibodies that bind to the same epitope as any one of the exemplary antibodies disclosed herein. Thus, in some embodiments, the present invention provides antibodies that compete for binding to SCF with the exemplary antibodies provided herein. For example, in some embodiments, the present disclosure provides antibodies that specifically bind to a region of the amino acid sequence provided herein as SEQ ID NO: 29. In some embodiments, antibodies provided herein specifically bind to an epitope comprising the amino acid sequence of SEQ ID NO: 33 (ASSLRNDSSSSNRK) or SEQ ID NO: 36 ASSLRNDSSSSNR). In some embodiments, the present disclosure provides antibodies that specifically bind to an epitope consisting of an amino acid sequence according to SEQ ID NO: 33 or SEQ ID NO: 36. In some embodiments, the present disclosure provides antibodies that specifically bind to an epitope comprising at least 5, at least 6, at least 7, at least 8, at least 9, or at least 10 contiguous amino acids of SEQ ID NO: 33.

In some embodiments, the antibodies and fragments thereof provided herein comprise the HCDR1, HCDR2, HCDR3, LCDR1, LCDR2, and/or LCDR3 of the heavy and light chain variable regions provided herein, or variants thereof. Thus, in some embodiments, the antibodies and fragments thereof provided herein include antibodies wherein the HCDRs are the HCDRs of SEQ ID NO: 7, 8, 9, 10, 11, or 12; and/or wherein the LCDRs are the LCDRs of SEQ ID NOs: 13, 14, 15, 16, or 17. For example, in some embodiments, the antibodies and fragments thereof comprise amino acids 31-35, 50-65, and 95-102 of any one of the heavy chain variable regions provided herein, as defined by the Kabat numbering scheme. In some embodiments, the antibodies and fragments thereof comprise amino acids 24-34, 50-56, and 89-97 of any one of the light chain variable regions provided herein, as defined by the Kabat numbering scheme.

Exemplary humanized antibodies are provided herein. Additional anti-SCF antibodies comprising the heavy and light chain CDRs provided herein, or variants thereof, may be generated using any human framework sequence, and are also encompassed in the present invention. In one embodiment, framework sequences suitable for use in the present invention include those framework sequences that are structurally similar to the framework sequences provided herein. Further modifications in the framework regions may be made to improve the properties of the antibodies provided herein. Such further framework modifications may include chemical modifications; point mutations to reduce immunogenicity or remove T cell epitopes; or back mutation to the residue in the original germline sequence.

In some embodiments, such framework modifications include those corresponding to the mutations exemplified herein, including backmutations to the germline sequence. For example, in one embodiment, one or more amino acids in the human framework regions of the VH and/or VL of the humanized antibodies provided herein are back mutated to the corresponding amino acid in the parent murine antibody. The present invention also encompasses humanized antibodies that bind to SCF (e.g., SCF248) and comprise framework modifications corresponding to the exemplary modifications described herein with respect to any suitable framework sequence, as well as other framework modifications that otherwise improve the properties of the antibodies.

In other embodiments, the antibodies provided herein comprise one or more mutations to improve stability, improve solubility, alter glycosylation, and/or reduce immunogenicity, such as, for example, by targeted amino acid changes that reduce deamidation or oxidation, reduce isomerization, optimize the hydrophobic core and/or charge cluster residues, remove hydrophobic surface residues, optimize residues involved in the interface between the variable heavy and variable light chains, and/or modify the isoelectric point.

The anti-SCF antibodies and fragments thereof provided herein may further comprise Fc region modifications to alter effector functions. Fc modifications may be amino acid insertions, deletions, or substitutions, or may be chemical modifications. For example, Fc region modifications may be made to increase or decrease complement binding, to increase or decrease antibody-dependent cellular cytotoxicity, or to increase or decrease the half-life of the antibody. Some Fc modifications increase or decrease the affinity of the antibody for an Fcγ receptor such as FcγRI, FcγRII, FcγRIII, or FcRn. Various Fc modifications have been described in the art, for example, in Shields et al., *J Biol. Chem* 276; 6591 (2001); Tai et al. *Blood* 119; 2074 (2012); Spiekermann et al. *J Exp. Med* 196; 303 (2002); Moore et al. *mAbs* 2:2; 181 (2010); Medzihradsky *Methods in Molecular Biology* 446; 293 (2008); Mannan et al. *Drug Metabolism and Disposition* 35; 86 (2007); and Idusogie et al. *J Immunol* 164; 4178 (2000). In some embodiments, Fc region glycosylation patters are altered. In other embodiments, the Fc region is modified by pegylation (e.g., by reacting the antibody or fragment thereof with polyethylene glycol (PEG). Exemplary Fc modifications include modifications at one or more amino acid position selected from the group consisting of 228, 233, 234, 235, 236, 241, 248, 265, 297, 309, 331, and 409 (Kabat numbering; Kabat et al., Sequences of Immunological Interest, Fifth Edition, National Institute of Health, Bethesda, Md. (1991)). In embodiments, the antibody has modifications to reduce or abolish effector function. In embodiments, the antibody is an IgG1 antibody having one or more Fc modification selected from the group consisting of E233P, L234V, L234A, L235V, L235A, G236 (deleted), D265A, D270A, N297A and N297Q. In embodiments, the antibody is an IgG4 antibody having one or more Fc modification selected from the group consisting of S228P, E233P, F234A, F234V, L235A, L235V, S241P, L248E, D265A, D265T, L309L, and R409K. In embodiments, the anti-SCF antibodies provided herein comprise a S241P mutation and an L248E mutation.

In embodiments, the present disclosure provides antibodies provided herein that comprise a human IgG4 constant region according to SEQ ID NOs: 40 and 41. In embodiments, the present disclosure provides antibodies comprising at least about 80%, at least about 85%, at least about 90%, at least about 95%, or about 99% sequence identity to SEQ ID NO: 40, 41, 42, 43, 44, 45, 46, 47, 48, 49, or 50. In embodiments, the present disclosure provides antibodies comprising a heavy chain according to SEQ ID NO: 40 and a light chain according to SEQ ID NO: 41. In embodiments, the present disclosure provides antibodies comprising a heavy chain according to SEQ ID NO: 42, 43, 44, 45, or 46 and a light chain according to SEQ ID NO: 47, 48, 49, or 50. In embodiments, the present disclosure provides an antibody comprising a heavy chain according to SEQ ID NO: 42 and a light chain according to SEQ ID NO: 49. In embodiments, the present disclosure provides an antibody comprising a heavy chain according to SEQ ID NO: 43 and a light chain according to SEQ ID NO: 49. In embodiments, the present disclosure provides an antibody comprising a heavy chain according to SEQ ID NO: 44 and a light chain according to SEQ ID NO: 49. In embodiments, the present disclosure provides an antibody comprising a heavy chain according to SEQ ID NO: 45 and a light chain according to SEQ ID NO: 49. In embodiments, the present disclosure provides an antibody comprising a heavy chain according to SEQ ID NO: 46 and a light chain according to SEQ ID NO: 49.

In some embodiments, the present disclosure provides methods for making antibodies that specifically bind to SCF248. The SCF248 isoform of SCF include exon 6, which comprises a cleavage site between two alanine residues (amino acids 16 and 17 of SEQ ID NO: 34, which provides the amino acid sequence of exon 6). Previous anti-SCF antibodies were generated by immunizing mice with a peptide spanning exon 6 and part of Exon 7 (see, e.g., U.S. Pat. No. 8,911,729, which is hereby incorporated by reference in its entirety for all purposes). Since SCF220 is associated with homeostatic activities, any cross-reactivity with SCF220 would be detrimental as it would result in various off-target effects in subjects. Advantageously, the antibodies provided in the present disclosure bind to SCF248 with very high specificity. In some embodiments, the antibodies provided herein are specific for SCF248 and do not bind to SCF220. Thus, the antibodies provided herein are capable of specifically inhibiting the interaction between SCF248 and c-Kit that induces and perpetuates chronic inflammatory responses and fibrosis. Moreover, the antibodies provided herein are capable of specifically inducing the internalization of SCF and thereby reducing the interaction between SCF248 and c-Kit. Accordingly, in some embodiments the present disclosure provides antibodies that are specific for SCF248 and are safe and effective in various inflammatory and fibrotic diseases discussed herein and known in the art.

For preparation of monoclonal antibodies, any technique that provides for the production of antibody molecules by continuous cell lines in culture may be used (see e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein and the trioma technique, the human B-cell hybridoma technique (See, e.g., Kozbor et al., Immunol. Today, 4:72 (1983)), and the EBV-hybridoma technique to produce human monoclonal antibodies (Cole et al., in Monoclonal Antibodies and Cancer Therapy, Alan R. Liss, Inc., pp. 77-96 (1985)). Alternatively, the antibodies may be made by recombinant DNA methods. In some embodiments, antibodies in accordance with the present disclosure may be made by isolating monoclonal antibodies from phage display libraries using the techniques described, for example, in Clackson et al., *Nature* 352:624-28 (1991) and Marks et al., *J. Mol. Biol.* 222(3): 581-97 (1991). In some embodiments, the antibodies are fully human antibodies constructed by combining Fv clone variable domain sequence(s) selected from human-derived phage display or yeast display libraries with known human constant domain sequence(s).

In some embodiments provided herein, the antibodies are prepared from a hybridoma. Using the hybridoma method, a mouse, hamster, or other appropriate host animal, is immunized by injecting an immunizing peptide to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated in vitro (e.g., in culture) using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

In some embodiments, the antibodies provided herein are generated using the murine hybridoma system. Hybridoma production in the mouse is a well-established procedure. Immunization protocols and techniques for isolation of immunized splenocytes for fusion are known in the art. Fusion partners (e.g., murine myeloma cells) and fusion procedures are also known. Embodiments of the technology herein provide antibodies (e.g., monoclonal antibodies) produced from a hybridoma prepared by immunizing mice with a peptide that is a portion or fragment of the SCF protein.

In some embodiments, the antibodies specific for SCF248 provided herein are generated by immunizing mice with a peptide having an amino acid sequence that is largely or exclusively within exon 6. For example, the immunizing peptide comprises any stretch of 5 or more amino acids within SEQ ID NO: 34. As another example, the immunizing peptide comprises any stretch of 5 or more amino acids beginning at amino acid position 20 of SEQ ID NO: 29. As another example, the immunizing peptide comprises a stretch of 5 or more amino acids beginning at amino acid position 20 of SEQ ID NO: 29 and ending at any one of positions 25 to 38 of SEQ ID NO: 29. Thus, in some embodiments, the immunizing peptide comprises the amino acid sequence of exon 6 after the cleavage site, and is either fully contained within exon 6 or comprises only 1, 2, 3, 4, or 5 amino acids of exon 7. In some embodiments, the immunizing peptide comprises or consists of SEQ ID NO: 30. In some embodiments, the immunizing peptide comprises any of the peptides provided herein or conservative variants thereof. Conservative variants may comprise 1, 2, 3, 4, or 5 amino acid substitutions or deletions, or a combination thereof. As provided above, in some embodiments, the antibodies generated using the immunizing peptides provided herein have an epitope that falls entirely or largely within exon 6. By "largely within" it is meant that at least 75%, at least 80%, at least 85%, at least 90%, or at least 95% of the peptide falls within exon 6. In some embodiments, the epitope begins at the cleavage site of exon 6 (i.e., between the alanines at amino acid positions 19 and 20 of SEQ ID NO: 29 and extends to the end of exon 6. In some embodiments, the epitope begins at the cleavage site of exon 6 and extends to the $1^{st}$, $2^{nd}$, $3^{rd}$, $4^{th}$ or $5^{th}$ n-terminal amino acid of the transmembrane domain. In some embodiments, the epitope comprises or consists of SEQ ID NO: 33. In some embodiments, the antibody referred to herein as 5H10 (including the murine, chimeric, and humanized 5H10 antibodies) binds to an epitope of SCF comprising or consisting of SEQ ID NO: 33.

In some embodiments, the methods provided herein were used to generate antibodies referred to herein as 5H10. In some embodiments, the antibody "5H10" is also referred to herein as "OpSCF." Antibody 5H10 advantageously binds SCF248 with high specificity and does not bind SCF220. The amino acid sequences of the murine parent antibody 5H10, as well as humanized variants thereof, are provided herein (see, Table 1).

In one embodiment, the present invention provides bispecific or multispecific antibodies specific for SCF and at least one other antigen or epitope. The anti-SCF antibodies and fragments thereof provided herein may be tested for binding to SCF using the binding assays provided herein, or any other binding assay known in the art.

Unless otherwise stated, the practice of the present invention employs conventional molecular biology, cell biology, biochemistry, and immunology techniques that are well known in the art and described, for example, in Methods in Molecular Biology, Humana Press; Molecular Cloning: A Laboratory Manual, second edition (Sambrook et al., 1989), Current Protocols in Immunology (J. E. Coligan et al., eds., 1991); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Phage display: a laboratory manual (C. Barbas III et al, Cold Spring Harbor Laboratory Press, 2001); and Using antibodies: a laboratory manual (E. Harlow and D. Lane (Cold Spring Harbor Laboratory Press, 1999).

Methods of Treatment

In one aspect, the present disclosure provides methods for treating and/or preventing any disease or condition associated with immune cell migration, activation, and/or proliferation via interaction of SCF248 with c-Kit on immune cells. Thus, in some embodiments, the present disclosure provides methods for inhibiting or preventing activation of immune cells; as well as reducing or preventing the accumulation of immune cells within organs or tissues, thereby treating or preventing various diseases and disorders that involve inflammation. In some embodiments, the immune cells are selected from the group consisting of mast cells, innate lymphoid cells (ILCs, such as ILC2 or ILC3 cells), and eosinophils.

As used herein, the terms "treatment" or "treating" refers to both therapeutic treatment and prophylactic or preventive measures. Subjects in need of treatment include those subjects that already have the disease or condition, as well as those that may develop the disease or condition and in whom the object is to prevent, delay, or diminish the disease or condition. As used herein, the term "subject" denotes a mammal, such as a rodent, a feline, a canine, and a primate. Preferably, a subject according to the invention is a human. The term "therapeutically effective amount," as used herein, refers to the amount of a compound or composition that is necessary to provide a therapeutic and/or preventative benefit to the subject.

In one aspect the present invention provides methods for treating a subject for an inflammatory disease, a fibrotic disease, and/or a tissue remodeling disease. In some embodiments, the inflammatory disease is a chronic inflammatory disease.

Chronic inflammatory, fibrotic, and tissue remodeling diseases include diseases of the lung, kidney, liver, heart, skin, connective tissue, and other tissues. Exemplary inflammatory, fibrotic or tissue remodeling diseases include, without limitation, pulmonary fibrosis (e.g., idiopathic pulmonary fibrosis (IPF), scleroderma lung fibrosis, scleroderma-related interstitial lung disease (SSc-ILD), pulmonary fibrosis associated with a lung infection or pneumonia, pulmonary fibrosis associated with systemic lupus erythematosus and/or rheumatoid arthritis, sarcoidosis), chronic obstructive pulmonary disease (COPD), acute respiratory distress syndrome (ARDS), cystic fibrosis, peribronchial fibrosis, bleomycin lung, hypersensitivity pneumonitis, asthma, fibrothorax, mediastinal fibrosis, chronic rhinosinusitis, urticaria (e.g., chronic spontaneous urticaria), atopic dermatitis, dermatomyositis, nodular subepidermal fibrosis, scleroderma, keloid, renal fibrosis, chronic kidney disease, glomerulonephritis, chronic renal allograft rejection, nephropathy (e.g., IgA nephropathy, focal segmental glomerulosclerosis, rapidly progressive glomerulonephritis, crescentic glomerulonephritis, lupus nephritis, hypertensive nephropathy, or diabetic nephropathy), non-alcoholic steatohepatitis (NASH), liver cirrhosis, hepatic fibrosis, primary sclerosing cholangitis, primary biliary cirrhosis, fibromyalgia, gingival fibrosis, radiation-induced fibrosis, eosinophilic esophagitis, arthrofibrosis, and atrial fibrosis, endomyocardial fibrosis, parenchymal fibrosis, fibrous histocytoma, or glial scarring.

In some embodiments, the antibodies and fragments thereof disclosed herein may be administered to the subject by at least one route selected from parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intratympanic, intrauterine, intravesical, intravitreal, bolus, subconjunctival, oral, vaginal, rectal, buccal, sublingual, intranasal, intratumoral, and transdermal.

In embodiments, the antibodies and fragments thereof disclosed herein may be administered to a subject in need thereof in combination with one or more additional therapy. The one or more additional therapy may be a procedure such as a surgical procedure, or may be a therapeutic agent, such as an agent designed to mitigate or reduce symptoms of a disease or disorder associated with fibrosis and/or inflammation.

The present invention is further illustrated by reference to the following Examples. However, it should be noted that these Examples, like the embodiments described above, are illustrative and are not to be construed as restricting the scope of the invention in any way.

EXAMPLES

The following examples are given for the purpose of illustrating various embodiments of the disclosure and are not meant to limit the present disclosure in any fashion. Changes therein and other uses which are encompassed within the spirit of the disclosure, as defined by the scope of the claims, will be recognized by those skilled in the art.

An overview of the tissue injury/disease process is summarized in FIG. 1. A disease process initiates inflammation. c-Kit+ immune cells produce cytokines that cause fibroblasts to change into activated myofibroblasts which express SCF248 on their surface. The expression of SCF248 on the surface of myofibroblasts and other cells activates more immune cells, resulting in cytokine release of IL-4, IL-9, IL-13, IL-25, TGFβ, and other cytokines, perpetuating inflammation. Myofibroblasts secrete extracellular matrix proteins, collagen, and fibronectin, leading to fibrosis and remodeling diseases such as pulmonary fibrosis, skin fibrosis, severe asthma, and other diseases.

Figure 2:
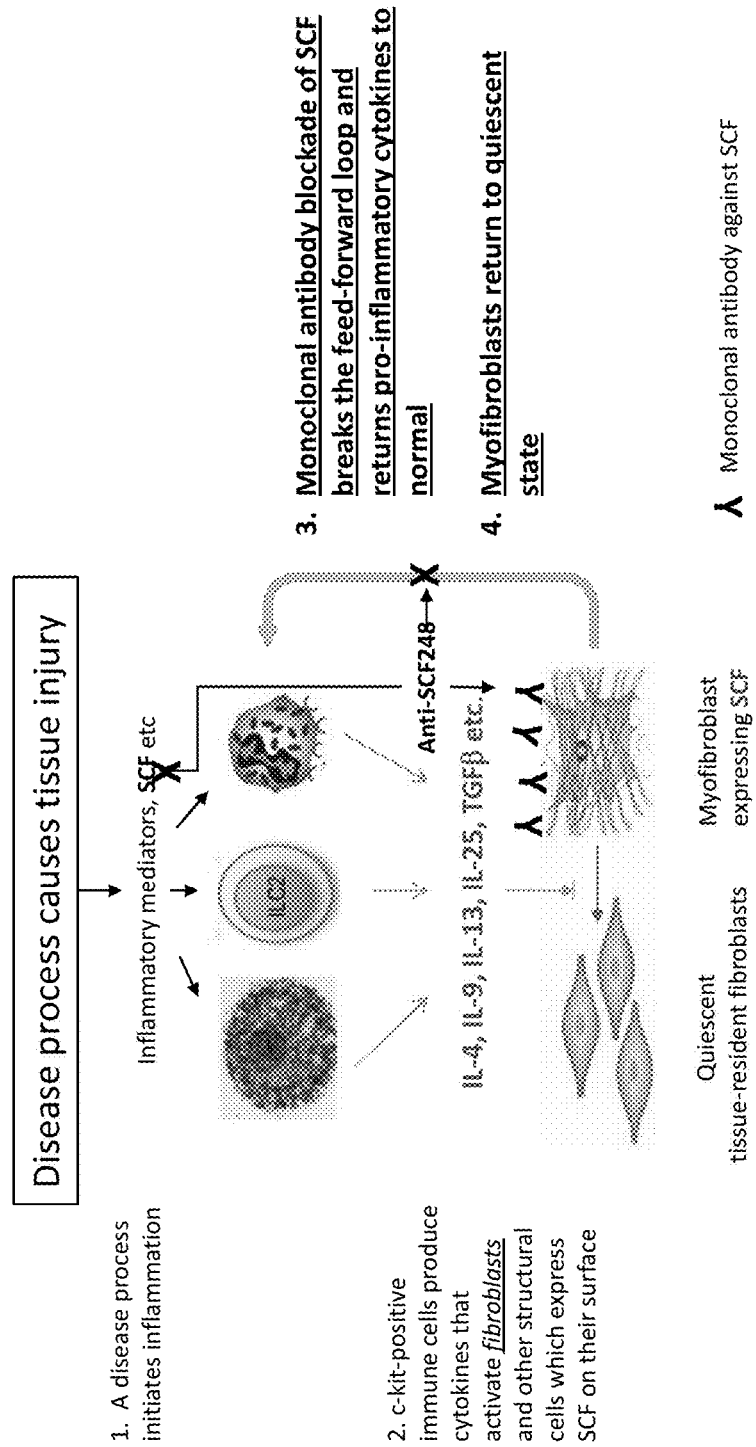
FIG. 2 shows an exemplary mechanism of an anti-SCF248 antibody of the instant disclosure, 5H10.

An exemplary mechanism of an antibody of the instant disclosure which targets SCF248 (said antibody referred to herein as OpSCF and/or as 5H10) is summarized in FIG. 2.

As provided above, SCF has two isoforms which result from alternative splicing: SCF248 and SCF220. SCF248 and SCF220 differ by exon 6. SCF220 is associated with homeostatic functions, and SCF248 is associated with inflammation and fibrosis. SCF248 activates immune cells during inflammation and is sometimes called "soluble SCF." SCF248 is expressed on various cell types including myofibroblasts, activated epithelia, endothelia, macrophages, eosinophils, mast cells, and monocytes (FIG. 3). The SCF248 isoform results in cleavage of monomeric cleaved extracellular domain, called SCF165. The amino acid sequence of exon 6 is provided herein as SEQ ID NO: 34.

Example 1: Production of Anti-SCF mAbs Utilizing Hybridoma Technology

A peptide comprising ASSLRNDSSSSNRKAKNPPGD (SEQ ID NO: 30) was used to generate antibodies that bind to SCF248. The immunization peptide comprised a portion of exon 6, i.e. the SCF248 isoform of stem cell factor. In particular, the immunization peptide comprised a portion of exon 6 that begins after a cleavage site as defined herein. Mice were immunized with a peptide according to SEQ ID NO: 30 with a standard protocol. The determination of high titer serum antibodies indicated the appropriate immunization and fusion hybridomas were made. Culture supernatants were analyzed from individual clones for SCF-specific antibodies and chosen based upon specificity. Hybridomas producing specific monoclonal antibodies against the peptide were propagated and the monoclonal with the highest titer was subsequently tested in biologically relevant cultures. Antibody 5H10 had high specificity for SCF248 and no cross-reactivity with SCF220. No other monoclonal antibodies produced by the hybridomas had high specificity for SCF248 without cross-reactivity with SCF220. Thus, 5H10 was selected for further characterization, development, and chimerization and subsequent humanization.

Example 2. 5H10 Binding to SCF248 Complete Extracellular Domain

Figure 4A:
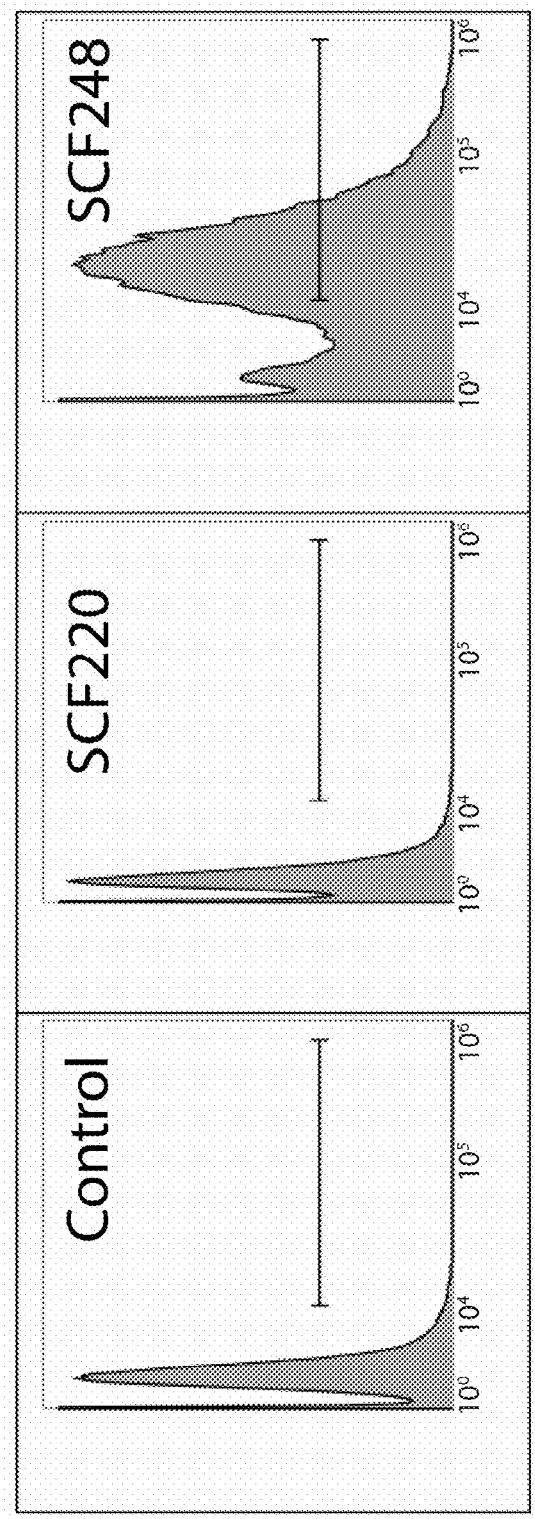
FIG. 4A is a set of histograms showing the binding of murine 5H10 antibody to control cells that do not expression SCF (left panel), cells that express SCF220 but not SCF248 (middle panel), and cells that express SCF248 but not SCF220 (right panel).

The murine 5H10 antibody obtained as described in Example 1 was directly conjugated with a fluorescent marker and the labeled antibody was incubated with Sl/Sl4 hSCF248 cells, which express SCF248; Sl/Sl4 hSCF220 cells, which express SCF220; or control cells that do not express SCF. Binding of the labeled antibody to the cells was assessed by flow cytometry. The specificity of 5H10 for SCF248 and lack of crossreactivity with SCF220 is shown in FIG. 4A.

Figure 4B:
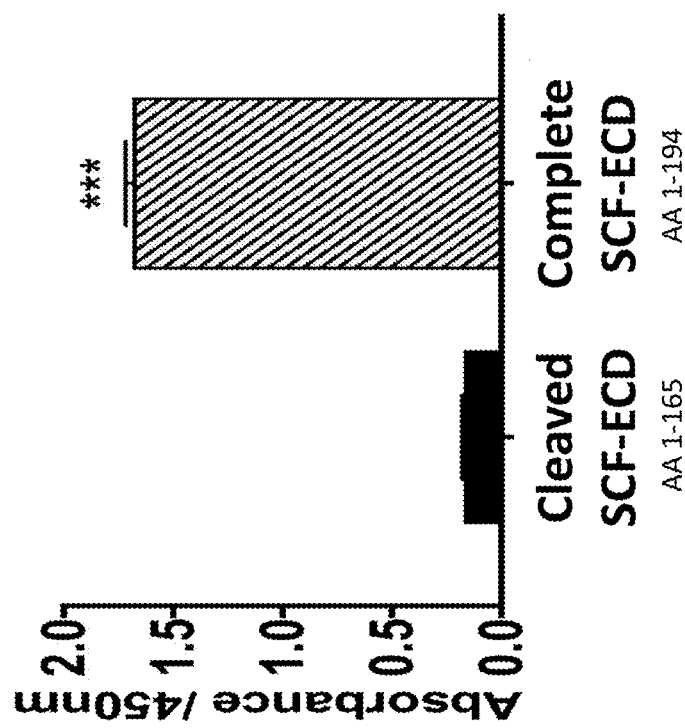
FIG. 4B shows the binding of murine 5H10 antibody to the 165 amino acid cleaved SCF extracellular domain (ECD) versus the complete 194 amino acid SCF ECD.

Binding of the murine 5H10 antibody to the cleaved extracellular domain (ECD) containing only amino acids 1-165 of SCF, vs the complete ECD containing amino acids 1-194 of SCF, was assessed by an ELISA method. The antibody bound to the complete SCF ECD but not to the cleaved SCF ECD (FIG. 4B), demonstrating that the antibody is specific for the complete extracellular domain and does not bind to the monomeric cleaved ECD that circulates in blood.

Figure 5:
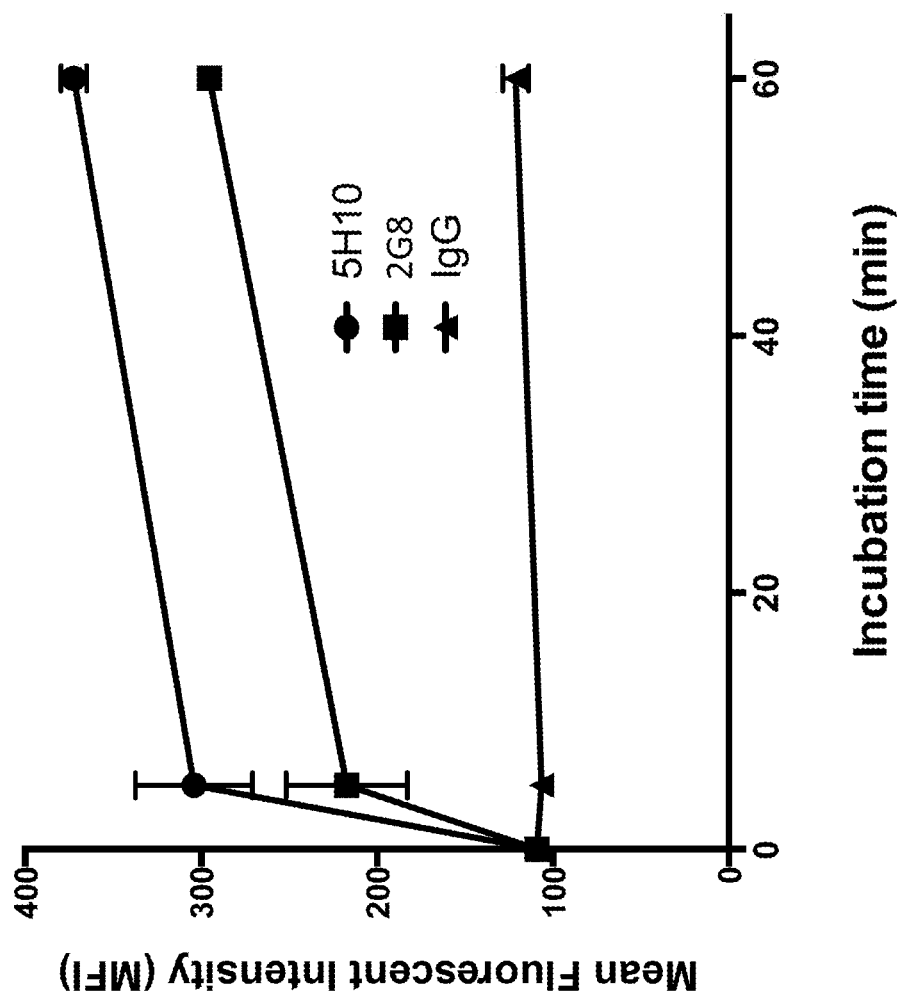
FIG. 5 shows the mean fluorescence intensity (MFI) as measured by flow cytometry after contacting cultured human IPF myofibroblasts with 2G8, 5H10, or control IgG antibodies, each of which are labeled with a red dye (PHRODO™).

To assess the ability of 2G8 and 5H10 antibodies to internalize SCF248 on myofibroblasts, antibodies were labeled with a red dye (PHRODO™), which is colorless at neutral pH and fluoresces red at the low pH within an endosome. Labeled antibodies were incubated with cultured human IPF myofibroblasts for 45 minutes and red fluorescence was visualized by microscopy. As shown in FIG. 5, the dye-labeled antibodies, but not control IgG, were rapidly internalized. 5H10 was internalized more rapidly and resulted in higher fluorescence compared to 2G8.

SCF triggers c-kit to signal by two distinct pathways: the MEK/ERK pathway and the P13K/AKT pathway. A study was conducted to determine whether the murine 5H10 antibody inhibits intracellular signaling in c-kit positive cells in either or both of these pathways. Eosinophils were incubated with SCF248-expressing cell lines, in the presence of either 5H10 or IgG control, and phospho-protein expression was measured with a BIO-RAD® BIO-PLEX® assay system. 5H10 significantly decreased the phospho-MEK and phosphor-AKT levels, indicating that the antibody significantly reduced c-kit mediated intracellular signaling (FIG. 6).

Taken together, the results of these studies indicated that antibody 5H10 binds specifically to and internalizes SCF248, and does not cross-react with the SCF220 isoform or the cleaved ECD. Moreover, 5H10 significantly inhibits the intracellular signaling pathways in c-kit positive cells that perpetuate inflammation.

Example 3. Humanization of Murine Antibody 5H10

Chimeric antibodies derived from 5H10 were produced by subcloning the variable domains of the heavy and light chains into a vector with a human IgG4 backbone. Chimeric antibodies were expressed and purified using standard protocols. 2G8 is a previously developed antibody that binds to SCF248 and SCF220, and contains a lambda light chain. The chimeric heavy and light chains of 2G8 were named VH0 and VL0, respectively. 5H10, the SCF248-specific antibody provided herein, contains a kappa light chain. The chimeric heavy and light chains of 5H10 were named VH0 and VK0, respectively.

The chimeric antibodies were humanized. Humanized heavy chains retained the same complementarity-determining regions (CDRs) but more "human-like" framework regions, and several humanized variants of each of 2G8 and 5H10 variable heavy chains, referred to herein as VH1, VH2, VH3, VH4, and VH5, were generated. Humanized kappa light chain variants of 5H10, referred to herein as VK1, VK2, VK3, and VK4, were also generated. Humanized lambda light chains of 2G8 were named VL1, VL2, VL3, and VL4. The 2G8 and 5H10 combinations of chimeric and humanized light chains and heavy chains tested are shown in Table 2 and Table 3, respectively. As shown in Table 2, certain heavy and light chain combinations of the 5H10 antibody variants resulted in high binding to hSCF248. Binding data used to determine the binding score are provided below in Example 5.

TABLE 2

Binding score for 2G8 chimeric and humanized clones to Sl/Sl4 hSCF248 cells

| 2G8 mAb | Binding Score |
| --- | --- |
| VH0/VL0 | high |
| VH1/VL1 | Moderate high |
| VH1/VL3 | moderate |
| VH1/VL4 | Moderate |
| VH2/VL1 | Moderate |
| VH2/VL4 | Moderate |
| VH3/VL1 | Moderate |

TABLE 2-continued

Binding score for 2G8 chimeric and humanized clones to Sl/Sl4 hSCF248 cells

| 2G8 mAb | Binding Score |
| --- | --- |
| VH3/VL4 | Moderate |
| VH4/VL1 | Moderate |
| VH4/VL2 | Moderate |
| VH5/VL1 | Moderate high |
| VH5/VL4 | Moderate |

TABLE 3

Binding score for 5H10 chimeric and humanized clones to Sl/Sl4 hSCF248 cells

| 5H10 mAb | Binding Score |
| --- | --- |
| VH0/VK0 | high |
| VH1/VK1 | High |
| VH1/VK2 | High |
| VH1/VK3 | High |
| VH1/VK4 | No binding |
| VH2/VK2 | Moderate high |
| VH2/VK3 | high |
| VH3/VK2 | Moderate |
| VH3/VK3 | Moderate |
| VH4/VK2 | Moderate low |
| VH4/VK3 | Moderate low |
| VH5/VK2 | Low |
| VH5/VK3 | low |

Binding affinity was also assessed using a surface plasmon resonance (BIACORE™) analysis. The surface plasmon resonance (BIACORE™) data showed that the affinity for immobilized SCF248 peptide antigen of all humanized 5H10 antibodies having the VK1, VK2, or VK3 light chain was very similar to the binding affinity of the parental murine 5H10 using this assay. Humanized 5H10 antibodies having a VK4 light chain did not bind to the peptide.

TABLE 4

Surface Plasmon Resonance (BIACORE ™) data

| | VK0 | VK1 | VK2 | VK3 | VK4 |
| --- | --- | --- | --- | --- | --- |
| VH0 | 1.00 | 0.91 | | | |
| VH1 | 0.92 | 0.99 | 0.97 | 0.94 | — |
| VH2 | | 0.98 | 0.99 | 0.94 | — |
| VH3 | | 1.15 | 1.16 | 1.10 | — |
| VH3 | | 1.27 | 1.32 | 0.85 | — |
| VH5 | | 1.07 | 0.93 | 1.09 | — |

Figure 7B:
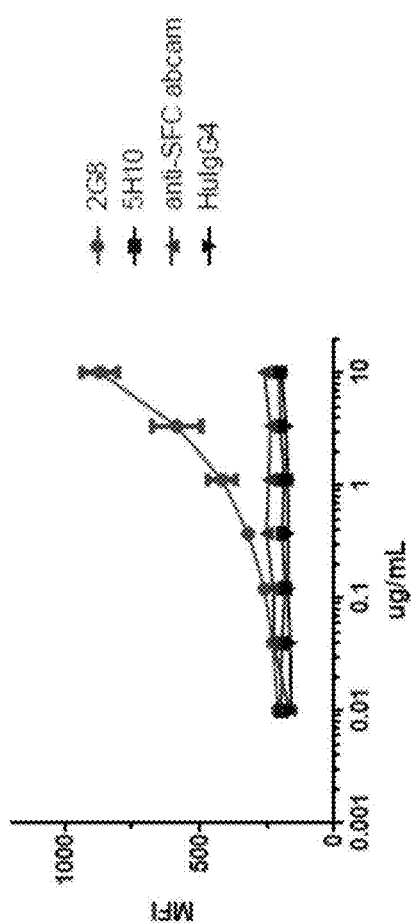
FIG. 7A-FIG. 7B shows binding by flow cytometry of murine 2G8 and murine 5H10 antibodies to early (FIG. 7A) and late (FIG. 7B) passage Sl/Sl4 hSCF248 (AMERICAN TYPE CULTURE COLLECTION® CRL-2454™) cells.
Figure 7A:
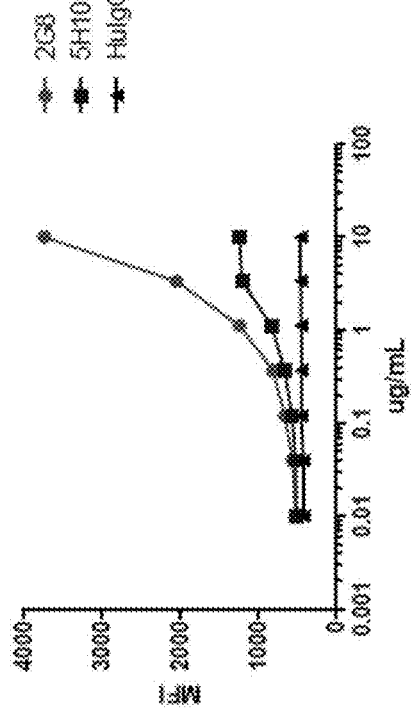

Example 4. Evaluation of anti-SCF Chimeric Antibody Binding by Flow Cytometry Sl/Sl4 hSCF248 cells, a transfected cell line that expresses SCF248, were utilized to test the binding of the chimeric antibodies 2G8 and 5H10. An anti-SCF antibody was used as a positive control for SCF binding. A human IgG4 antibody was used as a negative isotype control antibody. Sl/Sl4 hSCF248 cells at early passage (P3) were compared to cells at later passage (P5). As expected, the negative control (human IgG4 antibody) did not bind to either cell population. 5H10 bound to cells at early passage (FIG. 7A), but was not detected at later passage (FIG. 7B), due to loss of expression of SCF248 over multiple passages. Similarly, the maximum mean fluorescence intensity (MFI) detected with 10 µg/mL of 2G8 was reduced approximately four times at P5 compared to P3.

Figure 8A:
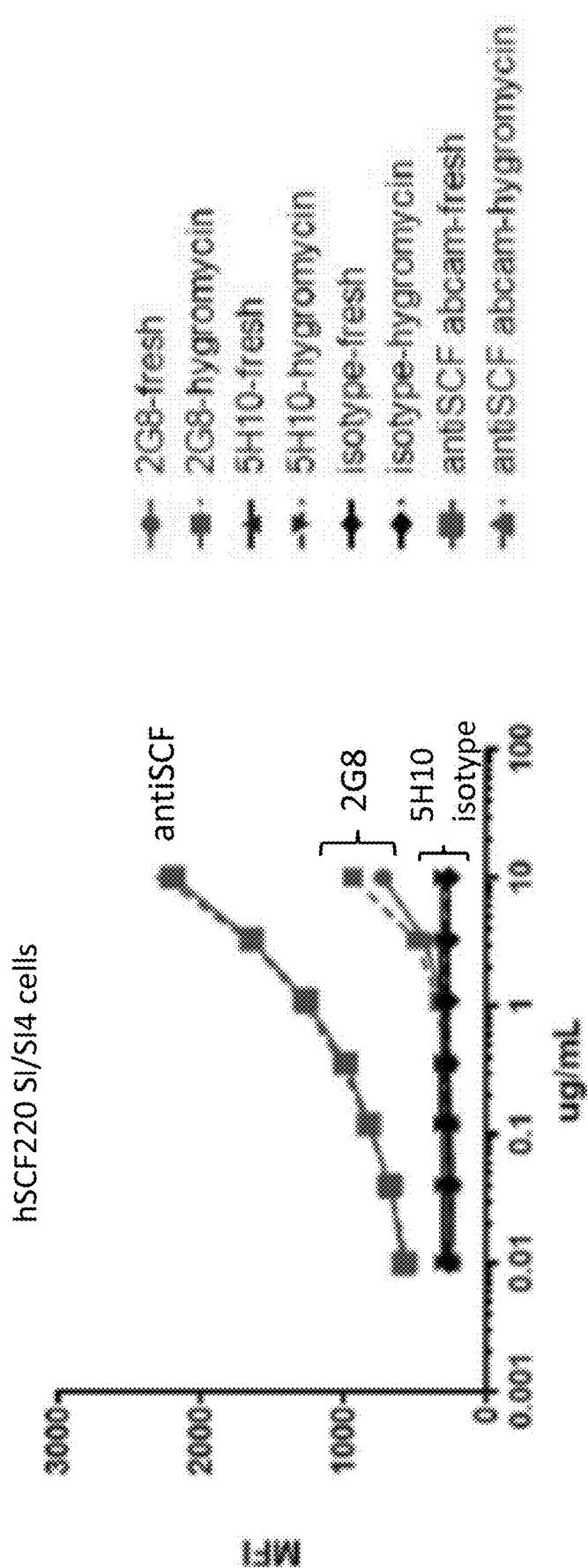
FIG. 8A-FIG. 8B shows binding of murine 2G8 and murine 5H10 to Sl/Sl4 hSCF220 (AMERICAN TYPE CULTURE COLLECTION® CRL-2453™) cells (FIG. 8A) and Sl/Sl4 hSCF248 cells (FIG. 8B) at early passage and to hygromycin B treated cells.
Figure 8B:
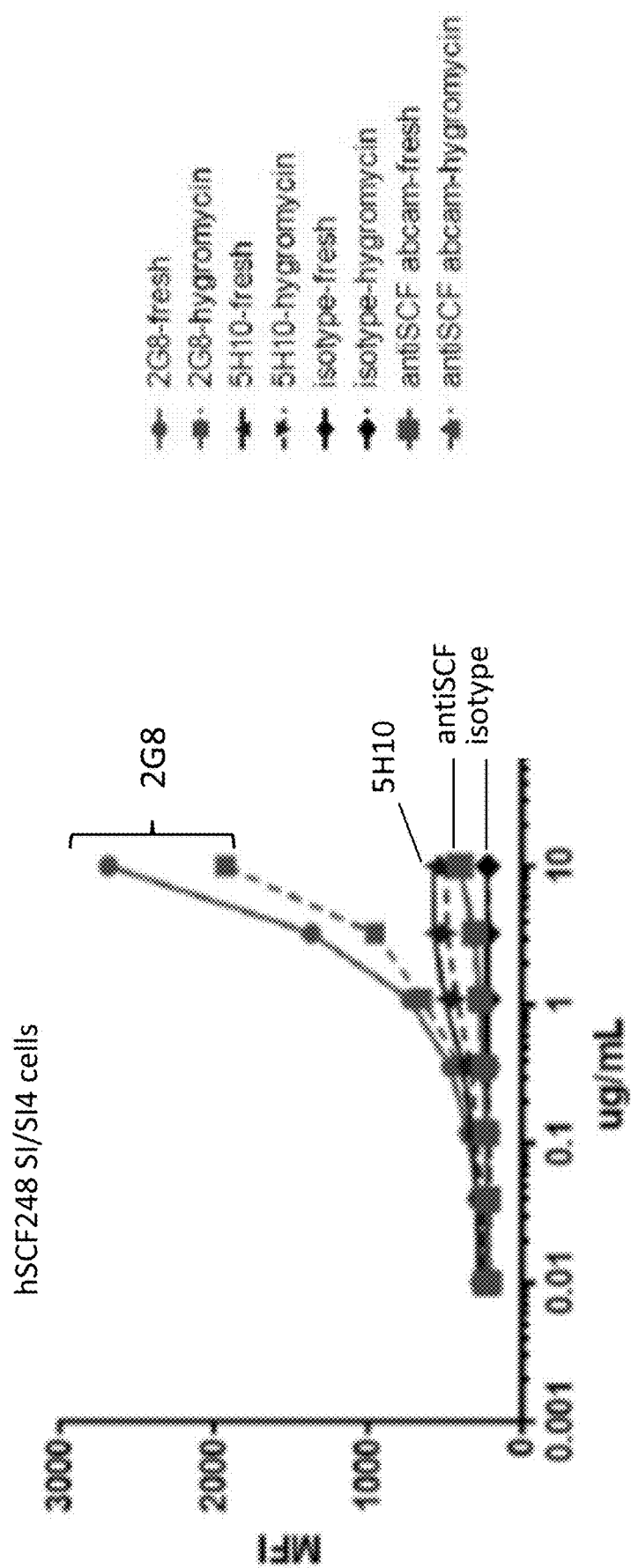
Figure 9A:
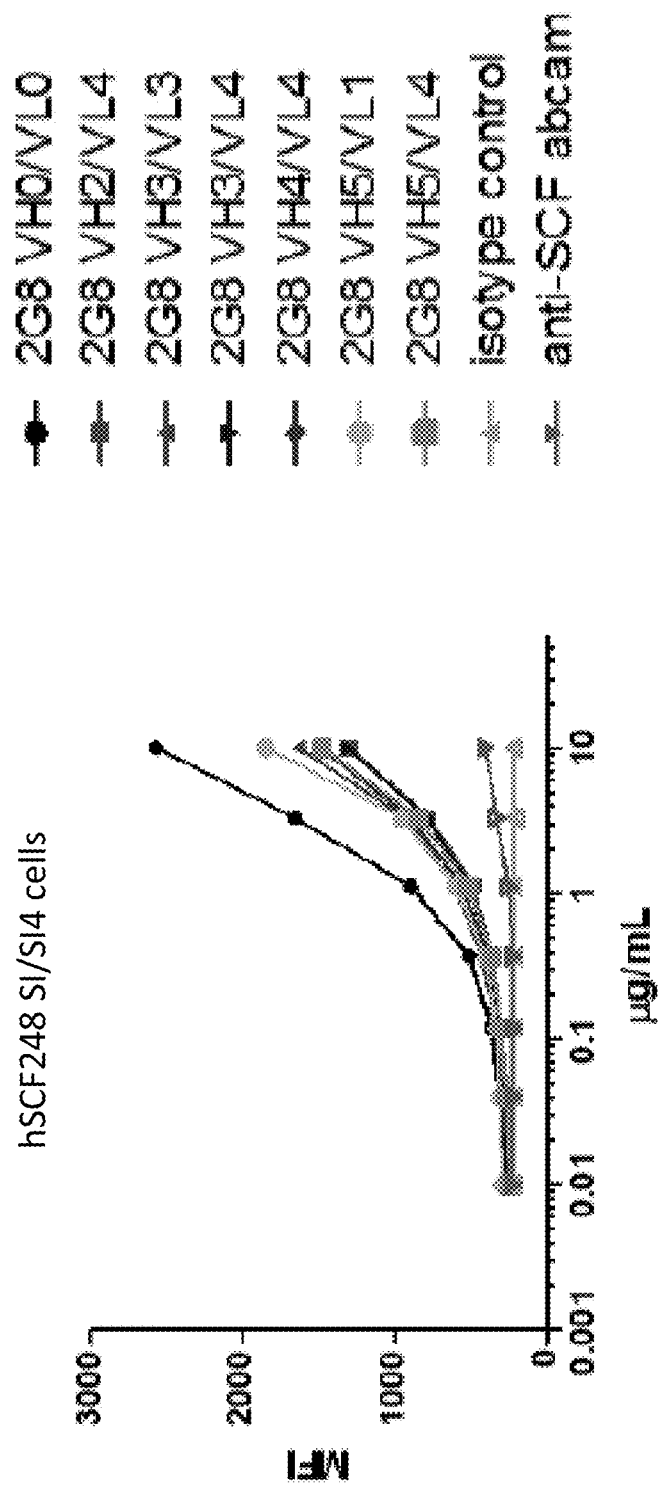
FIG. 9A-FIG. 9B shows binding of 2G8 humanized variants at different antibody concentrations by flow cytometry to Sl/Sl4 hSCF220 cells (FIG. 9B) and Sl/Sl4 hSCF248 cells (FIG. 9A).
Figure 9B:
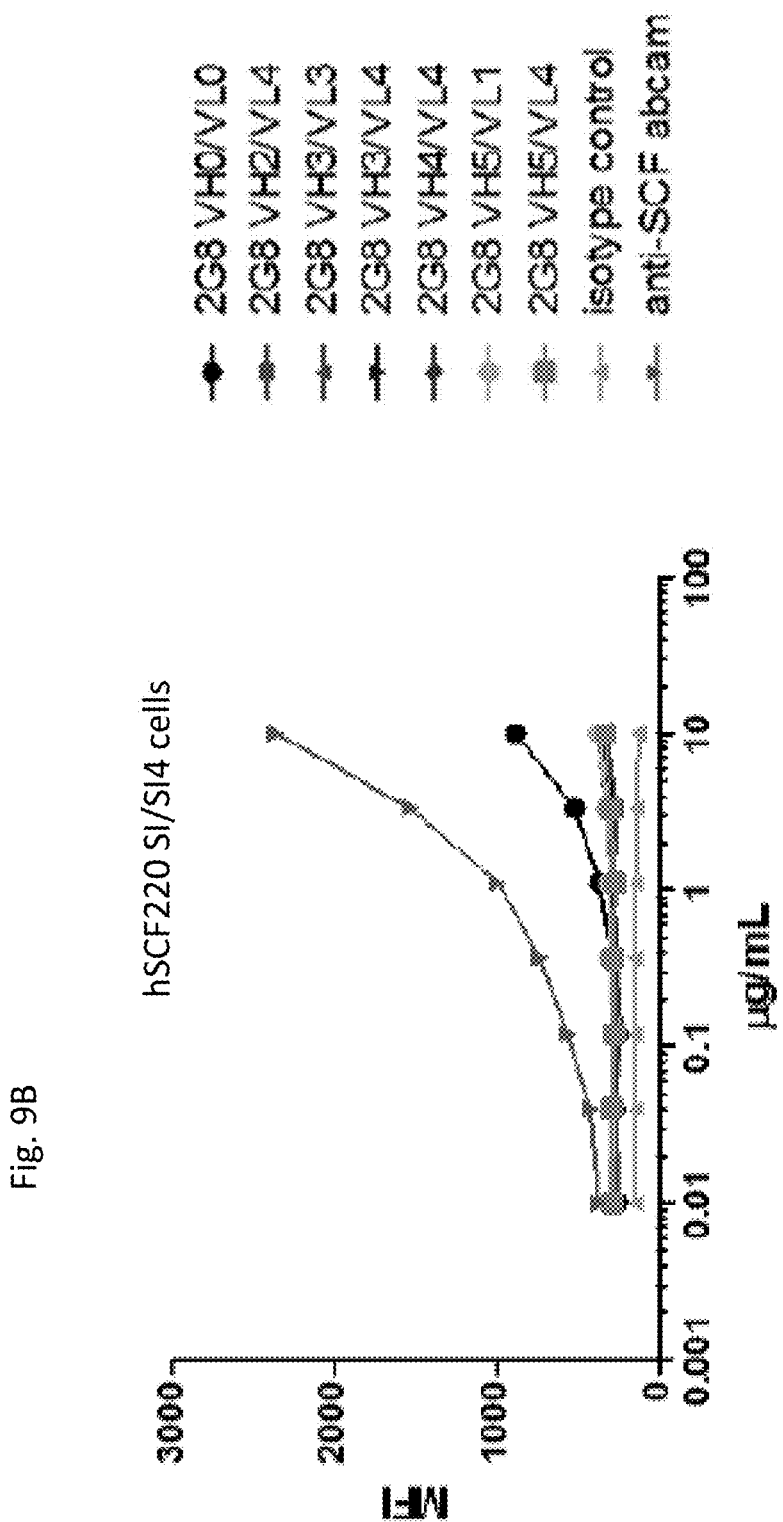

Similar observations were seen with hygromycin B-treated cells. Hygromycin selection was used to enrich the fraction of Sl/Sl4 cells expressing the relevant human SCF sequence. The binding of the two chimeric anti-SCF mAbs 2G8 and 5H10 and humanized anti-SCF antibodies were evaluated via flow cytometry. Sl/Sl4 hSCF248 cells and Sl/Sl4 hSCF220 cells, which are SCF248+ and SCF220+, respectively were utilized to test the binding and specificity of the chimeric antibodies 2G8 and 5H10. An anti-SCF antibody was used as a positive control for SCF binding. A human IgG4 antibody was used as a negative isotype control antibody. Hygromycin B treated cells were compared to early passage (P3) cells. The maximum mean fluorescent intensities (MFIs) and antibody dose response curves were similar to early passage (P3) cells (FIG. 8A, FIG. 8B).

Example 5. Binding Assessment of 2G8 and 5H10 Humanized mAbs by Flow Cytometry Sl/Sl4 hSCF248 cells and Sl/Sl4 hSCF220 cells, which are SCF248+ and SCF220+, respectively were utilized to test the binding and specificity of the chimeric antibodies 2G8 and 5H10, and humanized variants thereof. In both sets of experiments, a human IgG4 antibody was used as a negative isotype control antibody. The isotype control did not bind to Sl/Sl4 hSCF248 cells or Sl/Sl4 hSCF220 cells (FIGS. 9A, 9B, 10A, and 10B). The commercially available anti-SCF antibody (Abcam, Cat #EP665Y/ab52603) was found to bind Sl/Sl4 hSCF220 cells and weakly to Sl/Sl4 hSCF248 cells (only at a 1:25 dilution) (FIGS. 9A, 9B, 10A, and 10B). 2G8 VH0/VL0 (chimeric 2G8) exhibited stronger binding than its humanized clones. However, 2G8 VH0/VL0 also showed binding to Sl/Sl4 hSCF220 cells at antibody concentrations of 3.3 and 10 µg/mL (FIG. 9A, FIG. 9B). 5H10 VH0/VK0 showed higher binding compared to humanized clones 5H10 VH3/VK2, 5H10 VH3/VK3, 5H10 VH4/VK2, 5H10 VH4/VK3, 5H10 VH5/VK2, and 5H10 VH5/VK3 (FIG. 10A). No binding of 5H10 or any humanized variants thereof to Sl/Sl4 hSCF220 cells was observed (FIG. 10B). Differences among the indicated 5H10 humanized variants in terms of 50% maximal binding ($BC_{50}$) in this study are shown in Table 5. The binding of the 5H10 clones reached saturation at 3.3 µg/mL on Sl/Sl4 hSCF248 cells. (FIG. 10A).

TABLE 5

$BC_{50}$ (µg/mL) values for binding of chimeric and humanized 5H10 variants, isotype control, and commercially available anti-SCF antibody to Sl/Sl4 hSCF248 cells

| Sample ID | $BC_{50}$ (µg/mL) |
| --- | --- |
| 5H10 VH0/VK0 | 5.47 |
| 5H10 VH3/VK2 | 1.36 |
| 5H10 VH3/VK3 | 0.90 |
| 5H10 VH4/VK2 | 1.91 |
| 5H10 VH4/VK3 | 1.18 |
| 5H10 VH5/VK2 | 2.12 |
| 5H10 VH5/VK3 | 0.67 |
| Isotype control | n/a |
| Anti-SCF Abcam | 3.02 |

Figure 11A:
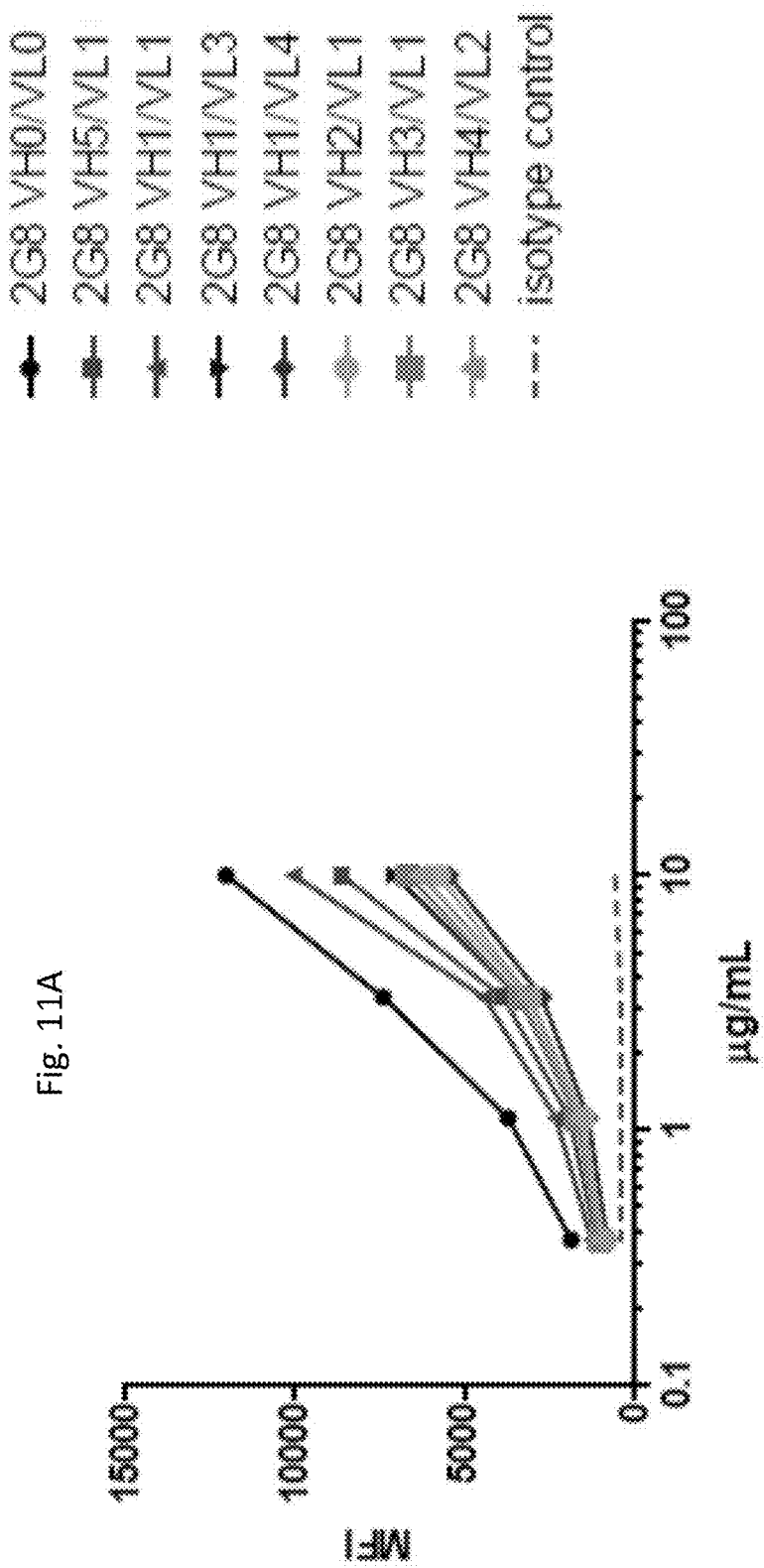
FIG. 11A-FIG. 11D shows binding of 2G8 humanized variants (FIG. 11A) and 5H10 humanized variants (FIG. 11B, 11C, 11D) at different antibody concentrations by flow cytometry to Sl/Sl4 hSCF248 cells.
Figure 11B:
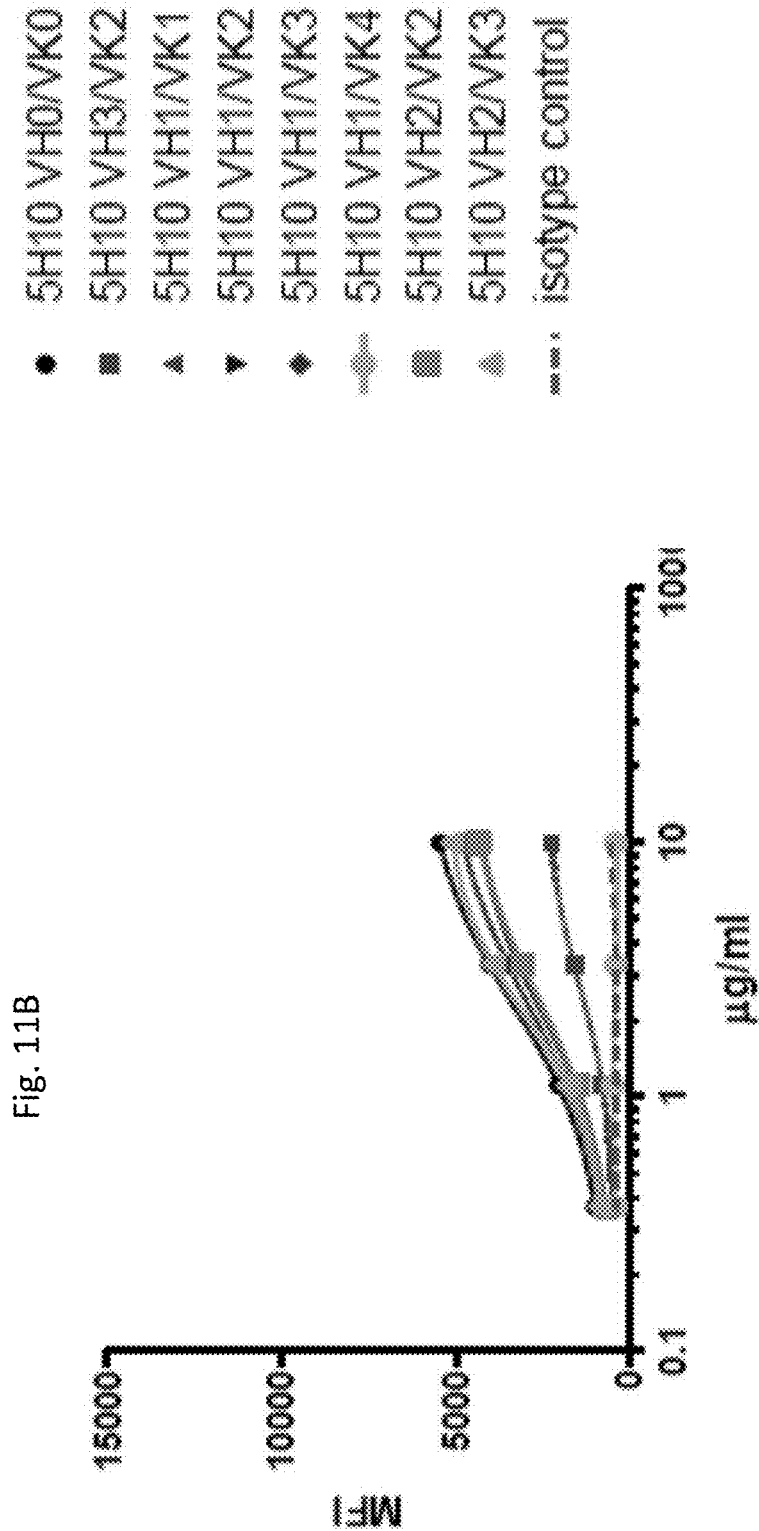

S1/S14 hSCF248 cells were utilized to test the binding of additional humanized variants of 5H10 and 2G8. 2G8 VH0/VL0 (chimeric) showed stronger cell binding than the humanized variants (FIG. 11A). The binding profiles of the humanized 5H10 clones 5H10 VH1/VK1, 5H10 VH1/VK2, 5H10 VH1/VK3, 5H10 VH2/VK2, 5H10 VH2/VK3 were comparable to that of 5H10 VH0/VK0 (FIG. 11B). In agreement with surface plasmon resonance (BIACORE™) data, presented above, the humanized variant 5H10 VH1/VK4 lost target binding (FIG. 11B). The isotype control did not bind to the Sl/Sl4 hSCF248 cells. Based on the data presented in these studies, the humanized 2G8 and 5H10 mAbs were assigned a binding score to Sl/Sl4 hSCF248 cells, which is presented in Tables 2 and 3, above.

Figure 11D:
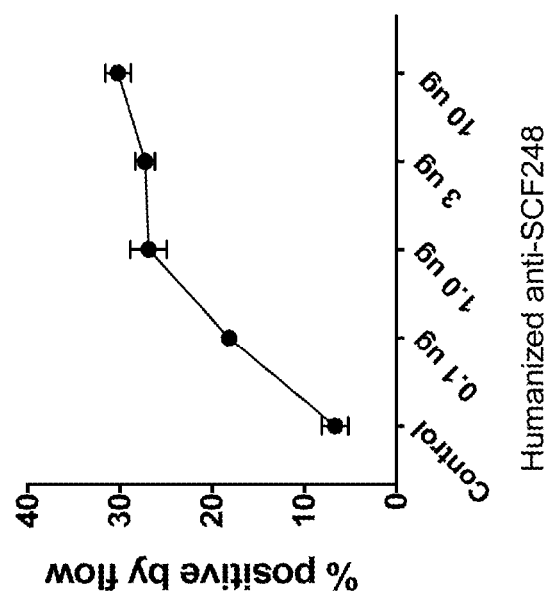
Figure 11C:
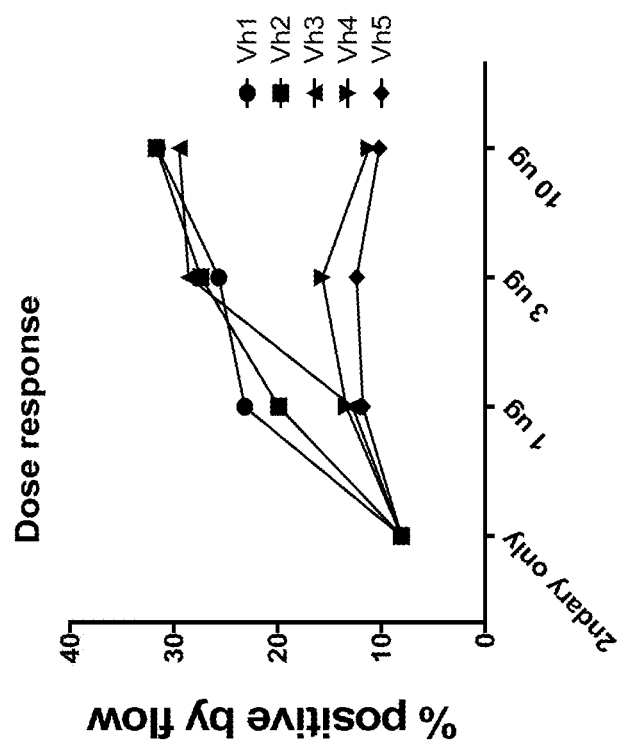
Figure 12B:
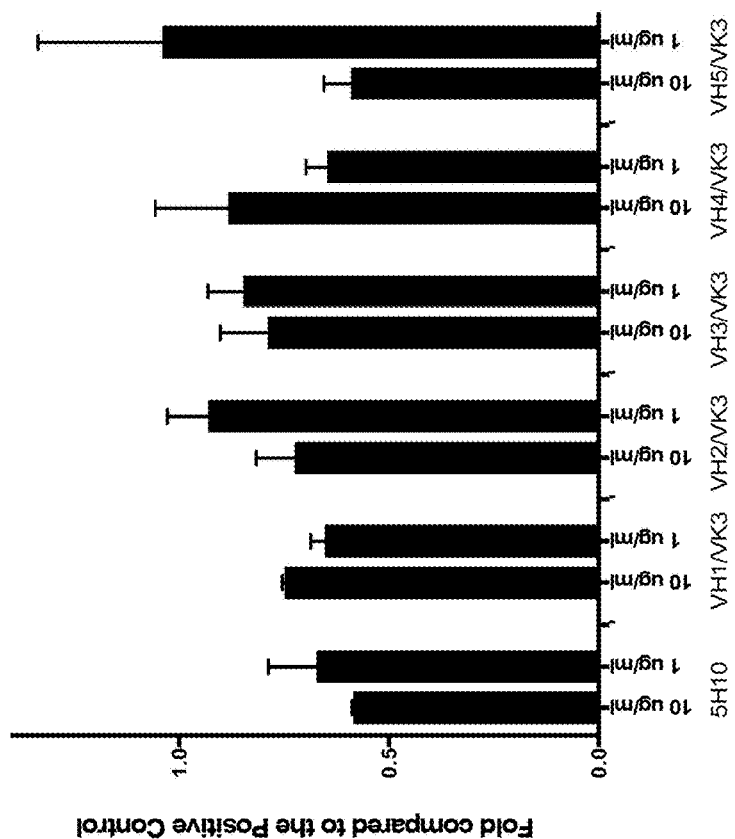
FIG. 12A-12D show the change in mRNA level of the CCL11 (FIG. 12A), Collagen 1A1 (FIG. 12B), fibronectin (FIG. 12C), or collagen 3 (FIG. 12D) after preincubation of human IPF myofibroblasts (Mfb) with a positive control (irrelevant antibody) or the antibody indicated under each bar in the figure. The murine parent antibody is indicated as "5H10" in the figure; humanized 5H10 antibodies VH1/VK3, VH2/VK3, VH3/VK3, VH4/VK3, and VH5/VK3 were also tested as shown. Antibody concentrations tested were 1 µg/mL or 10 µg/mL.
Figure 12A:
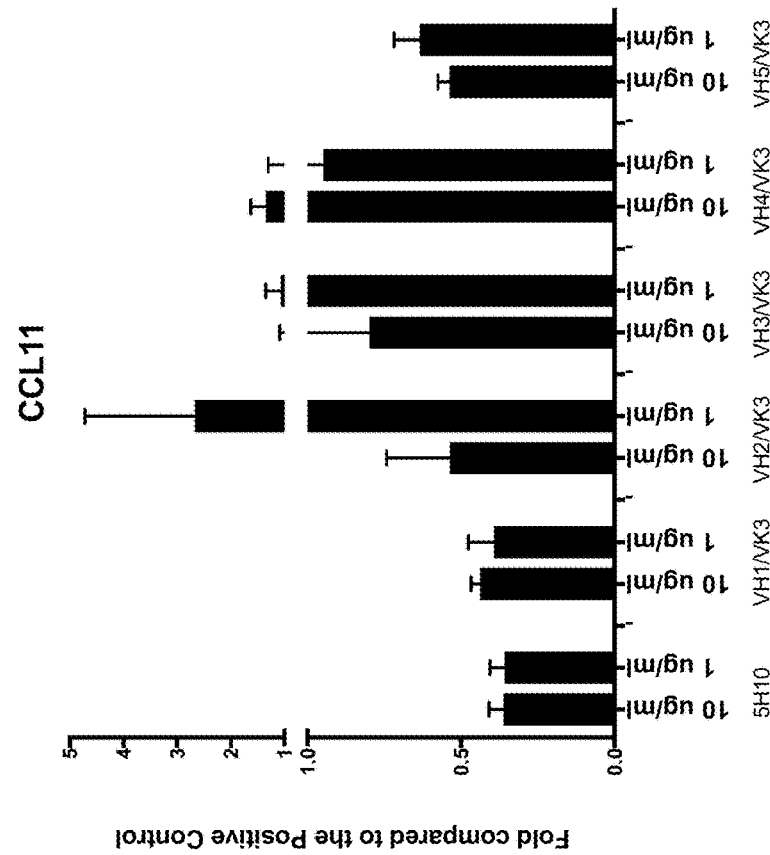
Figure 12D:
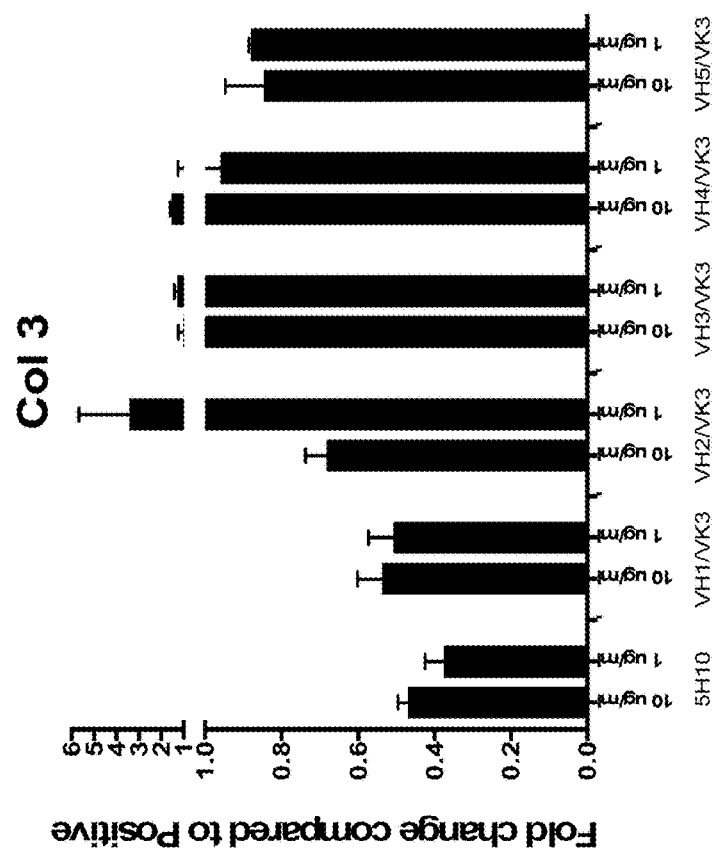
Figure 12C:
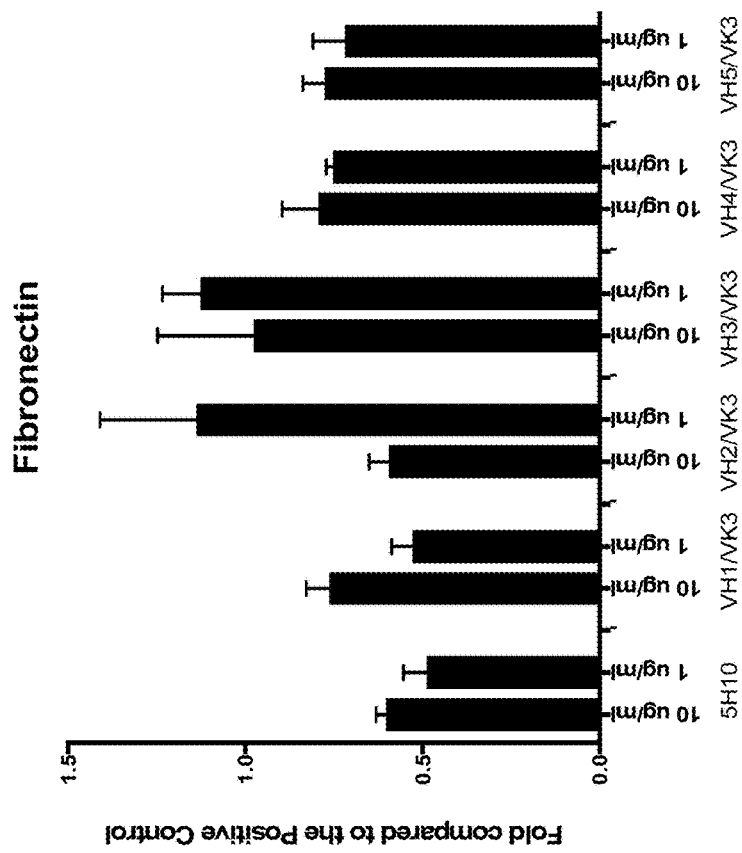

In a separate experiment, 5H10 clones VH1/VK3, VH2/VK3, VH3/VK3, VH4/VK3, and VH5/VK3 were assessed by flow cytometry for binding to the SCF248-expressing cell line. As shown in FIGS. 11C and 11D, VH1/VK3 and VH2/VK3 exhibited high binding, maximized at 1 μg/mL. The negative control was secondary antibody only. No binding was observed with the control SCF220-expressing cell line (not shown).

Example 6. In Vitro Blockade of the Interaction of SCF and c-Kit

The humanized 5H10 antibodies were tested for their capacity to inhibit the SCF-c-kit interaction and the inflammation feed-forward loop in vitro. Cultured human IPF myofibroblasts (Mfb), which express surface SCF248, were overlaid with LAD2 mast cells, an SCF-responsive cell line. Absent any other intervention, the Mfb stimulate the LAD2 cells, which produce cytokines to stimulate Mfb to produce additional cytokines and extracellular matrix proteins. In this assay, the readout for inflammation and the feed-forward loop is mRNA for CCL11, collagens 1 and 3, and fibronectin.

Murine 5H10 and humanized (VH1/VK3, VH2/VK3, VH3/VK3, VH4/VK3, and VH5/VK3) 5H10 antibodies were pre-incubated with Mfb at concentrations of 1 μg/mL and 10 μg/mL to assess their capacity to inhibit the feed-forward loop. Results are shown in FIGS. 12A-12D. The humanized VH1/VK3 antibody consistently demonstrated inhibition of the SCF-c-kit interaction, even at the lower concentration.

Figure 13:
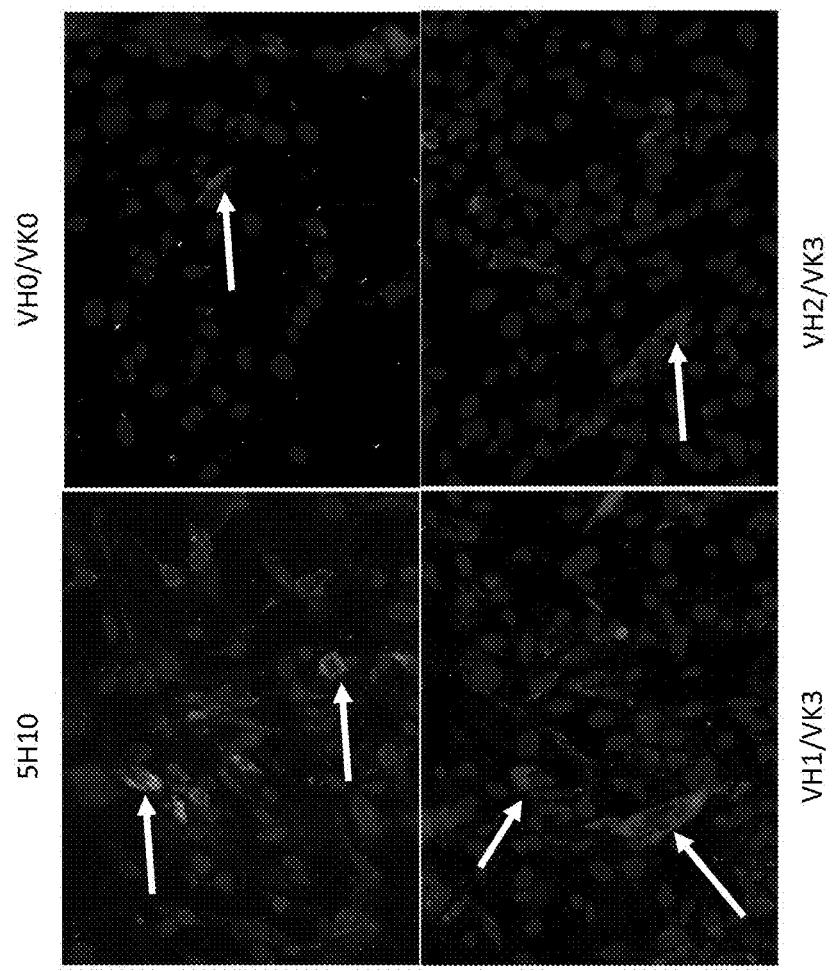
FIG. 13 shows the internalization of a murine 5H10 antibody, VH0/VK0 chimeric antibody, and humanized variants VH1/VK3 and VH2/VK3, each of which are labeled with a red dye (PHRODO™). Arrows point to exemplary cells exhibiting internalized antibody.

To assess the ability of humanized antibodies (5H10 VH1/VK3 and VH2/VK3) to internalize SCF248 on myofibroblasts, antibodies were labeled with a red dye (PHRODO™), which is colorless at neutral pH and fluoresces red at the low pH within an endosome. Labeled antibodies were incubated with cultured human IPF myofibroblasts for 45 minutes and red fluorescence was visualized by microscopy. As shown in FIG. 13, like the murine parent 5H10 antibody and the chimeric antibody (VH0/VK0), the humanized antibodies were rapidly internalized.

Example 7. Immunogenicity of Chimeric Antibody 5H10 and Humanized Lead Candidates The immunogenic potential of the five humanized antibodies 5H10 VH1/VK3, 5H10 VH2/VK3, 5H10 VH3/VK3, 5H10 VH4/VK3, and 5H10 VH5/VK3 was compared to the chimeric antibody 5H10 VH0/VK0.

Figure 14:
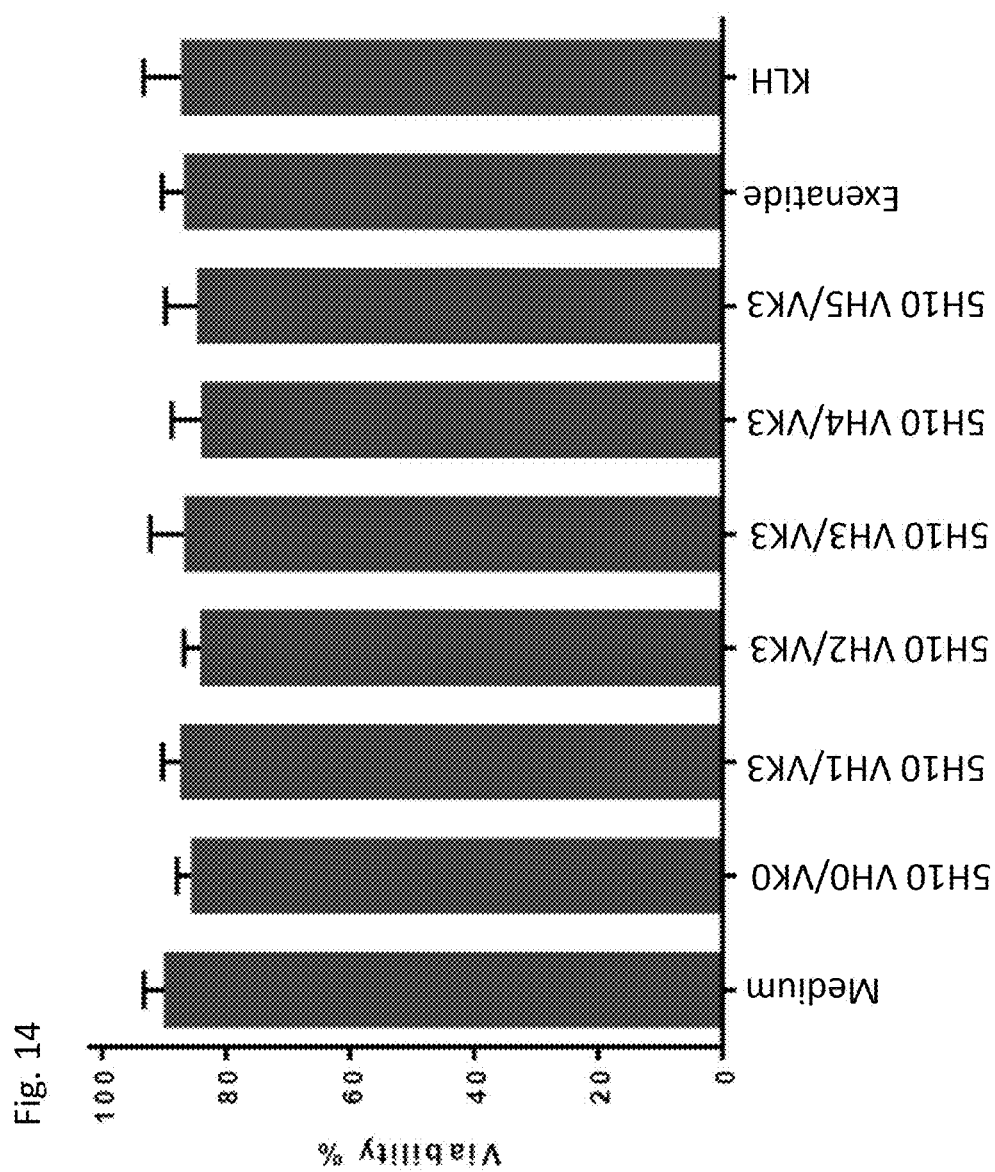
FIG. 14 shows the effect of 5H10 humanized variants on PBMC viability.
Figure 15A:
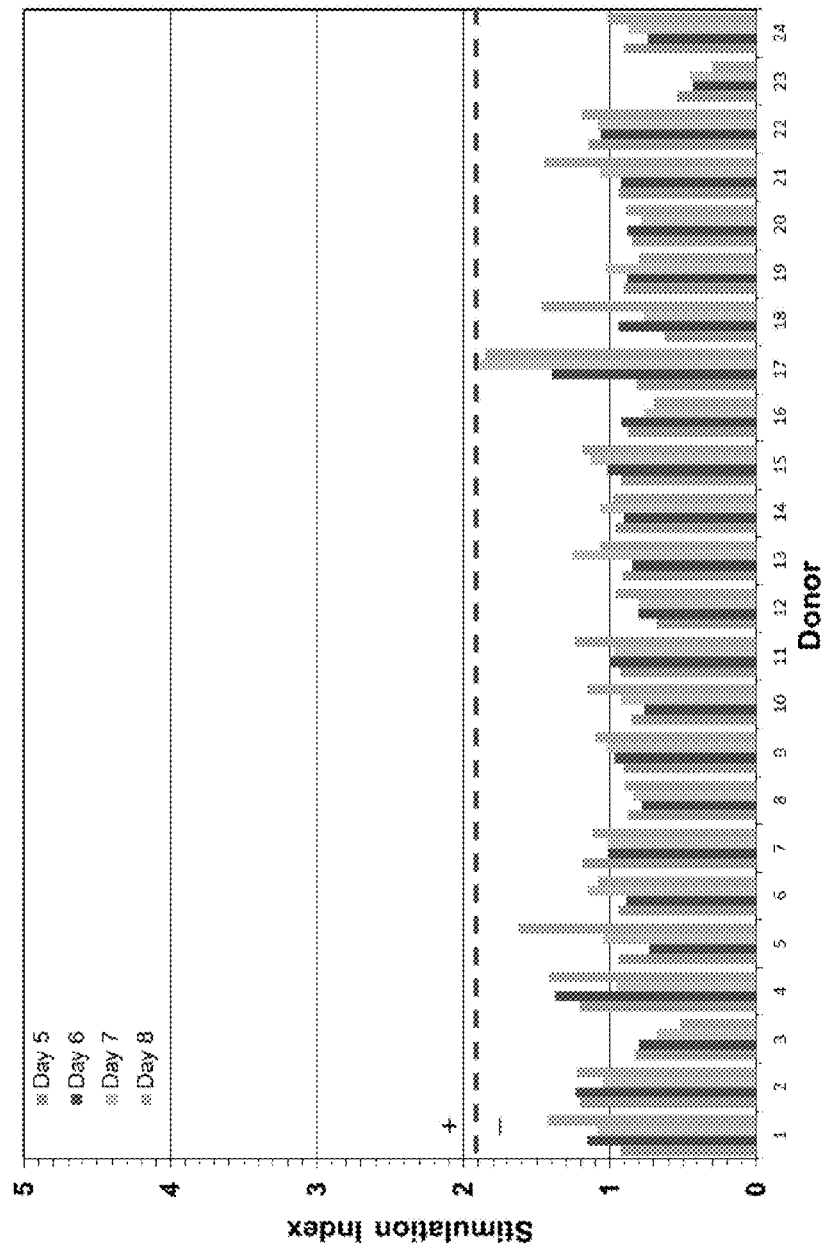
Figure 15F:
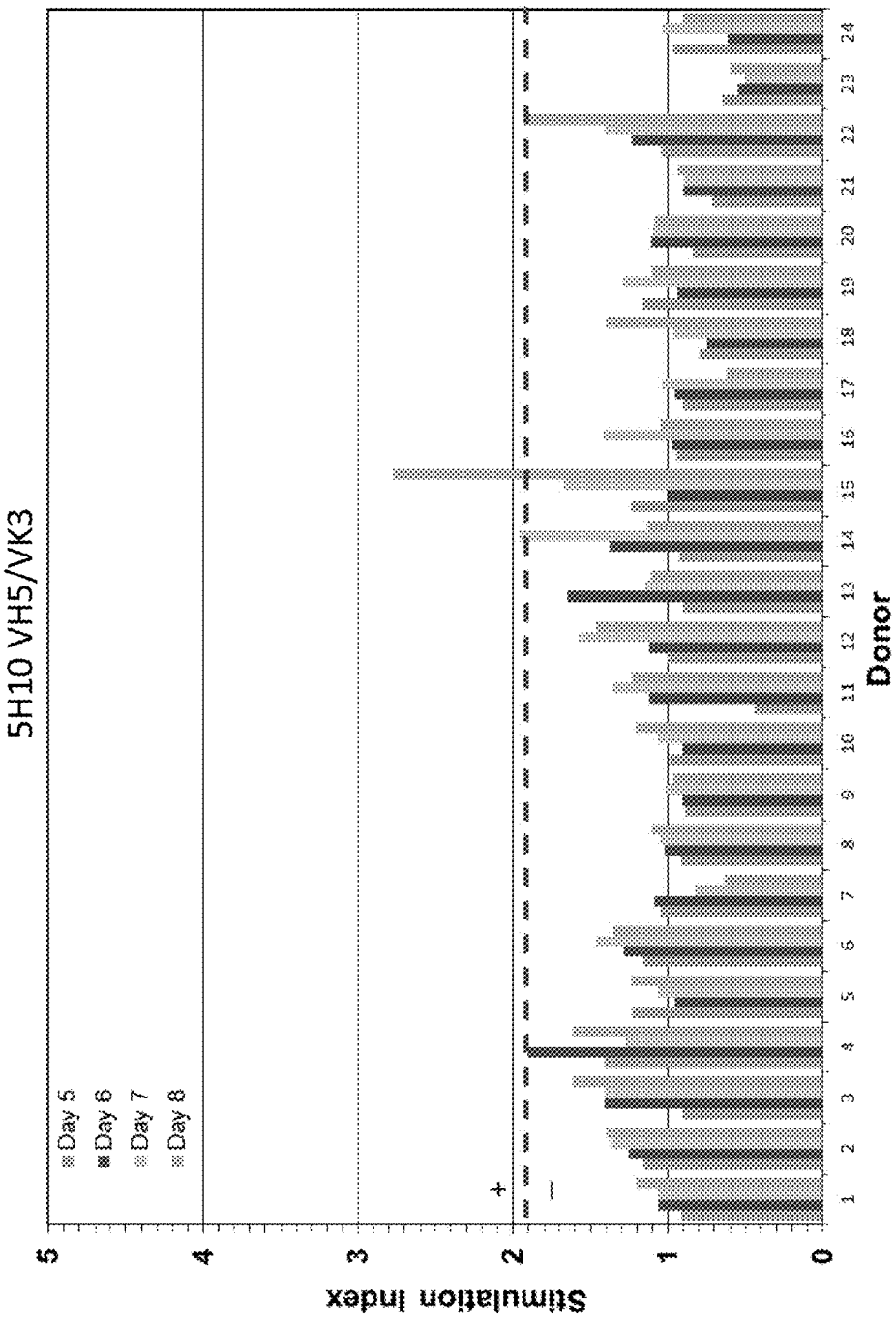
Figure 15G:
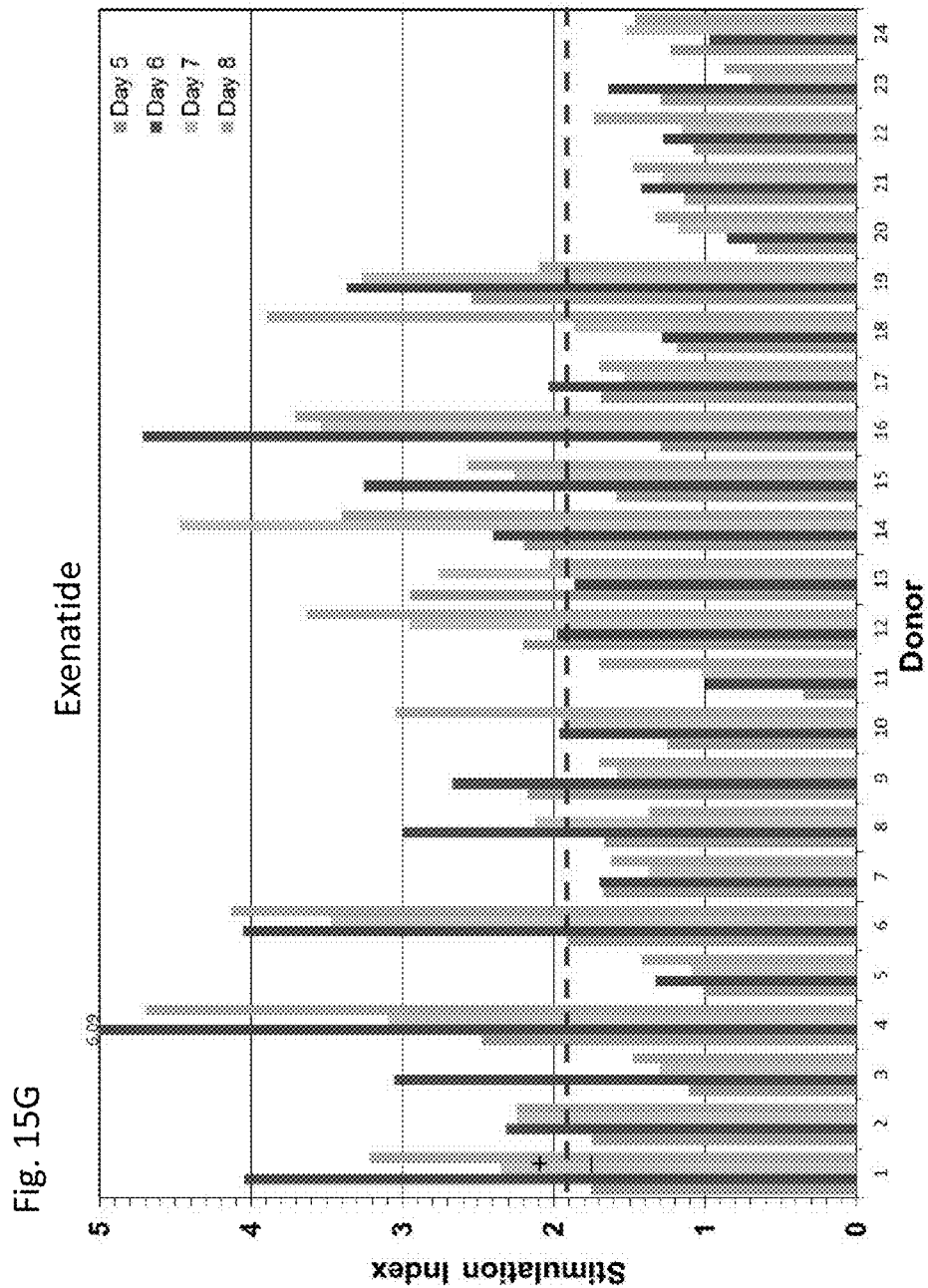
Figure 15H:
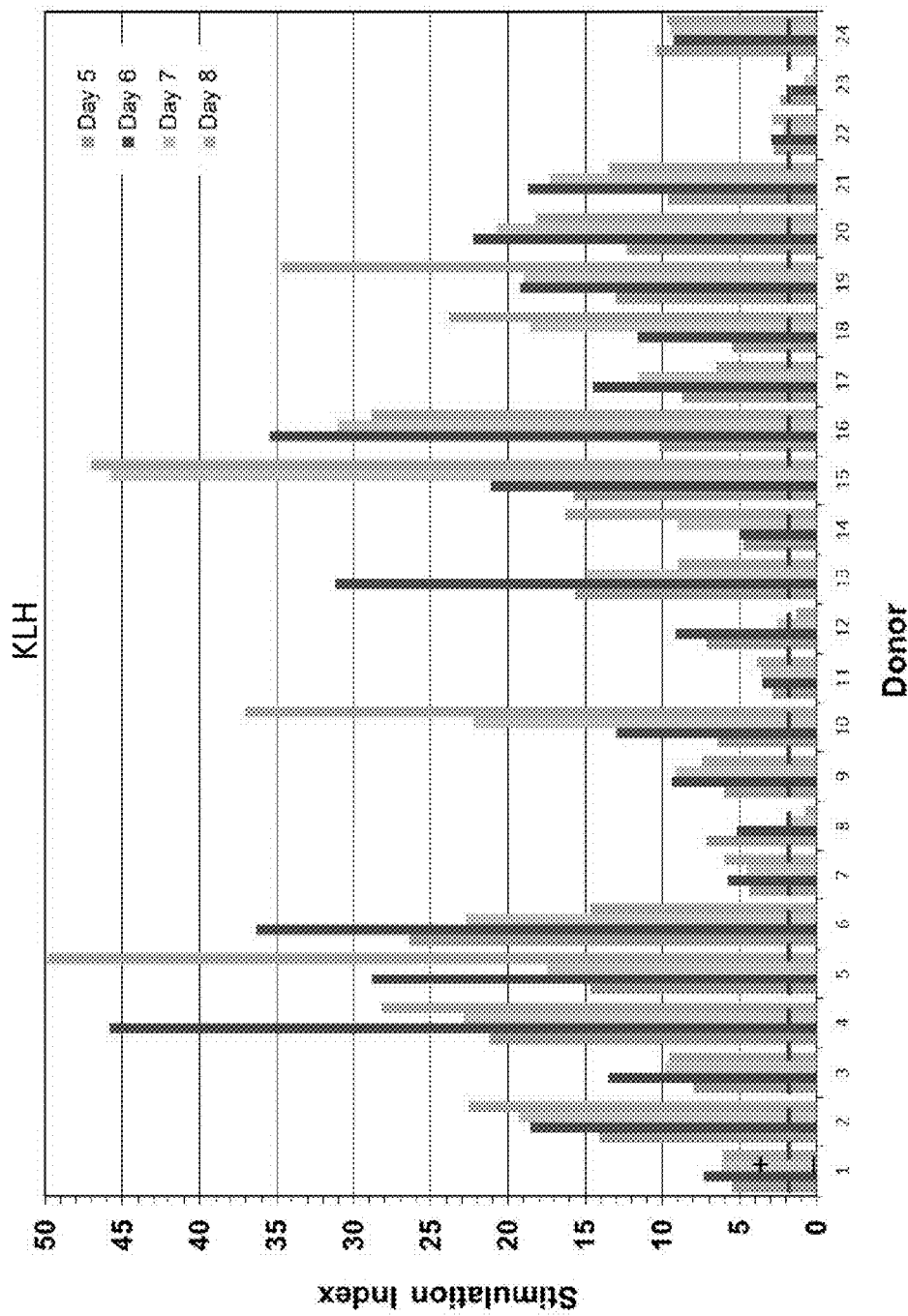

An initial assessment of any cytotoxic effects of the samples on PBMC viability was performed for five donors used in the EPISCREEN™ time course assays. CD8+ T cell depleted PBMC were incubated with the samples and the viability of the cells was determined using a LUNA-FL™ Automated Cell Counter on day 7. The results showed that the mean viabilities of PBMC from five donors treated with anti-SCF mAb were similar to that of cells treated with medium alone, ranging between 83% and 90% (FIG. 14). KLH (PIERCE™, LIFE TECHNOLOGIES®, UK) was used as a neoantigen. Exenatide (BYDUREON®, ASTRAZENECA®, UK) was used as a clinical benchmark control. FIG. 15A-H and Table 6 reveal the results obtained the EPISCREEN™ time course T cell proliferation assay of CD4+ T cell responses induced by the samples and controls. Both the clinical benchmark, exenatide, and the neo-antigen, KLH, elicited positive proliferative responses. A low frequency of positive response (SI≥1.90, p<0.05) rates were induced by 5H10 VH1/VK3, 5H10 VH2/VK3, and 5H10 VH3/VK3, ranging from 4% to 8%. Sample 5H10 VH5/VK3 induced higher positive responses in 17% of the donor cohort. 5H10 VH0/VK0 and 5H10 VH4/VK3 did not induce any positive responses. The mean magnitudes of the positive T cell proliferation responses were between 2.14 and 3.61 for all samples (Table 7).

Figure 16:
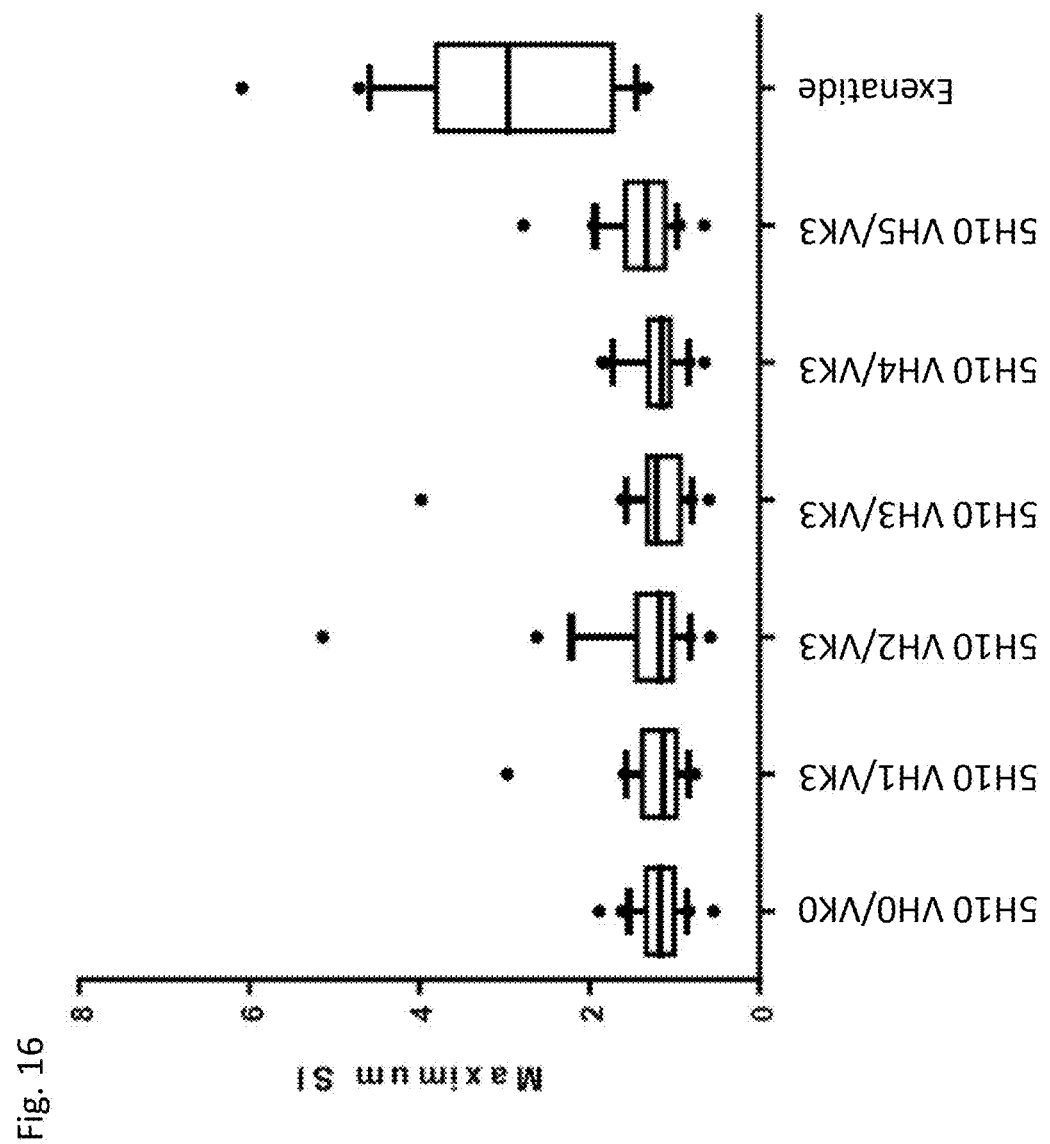
FIG. 16 shows variance analysis (ANOVA) of an EPISCREEN™ time course T cell proliferation assay.

Variance analysis, ANOVA, of the whole proliferation data set (using maximum magnitude of proliferation between days 5-8) was used to determine if there were any statistically significant differences in the maximum magnitude of CD4+ T cell responses to the test conditions compared to each other and the clinical benchmark, exenatide (FIG. 16). The maximum magnitude of T cell proliferative responses to exenatide were statistically higher than the responses to all the samples (Table 8).

TABLE 6

Summary of healthy donor T cell proliferative responses. Positive T cell responses for proliferation (SI ≥ 1.90, p < 0.05) during the entire time course days 5-8 ("P"). The frequency of positive responses is shown as a percentage at the bottom of the columns.

| | 5H10 VH0/ VK0 | 5H10 VH1/ VK3 | 5H10 VH2/ VK3 | 5H10 VH3/ VK3 | 5H10 VH4/ VK3 | 5H10 VH5/ VK3 | Exenatide | KLH |
|---|---|---|---|---|---|---|---|---|
| Donor 1 | | | | | | | P | P |
| Donor 2 | | | | | | | P | P |
| Donor 3 | | | | | | | P | P |
| Donor 4 | | | P | | P | | P | P |
| Donor 5 | | | | | | | | P |
| Donor 6 | | | | | | | P | P |
| Donor 7 | | | | | | | | P |
| Donor 8 | | | | | | | P | P |
| Donor 9 | | | | | | | P | P |
| Donor 10 | | | | | | | P | P |
| Donor 11 | | | | | | | | P |
| Donor 12 | | | | | | | P | P |
| Donor 13 | P | | | | | | P | P |
| Donor 14 | | | | | | P | P | P |
| Donor 15 | | | | | | P | P | P |
| Donor 16 | | | | | | | P | P |
| Donor 17 | | P | | | | | P | P |
| Donor 18 | | P | | | | | P | P |
| Donor 19 | | | | | | | P | P |
| Donor 20 | | | | | | | | P |
| Donor 21 | | | | | | | | P |
| Donor 22 | | | | | | P | | P |
| Donor 23 | | | | | | | | P |
| Donor 24 | | | | | | | | P |
| Proliferation % | 0 | 4 | 8 | 4 | 0 | 17 | 67 | 100 |

TABLE 7

Summary of the magnitude (±SD) of positive (SI ≥ 1.90, significant $p < 0.05$) T cell proliferation responses. The mean SI was calculated from the average of all positive donor responses observed during the entire time course (days 5-8).

| Sample | Mean SI | SD | % Response |
| --- | --- | --- | --- |
| VH0/VK0 | N/A | N/A | 0 |
| VH1/VK3 | 2.88 | ±0.13 | 4 |
| VH2/VK3 | 3.61 | ±1.36 | 8 |
| VH3/VK3 | 3.09 | ±0.88 | 4 |
| VH4/VK3 | N/A | N/A | 0 |
| VH5/VK3 | 2.14 | ±0.43 | 17 |
| Exenatide | 2.99 | ±0.92 | 67 |
| KLH | 14.95 | ±11.22 | 100 |

N/A indicates not applicable.

TABLE 8

Repeated measures one-way ANOVA (Friedman test) using a Dunn's post-test pairs comparison. The maximum SI from the proliferation data from all time points of all donors were analyzed.

|  | 5H10 VH0/VK0 | 5H10 VH1/VK3 | 5H10 VH2/VK3 | 5H10 VH3/VK3 | 5H10 VH4/VK3 | 5H10 VH5/VK3 |
| --- | --- | --- | --- | --- | --- | --- |
| 5H10 VH1/VK3 | ns | | | | | |
| 5H10 VH2/VK3 | ns | ns | | | | |
| 5H10 VH3/VK3 | ns | ns | ns | | | |
| 5H10 VH4/VK3 | ns | ns | ns | ns | | |
| 5H10 VH5/VK3 | ns | ns | ns | ns | ns | |
| Exenatide | **** | **** | **** | **** | **** | ** |

** $p < 0.01$,
**** $p < 0.0001$ and
ns = not significant.

In summary, the risk of clinical immunogenicity was determined by measuring ex vivo T cell responses using peripheral blood mononuclear cells (PBMC) isolated from 24 healthy donors representing the European and North American population (based on HLA allotypes) in the EPISCREEN™ time course T cell assay. T cell responses were measured using proliferation assays ([$^3$H]-thymidine uptake). The results showed that four of the lead humanized antibodies had a low potential for clinical immunogenicity.

Figure 17:
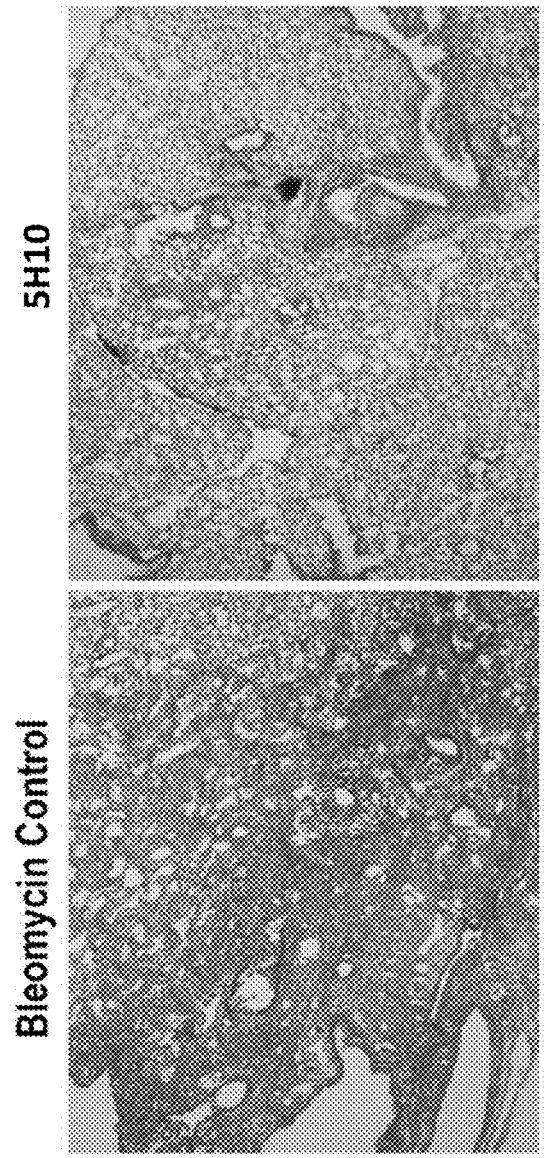
FIG. 17 shows lung histology of bleomycin control animals (left panel) and animals treated with bleomycin and 5H10 (20 mg/kg).
Figure 18:
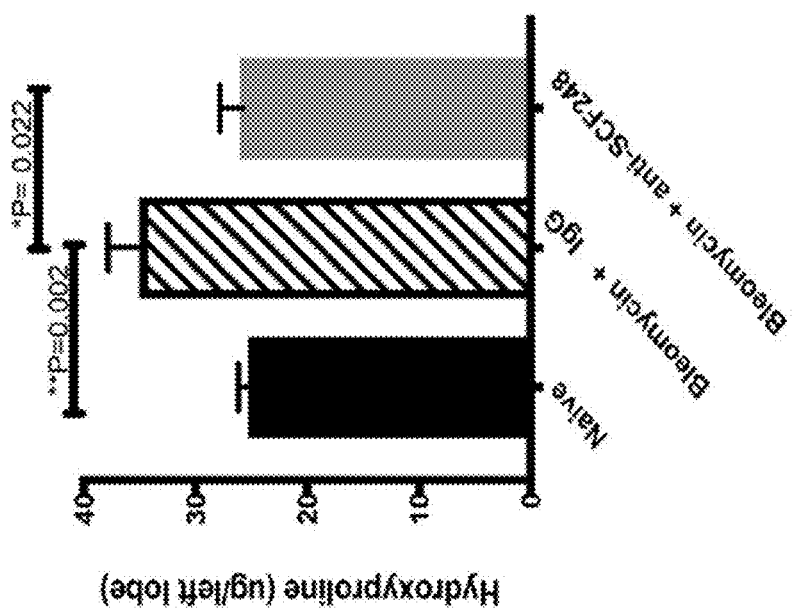
FIG. 18 shows decreases in lung hydroxyproline in animals treated with bleomycin and control IgG vs. animals treated with bleomycin and 5H10 (20 mg/kg; referred to in the figure as anti-SCF248).
Figure 19:
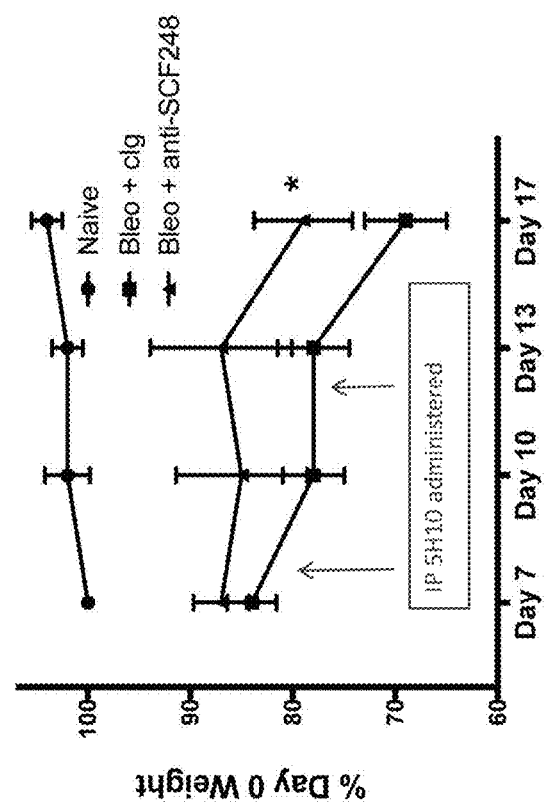
FIG. 19 shows the body weight as a % of the weight measured at day 0, over time in naïve mice, mice treated with bleomycin to induce lung fibrosis, and control Ig antibody (Bleo+cIg), and mice treated with bleomycin and murine 5H10 antibody (referred to in the figure as anti-SCF248). Antibody was administered at the indicated timepoints.
Figure 20:
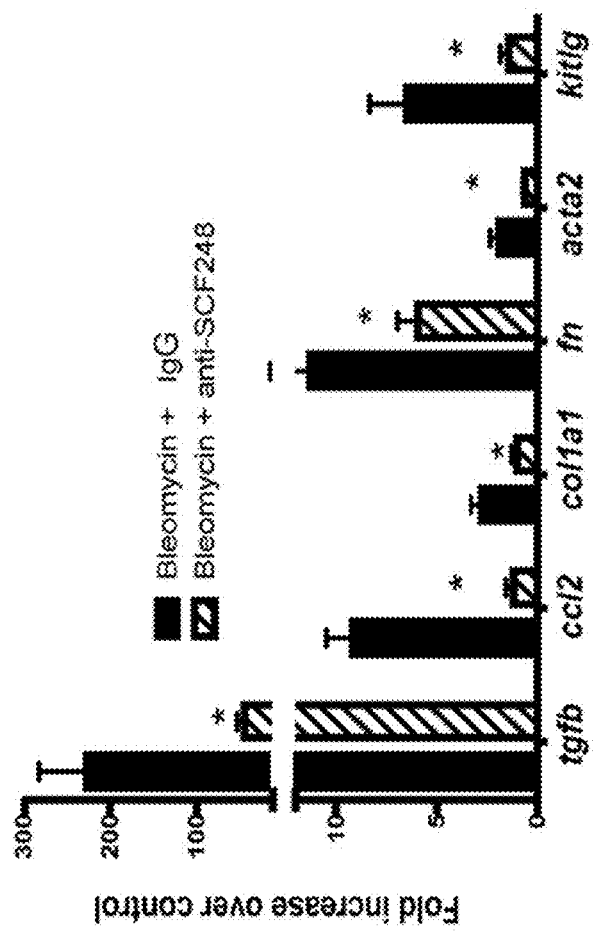
FIG. 20 shows decreases in mRNA for inflammatory cytokine and markers of myofibroblast activation (TGFβ, CCL2, Col1a1, Fibronectin (fn), smooth muscle actin (acta2), and stem cell factor (kit1g)) in animals treated with bleomycin and control IgG vs. animals treated with bleomycin and 5H10 (20 mg/kg; referred to in the figure as anti-SCF248).
Figure 21:
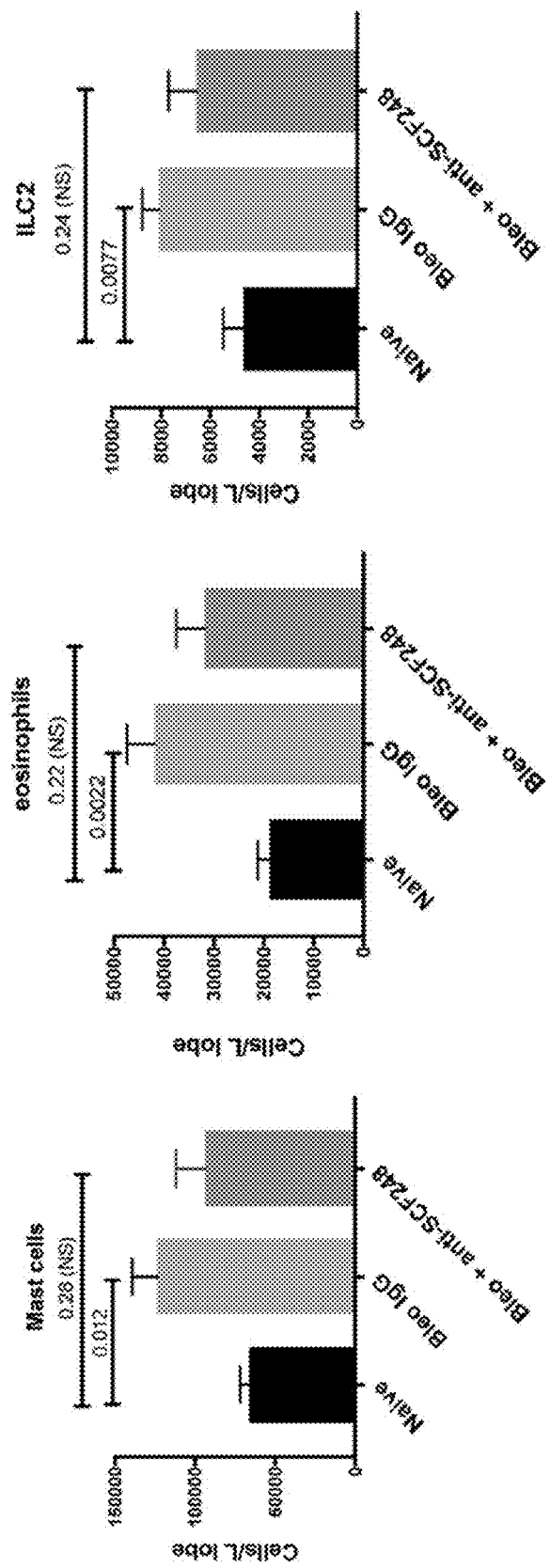
FIG. 21 shows decreases in lung mast cells, eosinophils and ILC2 lymphocytes in animals treated with bleomycin and control IgG vs. animals treated with bleomycin and 5H10 (20 mg/kg; referred to in the figure as anti-SCF248).
Figure 22:
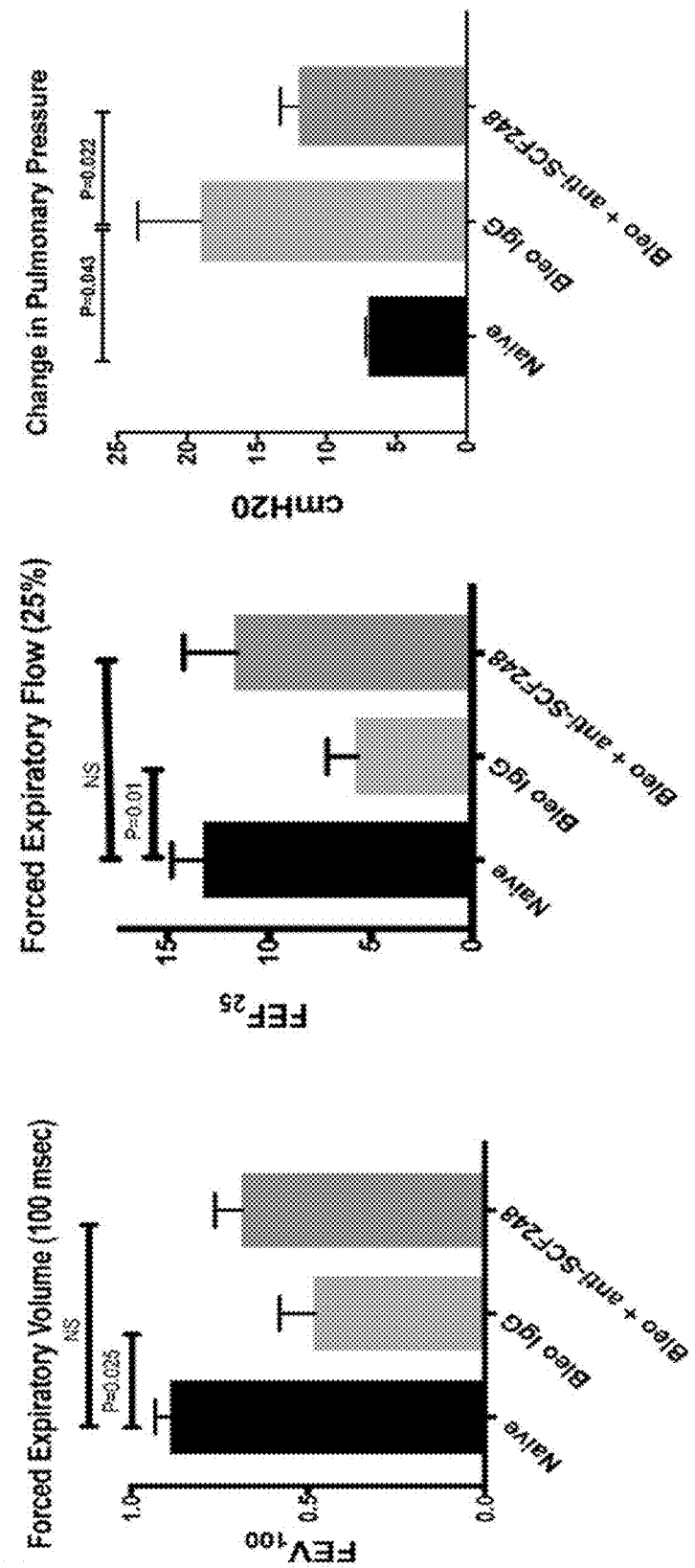
FIG. 22 shows that pulmonary function testing as measured by forced expiratory volume (left panel), forced expiratory flow (middle panel), and change in pulmonary pressure (right panel) were significantly improved in animals treated with bleomycin and 5H10 (20 mg/kg; referred to in the figure as anti-SCF248) compared to animals treated with bleomycin and control IgG.

Example 8. Evaluation of Murine 5H10 in a Bleomycin Model of Lung Inflammation and Fibrosis The bleomycin animal model of pulmonary fibrosis was employed to assess in vivo effects of 5H10. Bleomycin is a chemotherapeutic agent that causes pulmonary fibrosis in humans and animals. C57BL6 mice were administered bleomycin intratracheally on Day 1, and on Days 8 and 12 received 5H10 intraperitoneally at 20 mg/kg or isotype-matched control antibody. On Day 17 samples were collected. The 5H10-treated animals had significant improvements in lung histology (FIG. 17), decreases in lung hydroxyproline (a quantitative measure of fibrosis; FIG. 18), maintenance of body weight over time (FIG. 19), decreases in mRNA for inflammatory cytokine and markers of myofibroblast activation (FIG. 20), and in lung mast cells, eosinophils and ILC2 lymphocytes (FIG. 21). Pulmonary function testing was also significantly improved (FIG. 22).

Thus, the study demonstrated that 5H10 was effective to reduce fibrosis and inflammation, and improve pulmonary function, in an in vivo model of pulmonary fibrosis.

Figure 23:
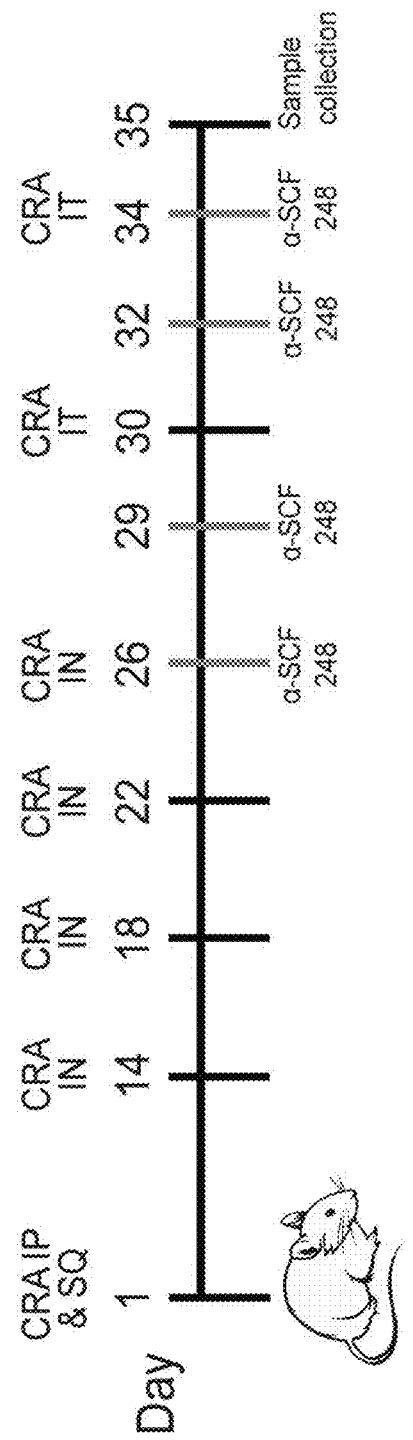
FIG. 23 shows a schematic of a study design in an in vivo chronic allergic asthma model used to test the humanized antibodies.

Example 9. Evaluation of Humanized 5H10 Antibodies in Chronic Allergic Asthma Model Humanized 5H10 antibodies were tested in an in vivo model of chronic allergic asthma. Mice were sensitized to cockroach antigen (CRA) intraperitoneally and subcutaneously followed by intranasal boosting on days 14, 18, 22 and 26. On days 26, 29, 32, and 34 they were administered indicated humanized 5H10 antibody or PBS control, intraperitoneally at 20 mg/kg or control irrelevant antibody. On days 30 and 34, they also received CRA intratracheally. On Day 35 specimens were collected. A schematic of the study design is provided in FIG. 23.

Airway resistance was significantly less in the animals treated with antibody 5H10 VH1/VK3 compared to PBS control as well as to other humanized variant antibodies (FIG. 24A). Further, in animals treated with VH1/VK3 or VH2/VK3, there were significant decreases in lung IL-13 mRNA in relation to the chronic asthma control (i.e., compared to animals administered CRA without any antibody treatment (PBS controls)) (FIG. 24B). Moreover, matrix gene expression was significantly reduced in animals that received VH1/VK3 antibody treatment (Collagen 1 mRNA shown in FIG. 24C; Collagen 3 mRNA shown in FIG. 24D. SCF248 mRNA expression was also significantly reduced in animals treated with VH1/VK3 (FIG. 24E). FIGS. 25A, 25B, and 25C show that VH1/VK3 administration reduced mRNA levels of mucus protein Gob5 and cytokines IL-13 and IL-5 at concentrations of 1 mg/kg and 5 mg/kg. Accordingly, the data showed that the VH1/VK3 antibody blocked cytokine and matrix gene expression in vivo in a model of chronic asthma.

Example 10. Phase 1a Clinical Trial to Evaluate Safety, Pharmacokinetics, and Pharmacodynamics of the anti-SCF248 Antibody A Phase 1a study will enroll 110 healthy volunteers. The primary objective is to obtain safety assessment and obtain accurate pharmacokinetic and pharmacodynamic data for the humanized anti-SCF248 antibody 5H10.

Single and multiple ascending doses of humanized 5H10, or placebo, will be administered, either intravenously or subcutaneously. Six to 8 subjects will make up one group. The starting dose will be based on toxicology studies performed according to good laboratory practices. The baseline pharmacokinetics will be obtained for all development and product lifetime. To assess pharmacodynamics, the number of circulating c-kit+ cells will be assessed, including mast cell progenitor cells and type 2 innate lymphoid (ILC2) cells, in addition to serum inflammatory markers such as SCF165.

Example 11. A Clinical Study to Evaluate Safety and Efficacy of the anti-SCF248 Antibody in Patients A clinical study will enroll patients suffering from an inflammatory disorder such as atopic dermatitis, chronic urticaria, pulmonary fibrosis, and/or others. One object of the study is to establish a dose-response relationship between humanized 5H10 antibody and pharmacodynamic markers in diseased patients e.g., the number of circulating c-kit+ cells, such as mast cell progenitor cells and type 2 innate lymphoid cells (ILC2) cells. Inflammatory biomarkers, such as ADAM8, CCL17, EPX, RNASE3, CCL2, CCL5, tryptase, histamine and SCF165 will also be measured.

A single, ascending dose of 5H10 antibody will be given to each subject group. The starting dose will be based on Phase 1a pharmacodynamic biomarkers. Patients will be treated for one, two, three, or more months. The results of the study will show that humanized 5H10 antibody is effective in stabilizing and/or treating and/or preventing the progression of inflammatory disorders and fibrotic diseases.

Publications, patents and patent applications cited herein are specifically incorporated by reference in their entireties. While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

The invention claimed is:

1. An isolated nucleic acid encoding an antibody, comprising a heavy chain CDR1, CDR2, and CDR3 comprising SEQ ID NOs: 1, 2, and 3, respectively; and a light chain CDR1, CDR2, and CDR3 comprising SEQ ID NOs: 4, 5, and 6, respectively.

2. An expression vector comprising a nucleic acid encoding an antibody, comprising a heavy chain CDR1, CDR2, and CDR3 comprising SEQ ID NOs: 1, 2, and 3, respectively; and a light chain CDR1, CDR2, and CDR3 comprising SEQ ID NOs: 4, 5, and 6, respectively.

3. An isolated host cell comprising the expression vector of claim 2.

* * * * *

```
                              SEQUENCE LISTING

Sequence total quantity: 50
SEQ ID NO: 1             moltype = AA   length = 5
FEATURE                  Location/Qualifiers
source                   1..5
                         mol_type = protein
                         organism = Mus musculus
SEQUENCE: 1
SYWMN                                                                    5

SEQ ID NO: 2             moltype = AA   length = 17
FEATURE                  Location/Qualifiers
source                   1..17
                         mol_type = protein
                         organism = Mus musculus
SEQUENCE: 2
QIYPGDGDTH YNGKFKG                                                       17

SEQ ID NO: 3             moltype = AA   length = 7
FEATURE                  Location/Qualifiers
source                   1..7
                         mol_type = protein
                         organism = Mus musculus
SEQUENCE: 3
SNWVGSY                                                                  7

SEQ ID NO: 4             moltype = AA   length = 16
FEATURE                  Location/Qualifiers
source                   1..16
                         mol_type = protein
                         organism = Mus musculus
SEQUENCE: 4
KSSQSLLESD GKTYLN                                                        16

SEQ ID NO: 5             moltype = AA   length = 7
FEATURE                  Location/Qualifiers
source                   1..7
                         mol_type = protein
                         organism = Mus musculus
SEQUENCE: 5
LVSRLDS                                                                  7

SEQ ID NO: 6             moltype = AA   length = 9
FEATURE                  Location/Qualifiers
source                   1..9
                         mol_type = protein
                         organism = Mus musculus
SEQUENCE: 6
WQGTHLPQT                                                                9

SEQ ID NO: 7             moltype = AA   length = 116
FEATURE                  Location/Qualifiers
source                   1..116
                         mol_type = protein
                         organism = Mus musculus
SEQUENCE: 7
QVQLQQSGAE LVRPGSSVKI SCKSSGYAFS SYWMNWVKQR PGQGLEWIGQ IYPGDGDTHY         60
NGKFKGKATL TADKSSSTAY MQLSRLTSED SAVYFCSSSN WVGSYWGQGT LVTVSA            116

SEQ ID NO: 8             moltype = AA   length = 116
FEATURE                  Location/Qualifiers
REGION                   1..116
```

```
                        note = Humanized 5H10 Heavy chain variable region VH1
source                  1..116
                        mol_type = protein
                        organism = synthetic construct
SEQUENCE: 8
QVQLVQSGAE LKKPGSSVKI SCKSSGYAFS SYWMNWVKQR PGQGLEWIGQ IYPGDGDTHY    60
NGKFKGKATL TADKSTSTAY MELSSLTSED SAVYFCSSSN WVGSYWGQGT LVTVSS       116

SEQ ID NO: 9            moltype = AA   length = 116
FEATURE                 Location/Qualifiers
REGION                  1..116
                        note = Humanized 5H10 Heavy chain variable region VH2
source                  1..116
                        mol_type = protein
                        organism = synthetic construct
SEQUENCE: 9
QVQLVQSGAE VKKPGSSVKI SCKSSGYAFS SYWMNWVKQR PGQGLEWIGQ IYPGDGDTHY    60
NGKFKGKATL TADKSTSTAY MELSSLRSED TAVYFCSSSN WVGSYWGQGT LVTVSS       116

SEQ ID NO: 10           moltype = AA   length = 116
FEATURE                 Location/Qualifiers
REGION                  1..116
                        note = Humanized 5H10 Heavy chain variable region VH3
source                  1..116
                        mol_type = protein
                        organism = synthetic construct
SEQUENCE: 10
QVQLVQSGAE VKKPGSSVKV SCKSSGYAFS SYWMNWVRQR PGQGLEWIGQ IYPGDGDTHY    60
NGKFKGKATL TADKSTSTAY MELSSLRSED TAVYFCSSSN WVGSYWGQGT LVTVSS       116

SEQ ID NO: 11           moltype = AA   length = 116
FEATURE                 Location/Qualifiers
REGION                  1..116
                        note = Humanized 5H10 Heavy chain variable region VH4
source                  1..116
                        mol_type = protein
                        organism = synthetic construct
SEQUENCE: 11
QVQLVQSGAE VKKPGSSVKV SCKSSGYAFS SYWMNWVRQR PGQGLEWIGQ IYPGDGDTHY    60
NGKFKGRVTI TADKSTSTAY MELSSLRSED TAVYFCSSSN WVGSYWGQGT LVTVSS       116

SEQ ID NO: 12           moltype = AA   length = 116
FEATURE                 Location/Qualifiers
REGION                  1..116
                        note = Humanized 5H10 Heavy chain variable region VH5
source                  1..116
                        mol_type = protein
                        organism = synthetic construct
SEQUENCE: 12
QVQLVQSGAE VKKPGSSVKV SCKSSGYAFS SYWMNWVRQR PGQGLEWIGQ IYPGDGDTHY    60
NGKFQGRVTI TADKSTSTAY MELSSLRSED TAVYYCSSSN WVGSYWGQGT LVTVSS       116

SEQ ID NO: 13           moltype = AA   length = 112
FEATURE                 Location/Qualifiers
source                  1..112
                        mol_type = protein
                        organism = Mus musculus
SEQUENCE: 13
DVVMTQTPLT LSVTIGQTAS ISCKSSQSLL ESDGKTYLNW LSQRPGQSPK RLIYLVSRLD    60
SGVPDRFTGS GSGTDFTLKI SRVEAEDLGV YYCWQGTHLP QTFGGGTKLE IK           112

SEQ ID NO: 14           moltype = AA   length = 112
FEATURE                 Location/Qualifiers
REGION                  1..112
                        note = Humanized 5H10 Light chain variable region VK1
source                  1..112
                        mol_type = protein
                        organism = synthetic construct
SEQUENCE: 14
DVVMTQSPLT LSVTLGQPAS ISCKSSQSLL ESDGKTYLNW LQQRPGQSPR RLIYLVSRLD    60
SGVPDRFTGS GSGTDFTLKI SRVEAEDVGV YYCWQGTHLP QTFGGGTKVE IK           112

SEQ ID NO: 15           moltype = AA   length = 112
FEATURE                 Location/Qualifiers
REGION                  1..112
                        note = Humanized 5H10 Light chain variable region VK2
source                  1..112
                        mol_type = protein
                        organism = synthetic construct
```

```
SEQUENCE: 15
DVVMTQSPLS LPVTLGQPAS ISCKSSQSLL ESDGKTYLNW LQQRPGQSPR RLIYLVSRLD    60
SGVPDRFTGS GSGTDFTLKI SRVEAEDVGV YYCWQGTHLP QTFGGGTKVE IK          112

SEQ ID NO: 16           moltype = AA   length = 112
FEATURE                 Location/Qualifiers
REGION                  1..112
                        note = Humanized 5H10 Light chain variable region VK3
source                  1..112
                        mol_type = protein
                        organism = synthetic construct
SEQUENCE: 16
DVVMTQSPLS LPVTLGQPAS ISCKSSQSLL ESDGKTYLNW LQQRPGQSPR RLIYLVSRLD    60
SGVPDRFSGS GSGTDFTLKI SRVEAEDVGV YYCWQGTHLP QTFGGGTKVE IK          112

SEQ ID NO: 17           moltype = AA   length = 112
FEATURE                 Location/Qualifiers
REGION                  1..112
                        note = Humanized 5H10 Light chain variable region VK4
source                  1..112
                        mol_type = protein
                        organism = synthetic construct
SEQUENCE: 17
DVVMTQSPLS LPVTLGQPAS ISCKSSQSLL ESDGKTYLNW FQQRPGQSPR RLIYLVSRLD    60
SGVPDRFSGS GSGTDFTLKI SRVEAEDVGV YYCWQGTHLP QTFGGGTKVE IK          112

SEQ ID NO: 18           moltype = DNA   length = 348
FEATURE                 Location/Qualifiers
source                  1..348
                        mol_type = other DNA
                        organism = Mus musculus
SEQUENCE: 18
caggttcagc tgcagcagtc tggggctgag ctcgtgaggc ctgggtcctc agtgaagatt    60
tcctgcaagt cttctggcta tgcattcagt agctactgga tgaactgggt gaagcagagg   120
cctggacagg gtcttgagtg gattggacag atttatcctg gagatggtga tactcactac   180
aatggaaagt tcaagggcaa agccacactg actgcagaca atcctccag cacagcctac    240
atgcagctca gcaggctaac atctgaggac tctgcggtct atttctgttc aagttcaaac   300
tgggtcggga gttactgggg ccaagggact ctggtcaccg tctcctca                348

SEQ ID NO: 19           moltype = DNA   length = 348
FEATURE                 Location/Qualifiers
misc_feature            1..348
                        note = Humanized heavy chain variable region VH1
source                  1..348
                        mol_type = other DNA
                        organism = synthetic construct
SEQUENCE: 19
caggtccagc tggtgcaatc tggggctgag ctgaagaagc ctgggtcctc ggtgaagatt    60
tcctgcaagt cttctggata tgcattcagc agctattgga tgaactgggt gaagcagagg   120
cctggacaag gcttgagtg gattggacag atctatcctg gagatggtga tactcactac    180
aatggaaagt tcaagggcaa agccacgctg accgcggaca atccacgag cacagcctac    240
atggagctga gcagcctgac atctgaggac tctgccgtgt atttctgttc aagttcaaac   300
tgggtcggga gttactgggg ccaaggaacc ctggtcaccg tctcctca                348

SEQ ID NO: 20           moltype = DNA   length = 348
FEATURE                 Location/Qualifiers
misc_feature            1..348
                        note = Humanized heavy chain variable region VH2
source                  1..348
                        mol_type = other DNA
                        organism = synthetic construct
SEQUENCE: 20
caggtccagc tggtgcaatc tggggctgag gtgaagaagc ctgggtcctc ggtgaagatt    60
tcctgcaagt cttctggata tgcattcagc agctattgga tgaactgggt gaagcagagg   120
cctggacaag gcttgagtg gattggacag atctatcctg gagatggtga tactcactac    180
aatggaaagt tcaagggcaa agccacgctg accgcggaca atccacgag cacagcctac    240
atggagctga gcagcctgag atctgaggac acggccgtgt atttctgttc aagttcaaac   300
tgggtcggga gttactgggg ccaaggaacc ctggtcaccg tctcctca                348

SEQ ID NO: 21           moltype = DNA   length = 348
FEATURE                 Location/Qualifiers
misc_feature            1..348
                        note = Humanized heavy chain variable region VH3
source                  1..348
                        mol_type = other DNA
                        organism = synthetic construct
SEQUENCE: 21
caggtccagc tggtgcaatc tggggctgag gtgaagaagc ctgggtcctc ggtgaaggtt    60
tcctgcaagt cttctggata tgcattcagc agctattgga tgaactgggt gcgacagagg   120
```

```
cctggacaag ggcttgagtg gattggacag atctatcctg gagatggtga tactcactac    180
aatgaaagt tcaagggcaa agccacgctg accgcggaca atccacgag cacagcctac      240
atggagctga gcagcctgag atctgaggac acggccgtgt atttctgttc aagttcaaac    300
tgggtcggga gttactgggg ccaaggaacc ctggtcaccg tctcctca                 348

SEQ ID NO: 22              moltype = DNA   length = 348
FEATURE                    Location/Qualifiers
misc_feature               1..348
                           note = Humanized heavy chain variable region VH4
source                     1..348
                           mol_type = other DNA
                           organism = synthetic construct
SEQUENCE: 22
caggtccagc tggtgcaatc tggggctgag gtgaagaagc ctgggtcctc ggtgaaggtt    60
tcctgcaagt cttctggata tgcattcagc agctattgga tgaactgggt gcgacagagg    120
cctggacaag ggcttgagtg gattggacag atctatcctg gagatggtga tactcactac    180
aatgaaagt tcaagggcag agtcacgatt accgcggaca atccacgag cacagcctac      240
atggagctga gcagcctgag atctgaggac acggccgtgt atttctgttc aagttcaaac    300
tgggtcggga gttactgggg ccaaggaacc ctggtcaccg tctcctca                 348

SEQ ID NO: 23              moltype = DNA   length = 348
FEATURE                    Location/Qualifiers
misc_feature               1..348
                           note = Humanized heavy chain variable region VH5
source                     1..348
                           mol_type = other DNA
                           organism = synthetic construct
SEQUENCE: 23
caggtccagc tggtgcaatc tggggctgag gtgaagaagc ctgggtcctc ggtgaaggtt    60
tcctgcaagt cttctggata tgcattcagc agctattgga tgaactgggt gcgacagagg    120
cctggacaag ggcttgagtg gattggacag atctatcctg gagatggtga tactcactac    180
aatgaaagt tccagggcag agtcacgatt accgcggaca atccacgag cacagcctac      240
atggagctga gcagcctgag atctgaggac acggccgtgt attactgttc aagttcaaac    300
tgggtcggga gttactgggg ccaaggaacc ctggtcaccg tctcctca                 348

SEQ ID NO: 24              moltype = DNA   length = 336
FEATURE                    Location/Qualifiers
source                     1..336
                           mol_type = other DNA
                           organism = Mus musculus
SEQUENCE: 24
gatgttgtga tgacccagac tccactcact ttgtcggtta ccattggaca aacagcctcc    60
atctcttgca agtcaagtca gagcctctta gaaagtgatg gaaagaccta tttgaattgg    120
ttgtcacaga ggccaggcca gtctccaaag cgcctaatct atctggtgtc tagactggac    180
tctggagtcc ctgacaggtt cactggcagt ggatcaggga cagatttcac actgaaaatc    240
agcagagtgg aggctgagga tttgggagtt tattattgtt ggcaaggcac acatcttcct    300
cagacgttcg gtggaggcac caagctggag atcaaa                              336

SEQ ID NO: 25              moltype = DNA   length = 336
FEATURE                    Location/Qualifiers
misc_feature               1..336
                           note = Humanized light chain variable region VK1
source                     1..336
                           mol_type = other DNA
                           organism = synthetic construct
SEQUENCE: 25
gatgttgtga tgactcagtc tccactcact ctgtcggtca cccttggaca gccgccctcc    60
atctcctgca agtctagtca aagcctctta gaaagtgatg gaaagaccta cttgaattgg    120
ttgcagcaga ggccaggcca atctccaagg cgcctaattt atctggtttc tagactggac    180
tctggggtcc cagacagatt cactggcagt gggtcaggga ctgatttcac actgaaaatc    240
agcagggtgg aggctgagga tgttggggtt tattactgct ggcaaggcac acatcttcct    300
cagactttcg gcgagggac caaggtggag atcaaa                               336

SEQ ID NO: 26              moltype = DNA   length = 336
FEATURE                    Location/Qualifiers
misc_feature               1..336
                           note = Humanized light chain variable region VK2
source                     1..336
                           mol_type = other DNA
                           organism = synthetic construct
SEQUENCE: 26
gatgttgtga tgactcagtc tccactctcc ctgcccgtca cccttggaca gccggcctcc    60
atctcctgca agtctagtca aagcctctta gaaagtgatg gaaagaccta cttgaattgg    120
ttgcagcaga ggccaggcca atctccaagg cgcctaattt atctggtttc tagactggac    180
tctggggtcc cagacagatt cactggcagt gggtcaggga ctgatttcac actgaaaatc    240
agcagggtgg aggctgagga tgttgggtt tattactgct ggcaaggcac acatcttcct    300
cagactttcg gcgagggac caaggtggag atcaaa                               336

SEQ ID NO: 27              moltype = DNA   length = 336
```

| FEATURE | Location/Qualifiers |
|---|---|
| misc_feature | 1..336 |
| | note = Humanized light chain variable region VK3 |
| source | 1..336 |
| | mol_type = other DNA |
| | organism = synthetic construct |

SEQUENCE: 27

```
gatgttgtga tgactcagtc tccactctcc ctgcccgtca cccttggaca gccggcctcc    60
atctcctgca agtctagtca aagcctctta gaaagtgatg gaaagaccta cttgaattgg   120
ttgcagcaga ggccaggcca atctccaagg cgcctaattt atctggtttc tagactggac   180
tctggggtcc cagacagatt cagcggcagt gggtcaggca ctgatttcac actgaaaatc   240
agcagggtgg aggctgagga tgttggggtt tattactgct ggcaaggcac acatcttcct   300
cagactttcg gcggagggac caaggtggag atcaaa                             336
```

| SEQ ID NO: 28 | moltype = DNA  length = 336 |
|---|---|
| FEATURE | Location/Qualifiers |
| misc_feature | 1..336 |
| | note = Humanized light chain variable region VK4 |
| source | 1..336 |
| | mol_type = other DNA |
| | organism = synthetic construct |

SEQUENCE: 28

```
gatgttgtga tgactcagtc tccactctcc ctgcccgtca cccttggaca gccggcctcc    60
atctcctgca agtctagtca aagcctctta gaaagtgatg gaaagaccta cttgaattgg   120
tttcagcaga ggccaggcca atctccaagg cgcctaattt atctggtttc tagactggac   180
tctggggtcc cagacagatt cagcggcagt gggtcaggca ctgatttcac actgaaaatc   240
agcagggtgg aggctgagga tgttggggtt tattactgct ggcaaggcac acatcttcct   300
cagactttcg gcggagggac caaggtggag atcaaa                             336
```

| SEQ ID NO: 29 | moltype = AA  length = 40 |
|---|---|
| FEATURE | Location/Qualifiers |
| source | 1..40 |
| | mol_type = protein |
| | organism = Homo sapiens |

SEQUENCE: 29

PEKDSRVSVT KPFMLPPVAA SSLRNDSSSS NRKAKNPPGD                          40

| SEQ ID NO: 30 | moltype = AA  length = 21 |
|---|---|
| FEATURE | Location/Qualifiers |
| source | 1..21 |
| | mol_type = protein |
| | organism = Homo sapiens |

SEQUENCE: 30

ASSLRNDSSS SNRKAKNPPG D                                              21

| SEQ ID NO: 31 | moltype = AA  length = 8 |
|---|---|
| FEATURE | Location/Qualifiers |
| source | 1..8 |
| | mol_type = protein |
| | organism = Homo sapiens |

SEQUENCE: 31

SSNRKAKN                                                              8

| SEQ ID NO: 32 | moltype = AA  length = 14 |
|---|---|
| FEATURE | Location/Qualifiers |
| source | 1..14 |
| | mol_type = protein |
| | organism = Homo sapiens |

SEQUENCE: 32

SSSSNRKAKN PPGD                                                      14

| SEQ ID NO: 33 | moltype = AA  length = 14 |
|---|---|
| FEATURE | Location/Qualifiers |
| source | 1..14 |
| | mol_type = protein |
| | organism = Homo sapiens |

SEQUENCE: 33

ASSLRNDSSS SNRK                                                      14

| SEQ ID NO: 34 | moltype = AA  length = 29 |
|---|---|
| FEATURE | Location/Qualifiers |
| source | 1..29 |
| | mol_type = protein |
| | organism = Homo sapiens |

SEQUENCE: 34

DSRVSVTKPF MLPPVAASSL RNDSSSSNR                                      29

| SEQ ID NO: 35 | moltype = AA  length = 7 |
|---|---|
| FEATURE | Location/Qualifiers |

```
source                          1..7
                                mol_type = protein
                                organism = Homo sapiens
SEQUENCE: 35
SNRKAKN                                                                        7

SEQ ID NO: 36                   moltype = AA  length = 13
FEATURE                         Location/Qualifiers
source                          1..13
                                mol_type = protein
                                organism = Homo sapiens
SEQUENCE: 36
ASSLRNDSSS SNR                                                                13

SEQ ID NO: 37                   moltype = AA  length = 17
FEATURE                         Location/Qualifiers
REGION                          1..17
                                note = VH5 CDR2
source                          1..17
                                mol_type = protein
                                organism = synthetic construct
SEQUENCE: 37
QIYPGDGDTH YNGKFQG                                                            17

SEQ ID NO: 38                   moltype = AA  length = 443
FEATURE                         Location/Qualifiers
REGION                          1..443
                                note = VH0 IgG4 heavy chain
source                          1..443
                                mol_type = protein
                                organism = synthetic construct
SEQUENCE: 38
QVQLQQSGAE LVRPGSSVKI SCKSSGYAFS SYWMNWVKQR PGQGLEWIGQ IYPGDGDTHY            60
NGKFKGKATL TADKSSSTAY MQLSRLTSED SAVYFCSSSN WVGSYWGQGT LVTVSSASTK          120
GPSVFPLAPC SRSTSESTAA LGCLVKDYFP EPVTVSWNSG ALTSGVHTFP AVLQSSGLYS          180
LSSVVTVPSS SLGTKTYTCN VDHKPSNTKV DKRVESKYGP PCPPCPAPEF EGGPSVFLFP          240
PKPKDTLMIS RTPEVTCVVV DVSQEDPEVQ FNWYVDGVEV HNAKTKPREE QFNSTYRVVS          300
VLTVLHQDWL NGKEYKCKVS NKGLPSSIEK TISKAKGQPR EPQVYTLPPS QEEMTKNQVS          360
LTCLVKGFYP SDIAVEWESN GQPENNYKTT PPVLDSDGSF FLYSRLTVDK SRWQEGNVFS          420
CSVMHEALHN HYTQKSLSLS LGK                                                  443

SEQ ID NO: 39                   moltype = AA  length = 219
FEATURE                         Location/Qualifiers
REGION                          1..219
                                note = VK0 Kappa light chain
source                          1..219
                                mol_type = protein
                                organism = synthetic construct
SEQUENCE: 39
DVVMTQTPLT LSVTIGQTAS ISCKSSQSLL ESDGKTYLNW LSQRPGQSPK RLIYLVSRLD            60
SGVPDRFTGS GSGTDFTLKI SRVEAEDLGV YYCWQGTHLP QTFGGGTKLE IKRTVAAPSV          120
FIFPPSDEQL KSGTASVVCL LNNFYPREAK VQWKVDNALQ SGNSQESVTE QDSKDSTYSL          180
SSTLTLSKAD YEKHKVYACE VTHQGLSSPV TKSFNRGEC                                 219

SEQ ID NO: 40                   moltype = AA  length = 327
FEATURE                         Location/Qualifiers
REGION                          1..327
                                note = heavy chain constant region
source                          1..327
                                mol_type = protein
                                organism = synthetic construct
SEQUENCE: 40
ASTKGPSVFP LAPCSRSTSE STAALGCLVK DYFPEPVTVS WNSGALTSGV HTFPAVLQSS            60
GLYSLSSVVT VPSSSLGTKT YTCNVDHKPS NTKVDKRVES KYGPPCPPCP APEFEGGPSV          120
FLFPPKPKDT LMISRTPEVT CVVVDVSQED PEVQFNWYVD GVEVHNAKTK PREEQFNSTY          180
RVVSVLTVLH QDWLNGKEYK CKVSNKGLPS SIEKTISKAK GQPREPQVYT LPPSQEEMTK          240
NQVSLTCLVK GFYPSDIAVE WESNGQPENN YKTTPPVLDS DGSFFLYSRL TVDKSRWQEG          300
NVFSCSVMHE ALHNHYTQKS LSLSLGK                                              327

SEQ ID NO: 41                   moltype = AA  length = 107
FEATURE                         Location/Qualifiers
source                          1..107
                                mol_type = protein
                                organism = Homo sapiens
SEQUENCE: 41
RTVAAPSVFI FPPSDEQLKS GTASVVCLLN NFYPREAKVQ WKVDNALQSG NSQESVTEQD            60
SKDSTYSLSS TLTLSKADYE KHKVYACEVT HQGLSSPVTK SFNRGEC                        107

SEQ ID NO: 42                   moltype = AA  length = 443
```

| | | |
|---|---|---|
| FEATURE | Location/Qualifiers | |
| REGION | 1..443 | |
| | note = 5H10 VH1 Heavy Chain | |
| source | 1..443 | |
| | mol_type = protein | |
| | organism = synthetic construct | |

SEQUENCE: 42
```
QVQLVQSGAE LKKPGSSVKI SCKSSGYAFS SYWMNWVKQR PGQGLEWIGQ IYPGDGDTHY   60
NGKFKGKATL TADKSTSTAY MELSSLTSED SAVYFCSSSN WVGSYWGQGT LVTVSSASTK  120
GPSVFPLAPC SRSTSESTAA LGCLVKDYFP EPVTVSWNSG ALTSGVHTFP AVLQSSGLYS  180
LSSVVTVPSS SLGTKTYTCN VDHKPSNTKV DKRVESKYGP PCPPCPAPEF EGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                         443
```

| | | |
|---|---|---|
| SEQ ID NO: 43 | moltype = AA   length = 443 | |
| FEATURE | Location/Qualifiers | |
| REGION | 1..443 | |
| | note = 5H10 VH2 Heavy Chain | |
| source | 1..443 | |
| | mol_type = protein | |
| | organism = synthetic construct | |

SEQUENCE: 43
```
QVQLVQSGAE VKKPGSSVKI SCKSSGYAFS SYWMNWVKQR PGQGLEWIGQ IYPGDGDTHY   60
NGKFKGKATL TADKSTSTAY MELSSLRSED TAVYFCSSSN WVGSYWGQGT LVTVSSASTK  120
GPSVFPLAPC SRSTSESTAA LGCLVKDYFP EPVTVSWNSG ALTSGVHTFP AVLQSSGLYS  180
LSSVVTVPSS SLGTKTYTCN VDHKPSNTKV DKRVESKYGP PCPPCPAPEF EGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                         443
```

| | | |
|---|---|---|
| SEQ ID NO: 44 | moltype = AA   length = 443 | |
| FEATURE | Location/Qualifiers | |
| REGION | 1..443 | |
| | note = 5H10 VH3 Heavy Chain | |
| source | 1..443 | |
| | mol_type = protein | |
| | organism = synthetic construct | |

SEQUENCE: 44
```
QVQLVQSGAE VKKPGSSVKV SCKSSGYAFS SYWMNWVRQR PGQGLEWIGQ IYPGDGDTHY   60
NGKFKGKATL TADKSTSTAY MELSSLRSED TAVYFCSSSN WVGSYWGQGT LVTVSSASTK  120
GPSVFPLAPC SRSTSESTAA LGCLVKDYFP EPVTVSWNSG ALTSGVHTFP AVLQSSGLYS  180
LSSVVTVPSS SLGTKTYTCN VDHKPSNTKV DKRVESKYGP PCPPCPAPEF EGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                         443
```

| | | |
|---|---|---|
| SEQ ID NO: 45 | moltype = AA   length = 443 | |
| FEATURE | Location/Qualifiers | |
| REGION | 1..443 | |
| | note = 5H10 VH4 Heavy Chain | |
| source | 1..443 | |
| | mol_type = protein | |
| | organism = synthetic construct | |

SEQUENCE: 45
```
QVQLVQSGAE VKKPGSSVKV SCKSSGYAFS SYWMNWVRQR PGQGLEWIGQ IYPGDGDTHY   60
NGKFKGRVTI TADKSTSTAY MELSSLRSED TAVYFCSSSN WVGSYWGQGT LVTVSSASTK  120
GPSVFPLAPC SRSTSESTAA LGCLVKDYFP EPVTVSWNSG ALTSGVHTFP AVLQSSGLYS  180
LSSVVTVPSS SLGTKTYTCN VDHKPSNTKV DKRVESKYGP PCPPCPAPEF EGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                         443
```

| | | |
|---|---|---|
| SEQ ID NO: 46 | moltype = AA   length = 443 | |
| FEATURE | Location/Qualifiers | |
| REGION | 1..443 | |
| | note = 5H10 VH5 Heavy Chain | |
| source | 1..443 | |
| | mol_type = protein | |
| | organism = synthetic construct | |

SEQUENCE: 46
```
QVQLVQSGAE VKKPGSSVKV SCKSSGYAFS SYWMNWVRQR PGQGLEWIGQ IYPGDGDTHY   60
NGKFQGRVTI TADKSTSTAY MELSSLRSED TAVYYCSSSN WVGSYWGQGT LVTVSSASTK  120
GPSVFPLAPC SRSTSESTAA LGCLVKDYFP EPVTVSWNSG ALTSGVHTFP AVLQSSGLYS  180
LSSVVTVPSS SLGTKTYTCN VDHKPSNTKV DKRVESKYGP PCPPCPAPEF EGGPSVFLFP  240
```

```
PKPKDTLMIS RTPEVTCVVV DVSQEDPEVQ FNWYVDGVEV HNAKTKPREE QFNSTYRVVS    300
VLTVLHQDWL NGKEYKCKVS NKGLPSSIEK TISKAKGQPR EPQVYTLPPS QEEMTKNQVS    360
LTCLVKGFYP SDIAVEWESN GQPENNYKTT PPVLDSDGSF FLYSRLTVDK SRWQEGNVFS    420
CSVMHEALHN HYTQKSLSLS LGK                                           443

SEQ ID NO: 47           moltype = AA  length = 219
FEATURE                 Location/Qualifiers
REGION                  1..219
                        note = 5H10 VK1 Light Chain
source                  1..219
                        mol_type = protein
                        organism = synthetic construct
SEQUENCE: 47
DVVMTQSPLT LSVTLGQPAS ISCKSSQSLL ESDGKTYLNW LQQRPGQSPR RLIYLVSRLD     60
SGVPDRFTGS GSGTDFTLKI SRVEAEDVGV YYCWQGTHLP QTFGGGTKVE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219

SEQ ID NO: 48           moltype = AA  length = 219
FEATURE                 Location/Qualifiers
REGION                  1..219
                        note = 5H10 VK2 Light Chain
source                  1..219
                        mol_type = protein
                        organism = synthetic construct
SEQUENCE: 48
DVVMTQSPLS LPVTLGQPAS ISCKSSQSLL ESDGKTYLNW LQQRPGQSPR RLIYLVSRLD     60
SGVPDRFTGS GSGTDFTLKI SRVEAEDVGV YYCWQGTHLP QTFGGGTKVE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219

SEQ ID NO: 49           moltype = AA  length = 219
FEATURE                 Location/Qualifiers
REGION                  1..219
                        note = 5H10 VK3 Light Chain
source                  1..219
                        mol_type = protein
                        organism = synthetic construct
SEQUENCE: 49
DVVMTQSPLS LPVTLGQPAS ISCKSSQSLL ESDGKTYLNW LQQRPGQSPR RLIYLVSRLD     60
SGVPDRFSGS GSGTDFTLKI SRVEAEDVGV YYCWQGTHLP QTFGGGTKVE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219

SEQ ID NO: 50           moltype = AA  length = 219
FEATURE                 Location/Qualifiers
REGION                  1..219
                        note = 5H10 VK4 Light Chain
source                  1..219
                        mol_type = protein
                        organism = synthetic construct
SEQUENCE: 50
DVVMTQSPLS LPVTLGQPAS ISCKSSQSLL ESDGKTYLNW FQQRPGQSPR RLIYLVSRLD     60
SGVPDRFSGS GSGTDFTLKI SRVEAEDVGV YYCWQGTHLP QTFGGGTKVE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219
```